United States Patent
Griessl

(10) Patent No.: US 11,161,883 B2
(45) Date of Patent: Nov. 2, 2021

(54) MODIFIED PEPTIDES

(71) Applicant: SASINAPAS CO., LTD., Bangkok (TH)

(72) Inventor: Martin Griessl, Hohenschambach (DE)

(73) Assignee: SASINAPAS CO., LTD, Bangkok (TH)

( * ) Notice: Subject to any disclaimer, the term of this patent is extended or adjusted under 35 U.S.C. 154(b) by 23 days.

(21) Appl. No.: 16/464,848

(22) PCT Filed: Nov. 30, 2017

(86) PCT No.: PCT/IB2017/057513
§ 371 (c)(1),
(2) Date: May 29, 2019

(87) PCT Pub. No.: WO2018/100516
PCT Pub. Date: Jun. 7, 2018

(65) Prior Publication Data
US 2019/0337997 A1 Nov. 7, 2019

(30) Foreign Application Priority Data
Nov. 30, 2016 (WO) .................. PCT/IB2017/057193

(51) Int. Cl.
| | | |
|---|---|---|
| C07K 14/315 | (2006.01) | |
| A23L 3/3463 | (2006.01) | |
| C07K 7/08 | (2006.01) | |
| C07K 14/47 | (2006.01) | |
| C11D 3/386 | (2006.01) | |
| C11D 3/48 | (2006.01) | |
| C12N 9/36 | (2006.01) | |
| A61K 38/00 | (2006.01) | |

(52) U.S. Cl.
CPC ...... *C07K 14/3156* (2013.01); *A23L 3/34635* (2013.01); *C07K 7/08* (2013.01); *C07K 14/4723* (2013.01); *C11D 3/38636* (2013.01); *C11D 3/48* (2013.01); *C12N 9/2462* (2013.01); *A61K 38/00* (2013.01); *C07K 2319/55* (2013.01); *C12N 2795/10122* (2013.01)

(58) Field of Classification Search
None
See application file for complete search history.

(56) References Cited

U.S. PATENT DOCUMENTS

2012/0316102 A1* 12/2012 Misse Brumas ............................ C07K 14/43563
514/2.3

FOREIGN PATENT DOCUMENTS

| EP | 3058950 | 8/1916 |
|---|---|---|
| WO | WO 2009/000089 | 12/2008 |
| WO | WO 2010/149792 | 12/2010 |
| WO | WO 2011/023702 | 3/2011 |
| WO | WO 2011/095939 | 8/2011 |
| WO | WO 2014/001572 | 1/2014 |
| WO | WO 2015/070911 | 5/2015 |
| WO | WO 2015/121443 | 8/2015 |

OTHER PUBLICATIONS

Briers, Yves, and Rob Lavigne. "Breaking barriers: expansion of the use of endolysins as novel antibacterials against Gram-negative bacteria," *Future microbiology* 10.3 (2015): 377-390.

Briers, Yves, et al. "Engineered endolysin-based "Antilysins" to combat multidrug-resistant gram-negative pathogens," *MBio* 5.4 (2014).

Gerstmans, Hans, et al, "From endolysins to Artilysin® s: novel enzyme-based approaches to kill drug-resistant bacteria." *Biochemical Society Transactions* 44.1 (2016): 123-128.

International Search Report and Written Opinion issued in International Application No. PCT/IB2017/057513, dated Mar. 5, 2018.

Rodriguez-Rubio, Lorena, et al. "'Artilysation'Of endolysin λSa2lys strongly improves its enzymatic and antibacterial activity against *streptococci*," *Scientific reports* 6.1 (2016): 1-11.

Tossiklessandro, et al. "identification and characterization of a primary antibacterial domain in CAP18, a lipopolysaccharide binding protein from rabbit leukocytes," *FEBS letters* 339.1-2 (1994): 108-112.

Briers, Yves, et al. "A standardized approach for accurate quantification of imurein hydrolase activity in high-throughput assays." *Journal of biochemical and biophysical methods* 70.3 (2007): 531-533.

Donovan, David M., Michelle Lardeo, and Juli Foster-Frey. "Lysis of staphylococcal mastitis pathogens by bacteriophage phi11 endolysin." *FEMS microbiology letters* 265.1 (2006): 133-139.

* cited by examiner

*Primary Examiner* — Maury A Audet
(74) *Attorney, Agent, or Firm* — Parker Highlander PLLC

(57) ABSTRACT

The present invention relates to the field of antimicrobial agents. In particular, the present invention relates to polypeptides comprising the sequence of a peptidoglycan hydrolase and a peptide sequence heterologous to the peptidoglycan hydrolase wherein said heterologous peptide sequence comprises a specific sequence motif which is 16, 17, 18, 19 or 20 amino acids in length. The present invention relates also to corresponding nucleic acids, vectors, bacteriophages, host cells, compositions and kits. The present inventions also relates to the use of said polypeptides, nucleic acids, vectors, bacteriophages, host cells, compositions and kits in methods for treatment of the human or animal body by surgery or therapy or in diagnostic methods practiced on the human or animal body. The polypeptides, nucleic acids, vectors, bacteriophages, host cells, compositions and kits according to the invention may also be used as an antimicrobial in, e.g., food or feed, in cosmetics, or as disinfecting agent.

10 Claims, 6 Drawing Sheets
Specification includes a Sequence Listing.

Fig.1

| Position in sequence motif \ Sequence motif alternatives | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 16 |   |   |   |   |   |   |   | X | X | X | X | X | X | X |   |   |   |   |
| 15 |   | X |   |   |   |   |   |   |   |   |   |   | X | X | X | X | X | X |
| 14 |   | X | X | X | X | X | X |   |   |   |   |   |   |   |   |   |   | X |
| 13 |   |   |   |   |   | X | X | X | X | X | X | X |   |   |   |   |   |   |
| 12 |   |   |   |   |   |   |   |   |   | X | X | X | X | X | X |   |   |   |
| 11 |   | X | X | X |   |   |   |   |   |   |   |   |   | X | X | X | X |   |
| 10 |   |   | X | X | X | X | X | X |   |   |   |   |   |   |   |   |   |   |
| 9 |   |   |   |   |   |   | X | X | X | X | X | X | X |   |   |   |   |   |
| 8 |   |   |   |   |   |   |   |   |   |   |   | X | X | X | X | X | X |   |
| 7 |   | X | X | X | X |   |   |   |   |   |   |   |   |   |   | X | X |   |
| 6 |   |   |   | X | X | X | X | X | X |   |   |   |   |   |   |   |   |   |
| 5 |   |   |   |   |   |   |   |   | X | X | X | X | X | X |   |   |   |   |
| 4 |   | X | X |   |   |   |   |   |   |   |   |   |   | X | X | X | X |   |
| 3 |   | X | X | X | X | X | X |   |   |   |   |   |   |   |   |   |   |   |
| 2 |   |   |   |   |   | X | X | X | X | X | X | X |   |   |   |   |   |   |
| 1 |   |   |   |   |   |   |   | X | X | X | X | X | X | X |   |   |   |   |

Fig.2a

| Position in sequence motif \ Sequence motif alternatives | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 1 |  |  |  |  |  |  |  |  |  |  | X | X | X | X | X | X |  |  |
| 2 |  |  |  |  |  | X | X | X | X | X | X |  |  |  |  |  |  |  |
| 3 | X | X | X | X | X | X | X |  |  |  |  |  |  |  |  |  |  |  |
| 4 | X | X |  |  |  |  |  |  |  |  |  |  | X | X | X | X | X |  |
| 5 |  |  |  |  |  |  |  | X | X | X | X | X | X |  |  |  |  |  |
| 6 |  |  |  |  | X | X | X | X | X | X |  |  |  |  |  |  |  |  |
| 7 | X | X | X | X |  |  |  |  |  |  |  |  |  |  |  | X | X |  |
| 8 |  |  |  |  |  |  |  |  |  | X | X | X | X | X | X |  |  |  |
| 9 |  |  |  |  |  |  | X | X | X | X | X | X |  |  |  |  |  |  |
| 10 |  |  | X | X | X | X | X | X |  |  |  |  |  |  |  |  |  |  |
| 11 |  | X | X |  |  |  |  |  |  |  |  |  |  | X | X | X | X |  |
| 12 |  |  |  |  |  |  |  |  | X | X | X | X | X | X |  |  |  |  |
| 13 |  |  |  |  |  | X | X | X | X | X | X | X |  |  |  |  |  |  |
| 14 | X | X | X | X | X | X |  |  |  |  |  |  |  |  |  |  |  | X |
| 15 | X |  |  |  |  |  |  |  |  |  |  |  | X | X | X | X | X | X |
| 16 |  |  |  |  |  |  |  | X | X | X | X | X | X | X |  |  |  |  |
| 17 |  |  | X | X | X | X | X | X | X |  |  |  |  |  |  |  |  |  |

| Position \ Alternative | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 1 |  |  |  |  |  |  |  |  |  | X | X | X | X | X | X | X |  |  |
| 2 |  |  |  |  | X | X | X | X | X | X |  |  |  |  |  |  |  |  |
| 3 | X | X | X | X | X | X | X |  |  |  |  |  |  |  |  |  |  |  |
| 4 | X | X |  |  |  |  |  |  |  |  |  |  | X | X | X | X | X |  |
| 5 |  |  |  |  |  |  |  |  | X | X | X | X | X | X |  |  |  |  |
| 6 |  |  |  | X | X | X | X | X |  |  |  |  |  |  |  |  |  |  |
| 7 | X | X | X | X |  |  |  |  |  |  |  |  |  |  |  | X | X |  |
| 8 |  |  |  |  |  |  |  |  |  |  | X | X | X | X | X | X |  |  |
| 9 |  |  |  |  |  |  | X | X | X | X | X |  |  |  |  |  |  |  |
| 10 |  |  | X | X | X | X | X | X |  |  |  |  |  |  |  |  |  |  |
| 11 | X | X | X |  |  |  |  |  |  |  |  |  | X | X |  | X | X |  |
| 12 |  |  |  |  |  |  |  |  |  | X | X |  | X | X | X | X |  |  |
| 13 |  |  |  |  | X | X | X | X | X | X | X |  |  |  |  |  |  |  |
| 14 | X | X | X | X | X | X |  |  |  |  |  |  |  |  |  |  |  | X |
| 15 | X |  |  |  |  |  |  |  |  |  |  |  | X | X | X | X | X | X |
| 16 |  |  |  |  |  |  | X | X | X | X | X | X |  |  |  |  |  |  |
| 17 |  |  | X | X | X | X | X | X | X |  |  |  |  |  |  |  |  |  |
| 18 | X | X | X | X |  |  |  |  |  |  |  |  |  |  |  | X | X | X |
| 19 |  |  |  |  |  |  |  |  |  |  | X |  | X | X | X | X | X | X |

MODIFIED PEPTIDES

This application is a national phase application under 35 U.S.C. § 371 of International Application No. PCT/IB2017/057513, filed Nov. 30, 2017, which claims benefit of priority to International Application No. PCT/IB2016/057193, filed Nov. 30, 2016, the entire contents of each of which are hereby incorporated by reference.

BACKGROUND OF THE INVENTION

I. Field of the Invention

The present invention relates to the field of antimicrobial agents. In particular, the present invention relates to polypeptides comprising the sequence of a peptidoglycan hydrolase and a peptide sequence heterologous to the peptidoglycan hydrolase wherein said heterologous peptide sequence comprises a specific sequence motif which is 16, 17, 18, 19 or 20 amino acids in length. The present invention relates also to corresponding nucleic acids, vectors, bacteriophages, host cells, compositions and kits. The present inventions also relates to the use of said polypeptides, nucleic acids, vectors, bacteriophages, host cells, compositions and kits in methods for treatment of the human or animal body by surgery or therapy or in diagnostic methods practiced on the human or animal body. The polypeptides, nucleic acids, vectors, bacteriophages, host cells, compositions and kits according to the invention may also be used as an antimicrobial in, e.g., food or feed, in cosmetics, or as disinfecting agent.

II. Description of Related Art

Resistance to conventional antibiotics is becoming an increasing health risk for humankind. New antibiotics resistances mechanisms are emerging and rapidly spreading globally. Consequently, the ability to treat common infectious diseases may become more and more difficult in the near future. This danger has been readily understood in the art and new approaches to combat infectious agents are explored.

Among these new approaches is the fusion of peptidoglycan hydrolases with antimicrobial peptides. In WO 2010/149792, such fusions have been shown to be effective in treating a number of bacteria. WO 2010/149792 discloses various combinations of peptidoglycan hydrolases and peptides. Interestingly, and for unknown reasons, not all combinations of peptidoglycan hydrolases and peptides are equally effective. While combinations with the 29mer antimicrobial peptide SMAP-29 peptide (SEQ ID NO:1) showed very high antimicrobial activity, other peptides combined with the same peptidoglycan hydrolases increased the antimicrobial activity only to a lesser extent.

Thus, there is still a need in the art for further improvement in the design of such antibacterial agents.

It was thus the objective of the inventor to provide new antimicrobial agents, which provide improved results in comparison to random combinations of peptidoglycan hydrolases with antimicrobial peptides.

This problem is solved by the subject-matter as set forth below and in the appended claims.

SUMMARY OF THE INVENTION

The inventor of the present invention has surprisingly found that effective antimicrobial combinations of peptidoglycan hydrolases and peptides can be purposeful generated, if peptides exhibiting a certain general amino acid sequence motif are used. By applying this pattern, the inventor rendered previously existing antimicrobial peptides more effective. Moreover, by introducing respective mutations, the inventor even succeeded in transforming an entirely unrelated peptide, i.e. previously not known for any antimicrobial activity, de novo into a useful compound in this regard.

In a first aspect the present invention relates to a polypeptide comprising a sequence motif which:
  i) is 16, 17, 18, 19 or 20 amino acids in length;
  ii) comprises at least 40% and at most 60% amino acids selected from a first group of amino acids consisting of lysine, arginine and histidine,
    wherein each amino acid is selected independently from said first group,
    wherein each amino acid selected from this first group is arranged in said sequence motif either alone, pairwise together with a further amino acid selected from the first group, or in a block with 2 further amino acids selected from the first group, but does not occur in a block with 3 or more amino acids selected from the first group, wherein at least 2 pairs of amino acids selected from the first group are present in said sequence motif, and wherein at most one block with 3 of the amino acids selected from the first group in a row is present in said sequence motif, with the additional proviso, that if such block with 3 amino acids of the first group is present in said sequence motif, then the amino acids at positions 12, −11, −8, −5, −4, +6, +7, +10, +13, and +14 relative to the first amino acid of the 3 amino acid block are—provided the respective position may be found in said sequence motif—not selected from said first group,
  iii) comprises at least 40% and at most 60% amino acids selected from a second group of amino acids consisting of alanine, glycine, isoleucine, leucine, phenylalanine, serine, threonine, tryptophan, tyrosine and valine,
    wherein each amino acid is selected independently from said second group,
    wherein at least three different amino acids are selected from this second group, if the sum of amino acids of selected from the first group and selected from the second group yield 100% of the sequence motif,
    wherein the sequence motif does not comprise the sequence AFV, if the sequence motif contains at least two single, non-adjacent phenylalanine residues and at least one of these phenylalanine residues is directly preceded by a lysine residue, and
    wherein the sequence motif does not comprise the sequence AALTH (SEQ ID NO:2), if the sequence motif contains at least three non-adjacent histidine residues,
  iv) wherein the remaining amino acids of said sequence motif, if any are present in the motif, are selected from a third group consisting of asparagine, aspartic acid, glutamine, glutamic acid, methionine, or cysteine, wherein each of said amino acids is selected independently from said third group, and wherein glutamine may be selected only once and wherein the selection may furthermore not comprise a combination of glutamine and glutamic acid, and
wherein said polypeptide does not comprise the sequence of SMAP-29 peptide (SEQ ID NO:1).

Particularly preferred embodiments of the inventive polypeptide are fusion proteins of the invention, in which the polypeptide of the invention comprises additionally the sequence of a peptidoglycan hydrolase.

In further aspects, the present invention relates to nucleic acids encoding an inventive polypeptide, vectors or bacteriophages comprising an inventive nucleic acid as well as host cells comprising an inventive polypeptide, nucleic acid, vector, and/or bacteriophage.

The present invention relates in a further aspect also to compositions comprising a polypeptide, nucleic acid, vector, bacteriophage, and/or host cell according to the present invention. Such compositions are preferably pharmaceutical compositions comprising a pharmaceutically acceptable carrier, diluent, or excipient.

In a further aspect the present invention contemplates kits comprising an inventive polypeptide, nucleic acid, vector, bacteriophage, and/or host cell, and further comprising a peptidoglycan hydrolase, or nucleic acids, vectors, bacteriophages, and/or host cells encoding or comprising, respectively, said peptidoglycan hydrolase.

Finally, the present invention relates to polypeptides, nucleic acids, vectors, bacteriophages, host cells, compositions and/or kits of the present invention for use in methods of treatment, in particular for the treatment or prevention of bacterial infections.

DESCRIPTION OF ILLUSTRATIVE EMBODIMENTS

I. Definitions

The term "polypeptide" as used herein refers in particular to a polymer of amino acid residues linked by peptide bonds in a specific sequence. The amino acid residues of a polypeptide may be modified by e.g. covalent attachments of various groups such as carbohydrates and phosphate. Other substances may be more loosely associated with the polypeptide, such as heme or lipid, giving rise to conjugated polypeptides which are also comprised by the term "polypeptide" as used herein. The term as used herein is intended to encompass also proteins. Thus, the term "polypeptide" also encompasses for example complexes of two or more amino acid polymer chains. The term "polypeptide" does encompass embodiments of polypeptides which exhibit optionally modifications typically used in the art, e.g. biotinylation, acetylation, pegylation, chemical changes of the amino-, SH- or carboxyl-groups (e.g. protecting groups) etc. As will become apparent from the description below, the polypeptide according to the invention may be an artificially engineered polypeptide, which does not exist in this form in nature. Such polypeptide may for example exhibit artificial mutations vis-à-vis a naturally occurring polypeptide or may comprise heterologous sequences, or may be a fragment of a naturally occurring polypeptide, which fragment does not occur in this form in nature. Furthermore, the polypeptide according to the present invention may be a fusion protein, i.e. represent the linkage of at least two amino acid sequences which do not occur in this combination in nature. The term "polypeptide" as used herein is not limited to a specific length of the amino acid polymer chain. However, the minimum length is 16 amino acids. Usually, but not necessarily, a typical polypeptide of the present invention will not exceed about 1000 amino acids in length. The inventive polypeptide may for instance be at most about 750 amino acids long, at most about 500 amino acids long or at most about 300 amino acids long. A possible length range for the inventive polypeptide, without being limited thereto, may thus for example be 16 to 1000 amino acids, 16 to about 50 amino acids, about 200 to about 750 amino acids, or about 225 to about 600 amino acids, or about 250 to about 350 amino acids.

The term "peptidoglycan hydrolase", as used herein, is generally understood in the art. It refers to any polypeptide which is capable of hydrolyzing the peptidoglycan of bacteria, such as Gram negative bacteria. The term is not restricted to a specific enzymatic cleavage mechanism. In terms of cleavage mechanism, the peptidoglycan hydrolase may be for example an endopeptidase, chitinase, T4 like muraminidase, lambda like muraminidase, N-acetyl-muramoyl-L-alanine-amidase (amidase), muramoyl-L-alanine-amidase, muramidase, lytic transglycosylase (C), lytic transglycosylase (M), N-acetyl-muramidase (lysozyme), N-acetyl-glucosaminidase or transglycosylases. Furthermore, the term encompasses naturally occurring peptidoglycan hydrolases, such as peptidoglycan hydrolases of eukaryotic, prokaryotic or viral (in particular bacteriophage) origin. The term encompasses for example vertebrate lysozymes (such as hen egg white lysozyme and human lysozyme), endolysins (e.g. KZ144 endolysin or Lys394 endolysin), Virion-associated peptidoglycan hydrolases (VAPGH), bacteriocins (e.g. lysostaphin) and autolysins. The "peptidoglycan hydrolase" may also be a synthetic or artificially modified polypeptide capable of hydrolyzing the peptidoglycan of bacteria. For example, enzymatically active shuffled endolysins in which domains of two or more endolysins have been swapped/exchanged do qualify as "peptidoglycan hydrolase" just as truncated endolysins, in which only the enzymatic active domain remains. The activity can be measured by assays well known in the art by a person skilled in the art as e.g. antibacterial assays which are e.g. described in Briers et al. (J. Biochem. Biophys Methods; 2007; 70: 531-533) or Donovan et al. (J. FEMS Microbiol Lett. 2006 December; 265(1) and similar publications.

If reference is herein made to "amino acid residues", then in general L-amino acid residues are meant.

The term "endolysin" as used herein refers to a bacteriophage-derived enzyme which is suitable to hydrolyse bacterial cell walls. Endolysins comprise at least one "enzymatically active domain" (EAD) having at least one of the following activities: endopeptidase, chitinase, T4 like muraminidase, lambda like muraminidase, N-acetyl-muramoyl-L-alanine-amidase (amidase), muramoyl-L-alanine-amidase, muramidase, lytic transglycosylase (C), lytic transglycosylase (M), N-acetyl-muramidase (lysozyme), N-acetyl-glucosaminidase or transglycosylases. In addition, the endolysins may contain also regions which are enzymatically inactive, but bind to the cell wall of the host bacteria, the so-called CBDs (cell wall binding domains).

The term "comprising", as used herein, shall not be construed as being limited to the meaning "consisting of" (i.e. excluding the presence of additional other matter). Rather, "comprising" implies that optionally additional matter may be present. The term "comprising" encompasses as particularly envisioned embodiments falling within its scope "consisting of" (i.e. excluding the presence of additional other matter) and "comprising but not consisting of" (i.e. requiring the presence of additional other matter), with the former being more preferred.

The use of the word "a" or "an", when used herein, may mean "one," but it is also consistent with the meaning of "one or more," "at least one," and "one or more than one."

II. Polypeptides

As already mentioned, the present invention relates in a first to a polypeptide comprising a sequence motif which:

i) is 16, 17, 18, 19 or 20 amino acids in length;
ii) comprises at least 40% and at most 60% amino acids selected from a first group of amino acids consisting of lysine, arginine and histidine,
   wherein each amino acid is selected independently from said first group,
   wherein each amino acid selected from this first group is arranged in said sequence motif either alone, pairwise together with a further amino acid selected from the first group, or in a block with 2 further amino acids selected from the first group, but does not occur in a block with 3 or more amino acids selected from the first group, wherein at least 2 pairs of amino acids selected from the first group are present in said sequence motif, and wherein at most one block with 3 of the amino acids selected from the first group in a row is present in said sequence motif, with the additional proviso, that if such block with 3 amino acids of the first group is present in said sequence motif, then the amino acids at positions 12, −11, −8, −5, −4, +6, +7, +10, +13, and +14 relative to the first amino acid of the 3 amino acid block are—provided the respective position may be found in said sequence motif—not selected from said first group,
iii) comprises at least 40% and at most 60% amino acids selected from a second group of amino acids consisting of alanine, glycine, isoleucine, leucine, phenylalanine, serine, threonine, tryptophan, tyrosine and valine,
   wherein each amino acid is selected independently from said second group,
   wherein at least three different amino acids are selected from this second group, if the sum of amino acids of selected from the first group and selected from the second group yield 100% of the sequence motif,
   wherein the sequence motif does not comprise the sequence AFV, if the sequence motif contains at least two single, non-adjacent phenylalanine residues and at least one of these phenylalanine residues is directly preceded by a lysine residue, and
   wherein the sequence motif does not comprise the sequence AALTH (SEQ ID NO:2), if the sequence motif contains at least three non-adjacent histidine residues,
iv) wherein the remaining amino acids of said sequence motif, if any are present in the motif, are selected from a third group consisting of asparagine, aspartic acid, glutamine, glutamic acid, methionine, or cysteine, wherein each of said amino acids is selected independently from said third group, and wherein glutamine may be selected only once and wherein the selection may furthermore not comprise a combination of glutamine and glutamic acid, and
wherein said fusion protein does not comprise the sequence of SMAP-29 peptide (SEQ ID NO:1).

The sequence motif defined above in i) to iii) may represent only a part of the sequence of the inventive polypeptide, i.e. the polypeptide of the invention is longer than the sequence motif. Alternatively, the sequence motif may be the sequence of the inventive polypeptide, i.e. the sequence of the inventive polypeptide is identical to the sequence of the sequence motif. Moreover, and as will be apparent from the example provided in FIG. 1, it is possible that the inventive polypeptide comprises one or more such sequence motifs. For instance, the 20mer motif may inherently comprise a 16mer motif also complying with the criteria set out above. The fact, that the inventive polypeptide comprises "a" sequence motif as defined above may thus not be understood that the inventive polypeptide may only comprise "one" sequence motif and no further (e.g. overlapping) sequence motifs also complying with the limits set out above.

The sequence motif of the inventive polypeptide may be 16, 17, 18, 19 or 20 amino acids in length. Preferably, the sequence motif is 17, 18 or 19 amino acids in length, even more preferably 17 or 18 amino acids in length.

The sequence motif of the inventive polypeptide comprises at least 40% and at most 60% amino acids selected from a first group of amino acids. Said first group consists of lysine, arginine and histidine. If the sequence motif is 16 amino acids long, it will exhibit at least 7 and at most 9 amino acids selected from this first group. If the sequence motif is 17 amino acids long, it will exhibit at least 7 and at most 10 amino acids selected from this first group. If the sequence motif is 18 amino acids long, it will exhibit at least 8 and at most 10 amino acids selected from this first group. If the sequence motif is 19 amino acids long, it will exhibit at least 8 and at most 11 amino acids selected from this first group. If the sequence motif is 20 amino acids long, it will exhibit at least 8 and at most 12 amino acids selected from this first group.

Preferred amino acids for selection within this first group are lysine and arginine. Preferably, the sequence motif does not comprise more than 50% histidine residues. Even more preferably, the sequence motif does not comprise more than 25% histidine residues. In some embodiments of the invention, the sequence motif comprises only one or even no histidine residue.

The amino acids selected from the first group are selected independently. This implies, for example, that if a given sequence motif comprises, e.g., eight amino acids selected from the first group, that each of these eight amino acid residues can be selected independently from previous or subsequent selections from said first group. The selected amino acids may thus comprise all three types of amino acids (lysine, arginine, and histidine), may be identical (e.g. 8 lysine or 8 arginine residues, respectively), or may comprise only two of the three types of amino acids (e.g. lysine and arginine). Likewise, independent selection does not prescribe any specific ratio between the individually selected amino acids. For example, and without being limited thereto, 8 amino acids selected from this first group may be 8 lysine residues, 7 arginine residues and 1 histidine residue or 3 arginine, 4 lysine and 1 histidine residue.

The positioning of the amino acid residues selected from the first group within the sequence motif is subject to certain limitations. Each amino acid selected from this first group may only be arranged in said sequence motif either alone, pairwise together with a further amino acid selected from the first group, or in a block with 2 further amino acids selected from the first group.

"Alone" means that an amino acid selected from said first group, e.g. lysine (K), is neither N-terminally nor C-terminally flanked by another amino acid from said first group. Adjacent amino acid residues may be selected from the second or, as the case may be, from the third group (e.g. L KE, N-KE (at N-terminus of motif), LK-C (at C-terminus of motif)). Noteworthy, potential further amino acids within the inventive polypeptide, but outside of the sequence motif, are not taken into account for this positional determination. An amino acid from the first group at one of the two ends of the sequence motif is thus considered to be positioned alone, even if the preceding (N-terminus) or subsequent (C-terminus) amino acid residue outside of the sequence motif is by chance also an arginine, histidine or lysine residue.

"Pairwise together with a further amino acid selected from the first group" means that within the sequence motif an amino acid selected from the first group is directly adjacent to another amino acid selected from the first group. This two amino acids form thereby a pair of amino acids selected from the first group. Said pair in turn is flanked C-terminally and N-terminally by amino acids from the second or, as the case may be, from the third group (e.g., L KRE (SEQ ID NO:3), N-KRE (at N-terminus of motif), L KR-C (at C-terminus of motif)). Potential further amino acids within the inventive polypeptide, but outside of the sequence motif, are again not taken into account for this positional determination.

"In a block with 2 further amino acids selected from the first group" means that three amino acids selected from the first group are directly adjacent to each other. Said block (or triplet) is flanked C-terminally and N-terminally by amino acids from the second or, as the case may be, from the third group (e.g., LKRKE (SEQ ID NO:4), N-KRKE (at N-terminus of motif; SEQ ID NO:5), LKRK-C (at C-terminus of motif; SEQ ID NO:6)). Potential further amino acids within the inventive polypeptide, but outside of the sequence motif, are again not taken into account for this positional determination. For amino acids arranged in such manner (triplet; block with 3 amino acids of the first group) an additional positional requirement must be met, namely that none of the amino acids at positions −12, −11, −8, −5, −4, +6, +7, +10, +13, and +14 relative to the first amino acid of the 3 amino acid block is—provided the respective position may be found in said sequence motif—an amino acid selected from said first group. Negative values indicate positions N-terminal of the first amino acid of the triplet; positive values refer to positions C-terminal of the first amino acid of the triplet. Basis for the positional calculation is the first (N-terminal) amino acid of the triplet (e.g. the amino acid directly N-terminal of the triplet would be −1, the amino acid directly C-terminal of the triplet would be +3). This limitation thus precludes a sequence like RRRGLR H (SEQ ID NO:7), because position +6 (H) is an amino acid of the first group. Whether the respective positions (−12, −11, −8, −5, −4, +6, +7, +10, +13, and +14) are present in the sequence motif or not will be dependent on the position of the triplet within the sequence motif and the length of the sequence motif. For example, if the triplet would be situated at the N-terminus of the sequence motif, then all negative values are obsolete (i.e. need not be taken into account). The same applies for the positive values, if the triplet is situated at the C-terminus of the sequence motif. However, in preferred embodiments, the sequence motif does not comprise such triplet block of amino acids of the first group at all, i.e. does not comprise a block consisting of 3 amino acids selected from the first group.

It is understood that the positional requirements alone, pairwise together with a further amino acid selected from the first group, and in a block with 2 further amino acids selected from the first group are not overlapping and the terms are mutual exclusive (e.g. a triplet is not a case of "alone" and/or "pairwise together", etc.).

A further positional requirement for the amino acids selected from the first group is, that the sequence motif must comprise at least 2 pairs of amino acids selected from the first group. However, it is preferred that not all amino acids selected from the first group are arranged pairwise in the sequence motif.

The sequence motif of the inventive polypeptide does not comprise blocks of 4 (quartet) or more amino acids (quintet, sextet, etc.) selected from the first group (i.e. an amino acid of the first group does not occur in a block with 3 or more amino acids selected from the first group). The sequence motif may thus for example not comprise sequences such as "KRKK" (SEQ ID NO: 8) or "RRRR" (SEQ ID NO: 9).

As amino acids of the first group make up only 40% to 60% of the sequence motif, the remaining amino acids need to be selected from other amino acid residues. As set out above, the sequence motif comprises also at least 40% and at most 60% amino acids selected from a second group of amino acids. Said second group consists of the amino acid residues alanine, glycine, isoleucine, leucine, phenylalanine, serine, threonine, tryptophan, tyrosine and valine. As before for the first group of amino acids, each of the amino acids of the second group is likewise in principle selected independently, i.e. each amino acid is selected independent from any previous or subsequent selections from said second group.

However, for the second group there are some restrictions to this general principle of independent selection. The first restriction applies, if the sum of amino acids selected from the first group and selected from the second group yields 100% of the amino acids of the sequence motif (i.e. there are no amino acids from the third group in the sequence motif). In such scenario at least three different amino acids must be selected from the second group. In such scenario the amino acids of the second group may for example not be restricted to valine and tryptophan residues only.

A further (positional) restriction is that the sequence motif may not comprise the triplet sequence AFV (alanine, phenylalanine, valine), if the sequence motif contains at least two single, non-adjacent phenylalanine residues and at least one of these phenylalanine residues is (N-terminally) directly preceded by a lysine residue (i.e. KF). Nonadjacent phenylalanine residues are phenylalanine residues which do not occur in a row in the sequence, but which are separated by one or more other amino acids. Single phenylalanine residues means that they are not part of a pair of phenylalanine residues or of a block of several phenylalanine residues but are positioned alone in the sequence motif.

The next restriction is, that the sequence motif does not comprise the sequence AALTH (i.e. alanine, alanine, lysine, threonine, histidine), if the sequence motif contains at least three single, non-adjacent histidine residues. Nonadjacent histidine residues are histidine residues which do not occur in a row, but which are separated by one or more other amino acids. Single histidine residues means that they are not part of a pair of histidine residues or of a block of several histidine residues but are positioned alone in the sequence motif.

In a preferred embodiment, less than 5 isoleucine residues (e.g. 4, 3, 2, 1 or 0) are selected from said second group, in particular if the polypeptide does not comprise the sequence of a peptidoglycan hydrolase and/or is of short length, e.g. has a length in the range of 16 to 50 amino acids.

It is possible, that the sequence motif of the polypeptide of the invention is not exclusively composed of amino acids selected from the first and second group (i.e. they represent together less than 100%). In such scenario, the remaining amino acids of said sequence motif are selected from a third group of amino acids, said group consisting of asparagine, aspartic acid, glutamine, glutamic acid, methionine, and cysteine. As before for the first and second group of amino acids, each of the amino acids of the third group is likewise in principle selected independently, i.e. each amino acid is selected independent from any previous or subsequent selections from said second group. However, as before for the second group, there are some restrictions to the selection of an amino acid from said third group: glutamine may be selected only once and a selection of glutamine and glutamic acid in parallel is also not allowed, i.e. if glutamine is present in the sequence motif, then no glutamic acid may be present and vice versa). Preferably, the amino acids selected from the third group are limited to asparagine, aspartic acid, glutamine and glutamic acid, i.e. the selected third group amino acids do not comprise methionine or cysteine residues.

In preferred embodiments, the sequence motif comprises only a single, or even more preferred no amino acid residue at all from the third group.

In preferred embodiments of the present invention, the arrangement of the selected amino acids in the sequence motif complies with the requirements set out in one of the possible sequence motif alternatives depicted in FIG. 1 (and FIGS. 2a, 2b, 2c, 2d and 2e, respectively). FIG. 1 specifies that at specific positions for a given 16mer, 17mer, 18mer, 19mer or 20mer no amino acids selected from the first group may be present. At these positions only amino acids selected from the second and/or the third group (if any) may be present. Preferably, amino acids of the second group are present at said positions. Amino acids of the first group may only be present at any of the remaining positions of the sequence motif. This does not imply that at these remaining positions only amino acids of the first group may be found. Amino acids of the second and optionally third group may also be found at these remaining positions, provided the overall percentage requirements for the first and second group are still met.

Preferably, the sequence motif of the inventive polypeptide is of helical structure.

The sequence motif of the inventive polypeptide does not comprise any other amino acid residues than those defined to be in the first, second or third group. In particular, the sequence motif of the inventive polypeptide does not comprise any proline residue, and if the third group is limited to asparagine, aspartic acid, glutamine and glutamic acid, no methionine and cysteine as well.

However, just as in the SMAP-29 sequence, a proline residue may very well be present in the inventive polypeptide. It is for example preferred, if a proline residue is located within 1 to 10, preferably 1 to 5 amino acid residues N-terminal or C-terminal of the sequence motif, with the latter being preferred. In cases where the inventive polypeptide comprises also the sequence of a peptidoglycan hydrolase (see below), it is preferred if such proline residue is found between the sequence of the peptidoglycan hydrolase and the sequence motif. Preferably, the sequence motif is N-terminal of the sequence of the peptidoglycan hydrolase and the proline residue is positioned somewhere in between, usually close to the sequence motif.

A polypeptide according to the present invention does not comprise the sequence of SEQ ID NO:1. In some embodiments, the polypeptide according to the present invention may comprise SEQ ID NO: 10. However, in preferred embodiments the polypeptide according to the present invention does not comprise the sequence of SEQ ID NO: 10 either.

The polypeptide according to the present invention is preferably an artificial polypeptide which does not occur in nature. Examples for such artificially constructed sequences are SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22 and SEQ ID NO: 23. Other examples are SEQ ID NO:71, SEQ ID NO:72, SEQ ID NO:73 and SEQ ID NO:74 Particularly preferred examples of polypeptides according to the present invention are thus polypeptides comprising any of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO:71, SEQ ID NO:72, SEQ ID NO:73 or SEQ ID NO:74.

In preferred embodiments, the polypeptide according to the present invention comprises additionally the sequence of a peptidoglycan hydrolase. Such polypeptide (representing a fusion protein of the present invention) comprises:

a) the sequence of a peptidoglycan hydrolase, and
b) a peptide sequence, said peptide sequence being preferably heterologous to the peptidoglycan hydrolase, and wherein said (heterologous) peptide sequence comprises a sequence motif which:
i) is 16, 17, 18, 19 or 20 amino acids in length;
ii) comprises at least 40% and at most 60% amino acids selected from a first group of amino acids consisting of lysine, arginine and histidine;
wherein each amino acid is selected independently from said first group;
wherein each amino acid selected from this first group is arranged in said sequence motif either alone, pairwise together with a further amino acid selected from the first group, or in a block with 2 further amino acids selected from the first group, but does not occur in a block with 3 or more amino acids selected from the first group, wherein at least 2 pairs of amino acids selected from the first group are present in said sequence motif, and wherein at most one block with 3 of the amino acids selected from the first group in a row is present in said sequence motif, with the additional proviso, that if such block with 3 amino acids of the first group is present in said sequence motif, then the amino acids at positions −12, −11, −8, −5, −4, +6, +7, +10, +13, and +14 relative to the first amino acid of the 3 amino acid block are, provided the respective position may be found in said sequence motif, not selected from said first group,
iii) comprises at least 40% and at most 60% amino acids selected from a second group of amino acids consisting of alanine, glycine, isoleucine, leucine, phenylalanine, serine, threonine, tryptophan, tyrosine and valine,
wherein each amino acid is selected independently from said second group,
wherein at least three different amino acids are selected from this second group, if the sum of amino acids of selected from the first group and selected from the second group yield 100% of the sequence motif;
wherein the sequence motif does not comprise the sequence AFV, if the sequence motif contains at least two single, non-adjacent phenylalanine residues and at least one of these phenylalanine residues is directly preceded by a lysine residue, and
wherein the sequence motif does not comprise the sequence AALTH (SEQ ID NO:2), if the sequence motif contains at least three single, non-adjacent histidine residues, iv) wherein the remaining amino acids of said sequence motif, if any are present in the motif, are selected from a third group consisting of asparagine, aspartic acid, glutamine, glutamic acid, methionine, or cysteine, wherein each of said amino acids is selected independently from said third group, and wherein glutamine may be selected only once and wherein the selection may furthermore not comprise a combination of glutamine and glutamic acid, and c) wherein said fusion protein does not comprise the sequence of SEQ ID NO:1.

It is understood that features and characteristics of the sequence motif of the polypeptide of the invention, which have been explained in detail above, do apply likewise for the sequence motif of the (heterologous) peptide sequence.

The peptidoglycan hydrolase of the fusion protein of the invention may be any peptidoglycan hydrolase capable of degrading bacterial peptidoglycan. Such peptidoglycan hydrolase may be in terms of enzymatic activity for example an endopeptidase, N-acetyl-muramoyl-L-alanine-amidase (amidase), N-acetyl-muramidase, N-acetyl-glucosaminidase or lytic transglycosylase and is thus suitable for degrading the peptidoglycan of bacterial cell walls. Preferably, the peptidoglycan hydrolase degrades the peptidoglycan of Gram-negative bacteria, such as *K. pneumoniae, E. coli* or *P. aeruginosa*.

The peptidoglycan structure of a bacterial cell wall is overall largely conserved with minor modifications (Schleifer & Kandler 1972). Bacterial species have interpeptide bridges composed of different amino acids or may even lack an interpeptide bridge. In peptidoglycan structures lacking an interpeptide bridge a Diaminopimelic acid (DAP) or meso-Diaminopimelic acid (mDAP; an amino acid, representing an epsilon-carboxy derivative of lysine being a typical component of peptidoglycan) (Diaminopimelic acid is residue replaces the amino acid L-Lys and directly crosslinks to the terminal amino acid D-Ala of the opposite peptide chain. Thus, there are limited types of chemical bonds available that can be hydrolyzed by peptidoglycan hydrolases. The peptidoglycan hydrolases exhibit at least one enzyme domain having an enzymatic activity as listed above. In addition the peptidoglycan hydrolases contain in some cases at least one domain suitable for binding to the peptidoglycan and supporting the enzymatic activity of the peptidoglycan hydrolase. The binding domains are typically called cell-wall binding domains (CBD).

Examples of peptidoglycan hydrolases are vertebrate lysozymes (such as hen egg white lysozyme and human lysozyme), endolysins (e.g. KZ144 endolysin or Lys394 endolysin), Virion-associated peptidoglycan hydrolases (VAPGH), bacteriocins (e.g. lysostaphin) and autolysins. Most preferably, the peptidoglycan hydrolase of the fusion protein of the present invention is an endolysin. Most preferably, the peptidoglycan hydrolase is an endolysin. Particularly preferred peptidoglycan hydrolase sequences are listed as SEQ ID NO:24, SEQ ID NO:25, SEQ ID NO:26 and SEQ ID NO:27.

Peptidoglycan degrading activity on Gram-negative and Gram-positive bacteria can be measured by assays well known in the art, e.g. by muralytic assays in which the outer membrane of Gram-negative bacteria is permeabilized or removed (e.g. with chloroform) to allow the putative enzyme access to the peptidoglycan layer. If the enzyme is active, degradation of the peptidoglycan layer will lead to a drop of turbidity, which can be measured photometrically (see for example Briers et al., J. Biochem. Biophys Methods 70: 531-533, (2007) or Schmelcher et al., Bacteriophage endolysins as novel antimicrobials. Schmelcher M, Donovan D M, Loessner M J. Future Microbiol. 2012 October; 7(10):1147-7).

A fusion protein according to the present invention exhibits preferably likewise the activity of a peptidoglycan degrading enzyme, i.e. is capable of degrading bacterial peptidoglycan. Preferably, a fusion protein of the present invention will be capable of degrading the peptidoglycan of bacteria of Gram-negative bacteria, such as *K. pneumoniae, E. coli* or *P. aeruginosa*.

The peptide sequence comprising the sequence motif of the present invention is preferably heterologous to the peptidoglycan hydrolase sequence. The peptide sequence comprising the sequence motif of the present invention and the peptidoglycan hydrolase sequence do thus preferably not occur together in a naturally occurring polypeptide chain. Even more preferably, the sequence motif and the peptidoglycan hydrolase sequence do not occur together in a naturally occurring polypeptide chain.

In the fusion protein of the invention, the peptide sequence comprising the sequence motif of the present invention is preferably an artificial peptide sequence which does not occur in nature. Particularly preferred examples of heterologous peptides comprising a sequence motif according to the present invention are SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO:71, SEQ ID NO:72, SEQ ID NO:73 and SEQ ID NO:74.

In preferred embodiments of the fusion protein of the present invention, the (heterologous) peptide sequence (or the sequence motif) is linked to the peptidoglycan hydrolase sequence by additional intervening amino acid residues (linker) such as the amino acid residues glycine, serine and serine (Gly-Ser-Ser), glycine, alanine, glycine and alanine (Gly-Ala-Gly-Ala; SEQ ID NO:28), glycine, alanine, glycine, alanine, glycine, alanine, glycine and alanine (Gly-Ala-Gly-Ala-Gly-Ala-Gly-Ala; SEQ ID NO:29) or glycine, alanine, glycine, alanine, glycine, alanine, glycine, alanine, glycine, alanine, glycine and alanine (Gly-Ala-Gly-Ala-Gly-Ala-Gly-Ala-Gly-Ala-Gly-Ala; SEQ ID NO:30).

The polypeptide of the present invention, and in particular the fusion protein of the present invention, may of course comprise further amino acid sequence elements, e.g. one or more tags, e.g. a His-tag, Strep-tag, Avi-tag, Myc-tag, Gst-tag, JS-tag, cystein-tag, FLAG-tag or other tags known in the art, thioredoxin, maltose binding proteins (MBP) etc.

In this context, the inventive polypeptide may additional comprise a tag e.g. for purification. Preferred is a His$_6$-tag (SEQ ID NO: 31), preferably at the C-terminus and/or the N-terminus of the polypeptide according to the present invention. Said tag can be linked to the polypeptide by additional amino acid residues e.g. due to cloning reasons. Preferably said tag can be linked to the protein by at least 1, 2, 3, 4, 5, 6, 7, 8, 9 or 10 additional amino acid residues. In some embodiments said additional amino acid residues may not be recognized and/or cleaved by proteases. In other embodiments said additional amino acid residues are recognized and/or cleaved by proteases. In a preferred embodiment the inventive polypeptide comprises a His$_6$-tag at its C-terminus linked to the polypeptide by the additional amino acid residues lysine and glycine (Lys-Gly) or leucine and glutamic acid (Leu-Glu). In another preferred embodiment the inventive polypeptide comprises a His$_6$-tag at its N-terminus linked to the polypeptide by the additional amino acid residues lysine and glycine (Lys-Gly) or leucine and glutamic acid (Leu-Glu). In another preferred embodiment the polypeptide comprises a $His_6$-tag at its N- and C-terminus linked to the polypeptide by the additional amino acid residues lysine and glycine (Lys-Gly) or leucine and glutamic acid (Leu-Glu).

Particularly preferred fusion proteins of the present invention may comprise the sequence of SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, and SEQ ID NO:43. Another group of fusion proteins according to the present invention comprises SEQ ID NO:75, SEQ ID NO:76, SEQ ID NO:77 or SEQ ID NO:78.

A polypeptide according to the present invention can be produced by standard means known in the art, e.g. by recombinant expression of nucleic acids encoding the respective polypeptide in appropriate host cells. If the inventive polypeptide comprises for example additionally amino acid sequence stretches or tags etc., such fusion proteins may be produced by linking the required individual nucleic acid sequences using standard cloning techniques as described e.g. by Sambrook et al. 2001, Molecular Cloning: A Laboratory Manual. Such a polypeptide may be produced likewise with methods known in the art, e.g., in recombinant DNA expression systems. Relatively short polypeptides according to the invention, e.g. up to 50 amino acids in length, may for example also be produced by synthetic means.

III. Nucleic Acids, Vectors, Bacteriophages and Host Cells

The present invention does also relate to nucleic acids encoding one or more inventive polypeptides of the present invention. The inventive nucleic acid may take all forms conceivable for a nucleic acid. In particular the nucleic acids according to the present invention may be RNA, DNA or hybrids thereof. They may be single-stranded or double-stranded. The may have the size of small transcripts or of entire genomes, such as a bacteriophage genome. As used herein, a nucleic acid encoding one or more inventive polypeptides of the present invention may be a nucleic acid reflecting the sense strand. Likewise, the antisense strand is also encompassed. The nucleic acid may encompass a heterologous promotor for expression of the inventive polypeptide. Particularly preferred nucleic acids encode a fusion protein according to the present invention.

In a further aspect the present invention relates to a vector comprising a nucleic acid according to the present invention. Such vector may for example be an expression vector allowing for expression of an inventive polypeptide. Said expression may be constitutive or inducible. The vector may also be a cloning vector comprising the nucleic acid sequence of the current invention for cloning purposes.

The present invention does also relate to a bacteriophage comprising an inventive nucleic acid, in particular comprising an inventive nucleic acid encoding a fusion protein according to the present invention.

The present invention does also relate to (isolated) host cells comprising a polypeptide, nucleic acid, vector, or bacteriophage according to the present invention. The host cells may be selected in particular from the group consisting of bacterial cells and yeast cells. Where appropriate, other suitable host cells may be immortalized cell lines, e.g. of mammalian (in particular human) origin. Particularly preferred host cells comprise a fusion protein according to the present invention.

IV. Compositions

In a further aspect the present invention relates to a composition comprising a polypeptide according to the present invention, a nucleic acid according to the present invention, a vector according to the present invention, a bacteriophage according to the present invention and/or a host cell according to the present invention.

A particularly preferred composition of the present invention comprises a fusion protein according to the present invention. Other preferred compositions comprise a polypeptide according to the present invention and a peptidoglycan hydrolase.

A composition according to the present invention may be a pharmaceutical composition comprising a pharmaceutical acceptable diluent, excipient or carrier.

In an even further aspect the composition according to the present invention is a cosmetic composition. Several bacterial species can cause irritations on environmentally exposed surfaces of the patient's body such as the skin. In order to prevent such irritations or in order to eliminate minor manifestations of said bacterial pathogens, special cosmetic preparations may be employed, which comprise sufficient amounts of the inventive polypeptide, nucleic acid, vector, host cell and/or composition in order to achieve a comedolytic effect.

V. Kits

In a further aspect the present invention relates to a kit comprising a polypeptide according to the present invention, a nucleic acid according to the present invention, a vector according to the present invention, a bacteriophage according to the present invention and/or a host cell according to the present invention, and further comprising a peptidoglycan hydrolase, or a nucleic acid, vector, bacteriophages, and/or host cell encoding or comprising, respectively, such peptidoglycan hydrolase. Preferably, the kit comprises a polypeptide according to the present invention and/or a peptidoglycan hydrolase.

A particularly preferred kit of the present invention comprises a polypeptide according to the present invention, but not a fusion protein of the present invention, i.e. the polypeptide in the kit does not comprise the sequence of a peptidoglycan hydrolase.

In a further embodiment, the kit of the invention comprises at least one further antimicrobial agent, such as an antibiotic or an antimicrobial peptide.

VI. Uses

In a further aspect the present invention relates to a polypeptide according to the present invention, a nucleic acid according to the present invention, a vector according to the present invention, a bacteriophage according to the present invention, a host cell according to the present invention, and/or a composition according to the present invention for use in a method of treatment of the human or animal body by surgery or therapy or in diagnostic methods practiced on the human or animal body. In such scenarios the antibacterial activity of polypeptide of the present invention can be exploited, in particular if a fusion protein of the present invention is used.

Such method typically comprises administering to a subject an effective amount of an inventive polypeptide (e.g. a fusion protein of the invention), nucleic acid, vector, bacteriophage, host cell or a composition. The subject may for example be a human or an animal, with human subjects being more preferred. In particular, the inventive polypeptide, the inventive nucleic acid, the inventive vector, the inventive bacteriophage, the inventive host cell, and/or the inventive composition may be used in methods for the treatment or prevention of bacterial infections, such Gram-negative bacterial infections. Without being limited thereto, the method of treatment may comprise the treatment and/or prevention of infections of the skin, of soft tissues, the respiratory system, the lung, the digestive tract, the eye, the ear, the teeth, the nasopharynx, the mouth, the bones, the vagina, of wounds of bacteraemia and/or endocarditis.

The dosage and route of administration used in a method of treatment (or prophylaxis) according to the present invention depends on the specific disease/site of infection to be treated. The route of administration may be for example oral, topical, nasopharyngeal, parenteral, intravenous, rectal or any other route of administration.

For application of an inventive polypeptide (e.g. a fusion protein of the invention), nucleic acid, vector, bacteriophage, host cell or composition to a site of infection (or site endangered to be infected) a formulation may be used that protects the active compounds from environmental influences such as proteases, oxidation, immune response etc., until it reaches the site of infection. Therefore, the formulation may be capsule, dragee, pill, suppository, injectable solution or any other medical reasonable galenic formulation. Preferably, the galenic formulation may comprise suitable carriers, stabilizers, flavourings, buffers or other suitable reagents. For example, for topical application the formulation may be a lotion or plaster, for nasopharyngeal application the formulation may be saline solution to be applied via a spray to the nose.

Preferably, an inventive polypeptide (e.g. fusion protein), nucleic acid, vector, bacteriophage, host cell or composition is used in combination with other conventional antibacterial agents, such as antibiotics, lantibiotics, bacteriocins or endolysins, etc. The administration of the conventional antibacterial agent can occur prior to, concurrent with or subsequent to administration of the inventive polypeptide (e.g. fusion protein), nucleic acid, vector, bacteriophage, host cell or composition.

In a further aspect the present invention relates to the inventive polypeptide, nucleic acid, vector, bacteriophage, host cell or composition for use as diagnostic means in medical diagnostics, food diagnostics, feed diagnostics, or environmental diagnostics, in particular as a diagnostic means for the diagnostic of bacterial infection, in particular those caused by Gram-negative bacteria. In this respect the inventive polypeptide, nucleic acid, vector, host cell or composition may be used as a tool to specifically degrade the peptidoglycan of pathogenic bacteria, in particular of Gram-negative pathogenic bacteria. The degradation of the bacterial cells by the inventive polypeptide, nucleic acid, vector, host cell or composition can be supported by the addition of detergents like Triton X-100 or other additives which weaken the bacterial cell envelope like polymyxin B. Specific cell degradation is needed as an initial step for subsequent specific detection of bacteria using nucleic acid based methods like PCR, nucleic acid hybridization or NASBA (Nucleic Acid Sequence Based Amplification), immunological methods like IMS, immunofluorescence or ELISA techniques, or other methods relying on the cellular content of the bacterial cells like enzymatic assays using proteins specific for distinct bacterial groups or species (e.g. β-galactosidase for enterobacteria, coagulase for coagulase positive strains).

In a further aspect the present invention relates to the use of the inventive polypeptide, the inventive nucleic acid, the inventive vector, the inventive bacteriophage, the inventive host cell, and/or the inventive composition, as an antimicrobial in food, feed, or cosmetics, or use as disinfecting agent. They can be used in particular for the treatment or prevention of Gram-negative bacterial contamination of foodstuff, of food processing equipment, of food processing plants, of (inanimate) surfaces coming into contact with foodstuff (such as shelves and food deposit areas), of feedstuff, of feed processing equipment, of feed processing plants, of (inanimate) surfaces coming into contact with feedstuff (such as shelves and feed deposit areas), of medical devices, or of (inanimate) surfaces in hospitals, doctor's offices and other medical facilities.

BRIEF DESCRIPTION OF THE FIGURES

In the following a brief description of the appended figure will be given. The figure is intended to illustrate the present invention in more detail. However, it is not intended to limit the scope of the invention to these specific examples.

Figure 1:
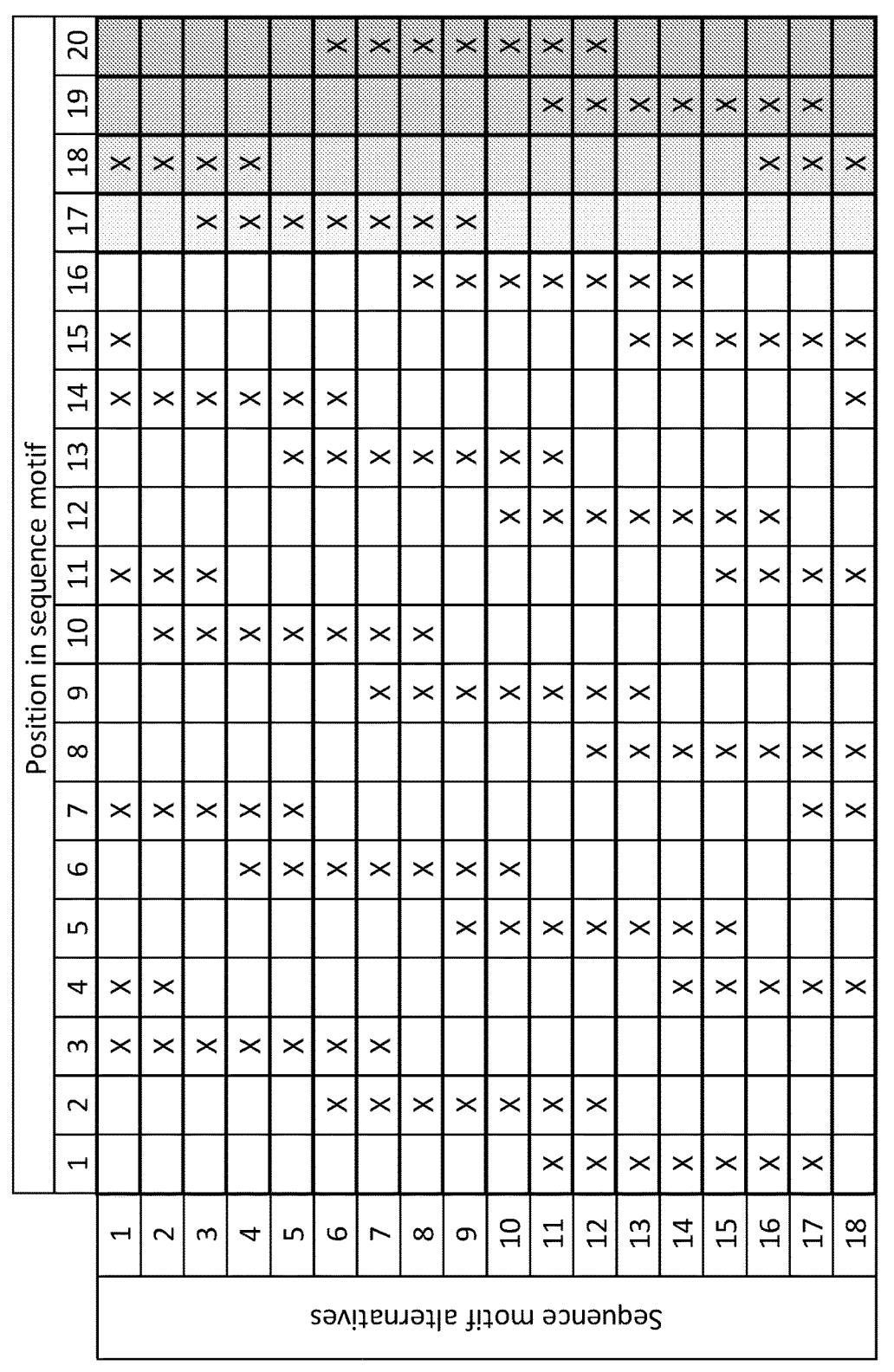

FIG. 1 illustrates positional requirements of preferred sequence motifs of the present invention. The table indicates for sequence motifs of 16 (white) to 20 (dark grey) amino acids in length positions at which no amino acid selected from the first group may be present (respective positions are labelled with "X"). At said positions (i.e. those labelled with "X"), only amino acids selected from the second, or as the case may be, from the third group may be present. More preferably, only amino acids selected from the second group are present at said positions. Amino acids selected from the first group of the sequence motif may only be present at positions which are not labelled with an "X". However, at said non-labelled positions, amino acids of the second, or as the case may be, third group may also be present. Altogether 18 alternatives, each for a length of 16, 17, 18, 19 or 20 amino acids are provided. The table also clearly specifies the position where potentially a triplet amino acid of the first group may be present (three positions in a row without "X"). For alternative 1 this would be positions 8 to 10. As required for a sequence motif of the polypeptide of the present invention, the amino acids at positions −5 (i.e. position #3), −4 (i.e. position #4), +6 (i.e. position #14), +7 (i.e. position #15), and +10 (i.e. position #18) relative to the first amino acid of the 3 amino acid block (i.e. position #8) are not to be selected from the first group. The relative positions −12, −11, −8, +13, and +14 cannot be found in the first alternative and are thus not taken into account.

Figure 2C:
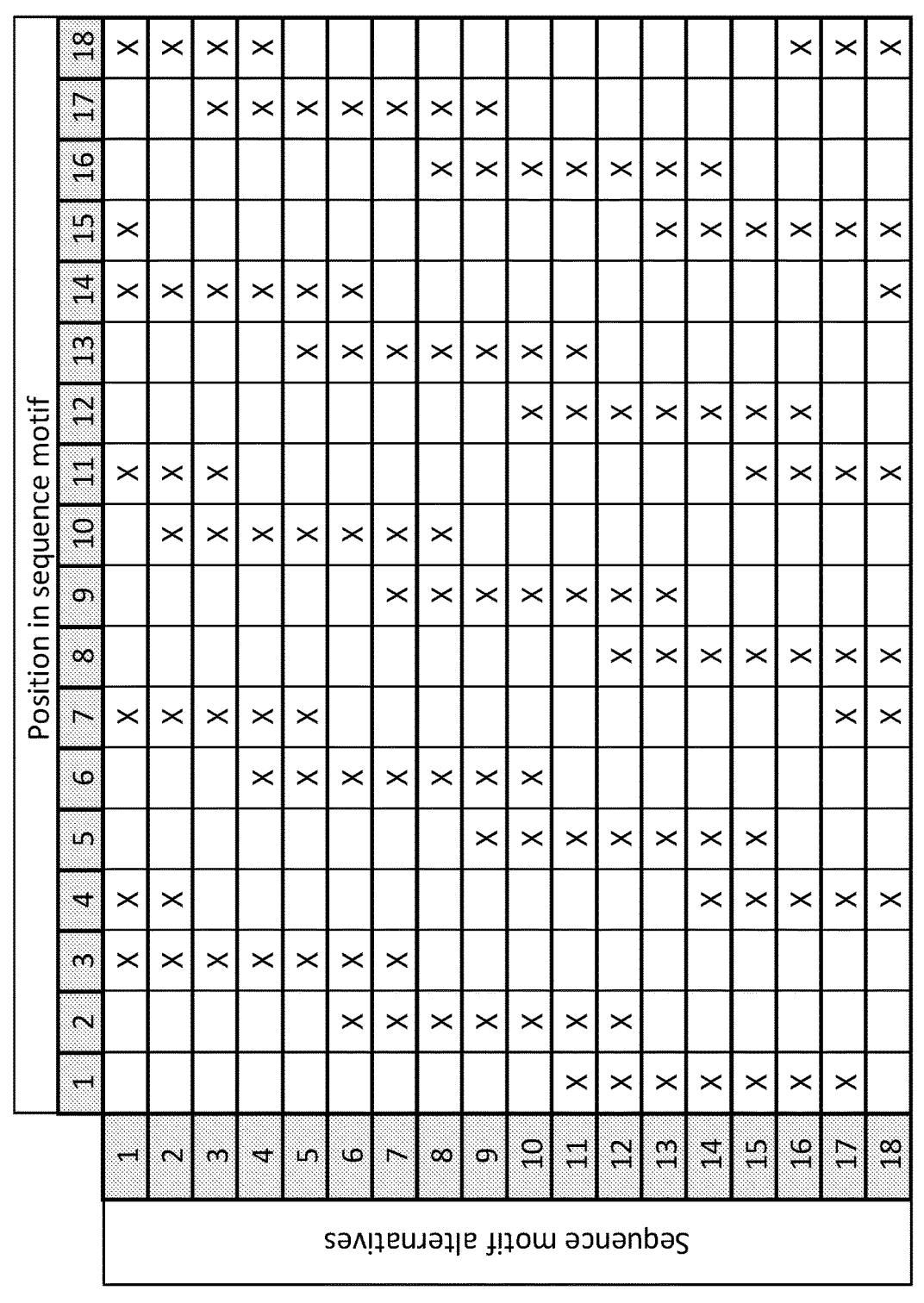
Figure 2E:
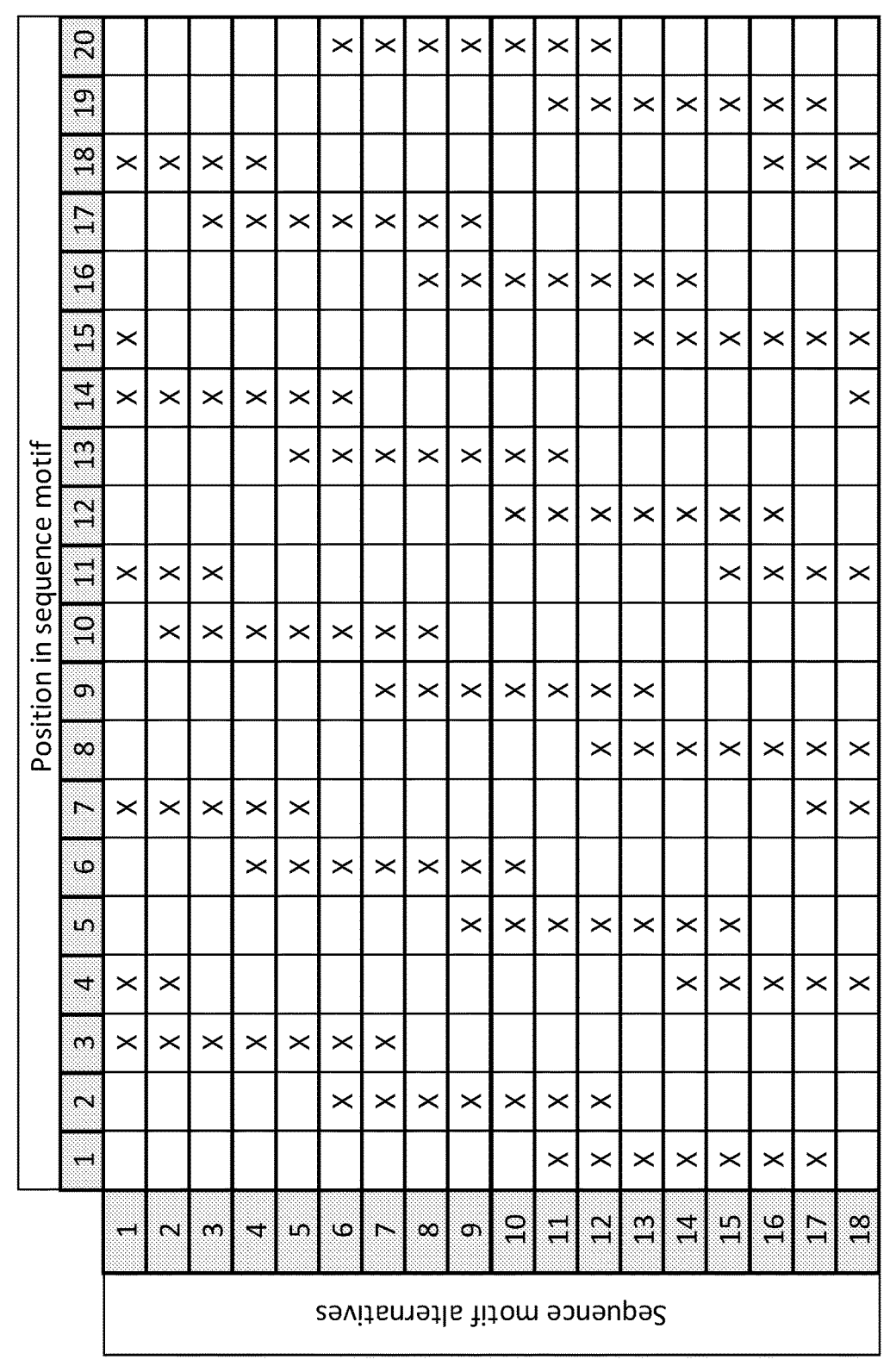

FIG. 2 illustrates in more detail the positional requirements of preferred sequence motifs. "X" denotes that the sequence motif does not exhibit at the respective position an amino acid selected from the first group. FIG. 2a: positional requirements for sequence motifs of 16 amino acids in length. FIG. 2b: positional requirements for sequence motifs of 17 amino acids in length. FIG. 2c: positional requirements for sequence motifs of 18 amino acids in length. FIG. 2d: positional requirements for sequence motifs of 19 amino acids in length. FIG. 2e: positional requirements for sequence motifs of 20 amino acids in length.

EXAMPLES

In the following, specific examples illustrating various embodiments and aspects of the invention are presented.

However, the present invention shall not to be limited in scope by the specific embodiments described herein. Indeed, various modifications of the invention in addition to those described herein will become readily apparent to those skilled in the art from the foregoing description, accompanying figure and the examples below. All such modifications fall within the scope of the appended claims.

Example 1: Adaption of the Antimicrobial Peptide Cecropin A (*A. aegypti*) to the Sequence Motif of the Present Invention Increases Antibacterial Activity The antimicrobial peptide Cecropin A (*A. aegypti*) (GGLKKLGKKLEGAGKRVFNAAEKALPVVAGAKA-LRK; SEQ ID NO:44) has been proposed in the art as candidate for fusions with, e.g., endolysins (see WO 2010/149792). However, a fusion of Cecropin A (*A. aegypti*) with KZ144 endolysin is not as effective against *P. aeruginosa* and *E. coli* bacteria as is a fusion of SMAP-29 peptide with KZ144. Furthermore, Cecropin A (*A. aegypti*) does not comply with the sequence motif of the present invention, as Cecropin A (*A. aegypti*) exhibits no sequence motif fulfilling the requirement, that at least 40% amino acids from the first group must be present. The inventor thus reasoned, that introduction of further amino acids of said group might increase antibacterial activity.

To test this hypothesis, the inventor fused Cecropin A (*A. aegypti*) to Lys394 endolysin, yielding a fusion protein comprising the sequence of SEQ ID NO:45. In parallel, a similar fusion protein was created, in which the Cecropin A (*A. aegypti*) peptide sequence was C-terminally truncated and mutated at various positions (peptide: GGLKKLG-KKLKKAGKRVFKAAKKAL; SEQ ID NO: 11) and fused to Lys394 endolysin. The resulting fusion protein comprises the sequence of SEQ ID NO:32. Due to introduction of additional lysine residues, the modified Cecropin A (*A. aegypti*) sequence now complied with the sequence motif of the present invention. Both fusion proteins were tested for their antibacterial activity towards *K. pneumoniae* bacteria.

Bacteria were grown in (Luria-Bertani) medium and diluted 1:10 in Mueller-Hinton medium. At optical density $OD_{600}$ of about 0.6 bacteria were diluted in the same medium 1:10 followed by a 1:500 dilution. Protein buffer (20 mM HEPES, 500 mM NaCl, pH 7.4) and proteins were pipetted into a 96 well plate, using different concentrations of proteins and an end volume of 20 µl including 500 µM EDTA final concentration. 180 µl of bacterial cells or a medium (Mueller-Hinton) control were given to the 96 well plate and mixed. The plate was incubated for 18-22 hours at 37° C. and the bacterial growth was determined measuring the OD600 values of the wells. The MIC which is the protein concentration of the well which showed the same OD600 value as the no-bacteria control was determined.

TABLE 1

Minimal inhibitory concentration of the tested fusion proteins

| Bacterial strain | Minimal inhibitory concentration (MIC; µg/ml) | |
|---|---|---|
| | SEQ ID NO: 45 | SEQ ID NO: 32 |
| *K. pneumoniae* ATCC 13883 | 25 | ≤5 |

The fusion of Cecropin A (*A. aegypti*) to Lys394 endolysin (SEQ ID NO:45) showed antibacterial activity, with a MIC of 25 µg/ml. For the fusion with the mutated Cecropin A (*A. aegypti*) sequence (SEQ ID NO:32) the MIC was much lower. ≤5 µg/ml means, that already at the (lowest) starting concentration no bacterial growth could be observed. Lower concentrations have not been tested, i.e. the actual MIC could be even lower than 5 µg/ml. Designing a Cecropin A (*A. aegypti*) variant complying with the sequence motif of the present invention thus improved the antibacterial activity of the original antimicrobial peptide.

Example 2: Improve in Antibacterial Activity is Independent of Endolysin Moiety

To test whether the increase in antibacterial activity is unique to the combination of peptide and endolysin utilized in example 1, the inventor tested the same peptides (i.e. SEQ ID NO: 11 and SEQ ID NO:44) in a fusion with another endolysin, OBPgpLys. The resulting polypeptides (SEQ ID NO:46 and SEQ ID NO:33) were tested essentially as described in example 1 but on *P. aeruginosa* PAO1 bacteria.

TABLE 2

Minimal inhibitory concentration of the tested fusion proteins

| Bacterial strain | Minimal inhibitory concentration (MIC; µg/ml) | |
|---|---|---|
| | SEQ ID NO: 46 | SEQ ID NO: 33 |
| *P. aeruginosa* PAO1 | 17.5 | 12.5 |

The fusion of cecropin A (*A. aegypti*) to OBPgpLys endolysin (SEQ ID NO:46) showed antibacterial activity, with a MIC of 17.5 µg/ml. For the fusion with the mutated cecropin A (*A. aegypti*) sequence (SEQ ID NO:33) the MIC was significantly lower (12.5 µg/ml). Hence, the improve in antibacterial activity is not dependent on the sequence of endolysin used.

Example 3: Adaption of the Peptide BMAP-28 to the Sequence Motif of the Present Invention Increases Antibacterial Activity BMAP-28, a bovine peptide of the cathelicidin family (GGLRSLGRKILRAWKKYGPIIVPIIRIG; SEQ ID NO: 47), was fused to a derivative of KZ144 endolysin (SEQ ID NO:25), yielding a fusion protein comprising SEQ ID NO:48. In parallel, a similar fusion protein was created, in which the peptide sequence of BMAP-28 was mutated at two positions (peptide: RGLRRLGRKILRAWKKYGPIIV-PIIRIG; SEQ ID NO: 12) and fused to the same derivative of KZ144 endolysin (fusion protein: SEQ ID NO:34). Due to introduction of two arginine amino acids in the N-terminal region of BMAP-28 peptide, said sequence now complied with the sequence motif of the present invention. Both fusion proteins were tested for their antibacterial activity on *E. coli* bacteria.

Bacteria were grown in (Luria-Bertani) medium and diluted 1:10 in Mueller-Hinton medium. At optical density $OD_{600}$ of about 0.6 bacteria were diluted in the same medium 1:10 followed by a 1:500 dilution. Protein buffer (20 mM HEPES, 500 mM NaCl, pH 7.4) and proteins were pipetted into a 96 well plate, using different concentrations of proteins and an end volume of 20 µl including 500 µM EDTA final concentration. 180 µl of bacterial cells or a medium (Mueller-Hinton) control were given to the 96 well plate and mixed. The plate was incubated for 18-22 hours at 37° C. and the bacterial growth was determined measuring the OD600 values of the wells. The MIC which is the protein concentration of the well which showed the same OD600 value as the no-bacteria control was determined.

TABLE 3

Minimal inhibitory concentration of the tested fusion proteins

| Bacterial strain | Minimal inhibitory concentration (MIC; µg/ml) | |
| --- | --- | --- |
| | SEQ ID NO: 48 | SEQ ID NO: 34 |
| E. coli 03-07953 | >30 | 10 |

">30" means, that for the non-mutated fusion protein with the original BMAP-28 peptide (SEQ ID NO:48) no antibacterial activity could be observed up to a concentration of 30 µg/ml. Antibacterial activity at higher concentrations is possible, but was not experimentally verified. In contrast, significant antibacterial activity was observed for the fusion protein with the mutated BMAP-28 peptide fragment, with a MIC of 10 µg/ml. This result emphasizes the importance of the sequence motif identified by the inventor and shows that designing respective polypeptides will facilitate generation of new antibacterial agents.

Example 4: The Type of Positively Charged Amino Acid in the Sequence Motif is Only of Little Significance In a further experiment the, inventor compared a fusion protein composed of the MSI 78 (4-20) fragment (KFLKKAKKFGKAFVKIL; SEQ ID NO:49) and Lys394 endolysin (fusion protein with SEQ ID NO:50) with a similar fusion protein, in which a modified MSI 78 (4-20) peptide (RFLRRARRFGRAFVRIL; SEQ ID NO: 13) was fused to Lys394 endolysin (fusion protein: SEQ ID NO:35). In the modified MSI 78 (4-20) peptide (SEQ ID NO: 13) the lysine residues of the MSI 78 (4-20) peptide have been substituted with arginine residues. Both fusion proteins were tested for their antibacterial activity on E. coli bacteria.

Bacteria were grown in (Luria-Bertani) medium and diluted 1:10 in Mueller-Hinton medium. At optical density $OD_{600}$ of about 0.6 bacteria were diluted in the same medium 1:10 followed by a 1:500 dilution. Protein buffer (20 mM HEPES, 500 mM NaCl, pH 7.4) and proteins were pipetted into a 96 well plate, using different concentrations of proteins and an end volume of 20 µl including 500 µM EDTA final concentration. 180 µl of bacterial cells or a medium (Mueller-Hinton) control were given to the 96 well plate and mixed. The plate was incubated for 18-22 hours at 37° C. and the bacterial growth was determined measuring the OD600 values of the wells. The MIC which is the protein concentration of the well which showed the same OD600 value as the no-bacteria control was determined.

TABLE 4

Minimal inhibitory concentration of the tested fusion proteins

| Bacterial strain | Minimal inhibitory concentration (MIC; µg/ml) | |
| --- | --- | --- |
| | SEQ ID NO: 50 | SEQ ID NO: 35 |
| E. coli 03-07953 | 10.2 | 6 |

Both fusion proteins showed antibacterial activity in essentially the same range. Thus, the type of positively charged amino acid selected from the first group in the sequence motif of the invention (e.g. K or R) is of minor importance.

Example 5: Adaption of the Peptide Magainin to the Sequence Motif of the Present Invention Improves Antibacterial Activity Magainin, an antimicrobial peptide from Xenopus laevis (GIGKFLHSAKKFGKAFVGEIMNS; SEQ ID NO:51), was fused to Lys394 endolysin (SEQ ID NO:24), yielding a fusion protein comprising SEQ ID NO:52. In parallel, a similar fusion protein was created. The peptide sequence of magainin was truncated and coupled with a linker (peptide: GIKKFLKSAKKFGKAFKKVIRGGGGS; SEQ ID NO: 14). Said peptide sequence was fused to Lys394 endolysin (fusion protein: SEQ ID NO:36). Both fusion proteins were tested for their antibacterial activity on P. aeruginosa PAO1 bacteria as described in example 2.

TABLE 5

Minimal inhibitory concentration of the tested fusion proteins

| Bacterial strain | Minimal inhibitory concentration (MIC; µg/ml) | |
| --- | --- | --- |
| | SEQ ID NO: 52 | SEQ ID NO: 36 |
| P. aeruginosa PAO1 | >30 | ≤5 |

">30" means again, that for the non-mutated fusion protein with the original magainin peptide (SEQ ID NO:52) no antibacterial activity could be observed up to a concentration of 30 µg/ml. Antibacterial activity at higher concentrations is possible, but was not experimentally verified. In contrast, significant antibacterial activity was observed for the fusion protein with the mutated magainin peptide fragment, with a MIC of ≤5 µg/ml.

Example 6: Adaption of the Peptide HPA-NT3 to the Sequence Motif of the Present Invention Increases Antibacterial Activity HPA-NT3, a Helicobacter pylori-derived peptide (FKRLKKLFKKIWNWK; SEQ ID NO:53), was fused to a derivative of KZ144 endolysin (SEQ ID NO:25), yielding a fusion protein comprising SEQ ID NO:54. In parallel, a similar fusion protein was created, in which the peptide sequence of HPA-NT3 was adapted to the sequence motif of the present invention (peptide: KRLKKLAKKIWKWGRRGPGS; SEQ ID NO: 15) and fused to the same derivative of KZ144 endolysin (fusion protein: SEQ ID NO:37). Both fusion proteins were tested for their antibacterial activity on P. aeruginosa PAO1 bacteria as described in example 2.

TABLE 6

Minimal inhibitory concentration of the tested fusion proteins

| Bacterial strain | Minimal inhibitory concentration (MIC; μg/ml) | |
| --- | --- | --- |
| | SEQ ID NO: 54 | SEQ ID NO: 37 |
| P. aeruginosa PAO1 | >18 | 12.5 |

">18" means, that for the non-mutated fusion protein with the original HPA-NT3 peptide (SEQ ID NO:54) no antibacterial activity could be observed up to a concentration of 18 μg/ml. Antibacterial activity at higher concentrations is possible, but was not experimentally verified. In contrast, antibacterial activity was observed for the fusion protein with the mutated HPA-NT3 peptide (SEQ ID NO: 15), with a MIC of 12.5 μg/ml. Adapting the antimicrobial peptide to the motif of the present invention thus increased antibacterial activity of the fusion protein.

Example 7: De Novo Generation of an Artificial Antimicrobial Peptide Starting from a Sequence Motif of Stonustoxin In an attempt to further verify suitability of the identified sequence motif, the inventor tried to render a peptide sequence previously not known for any antimicrobial activity into a useful peptide sequence for fusion with an endolysin. For this purpose, the inventor relied on amino acids 298-326 of the alpha subunit of stonustoxin (IPLIHDKIS-NFQQIFQDYMLTVQKKIAEK; SEQ ID NO:55). Stonustoxin is a component of the reef stonefish venom. Effects of the venom include severe pain, shock, paralysis, and tissue death. Antimicrobial activities are however not known.

SEQ ID NO:55 was fused to a derivative of KZ144 endolysin, yielding a fusion protein comprising SEQ ID NO:56. In parallel, a similar fusion protein was created, in which the stone fish sequence was mutated at various positions (peptide: IKLIKRVIKKFKKIFRKYPLTVKK-GIAVG; SEQ ID NO: 16) and fused to the same derivative of KZ144 endolysin (fusion protein: SEQ ID NO:38). Due to exchange of several amino acids in the stone fish sequence, the first 18 amino acids of said sequence now complied with the sequence motif of the present invention. In particular, the percentage of positively charged amino acids in said sequence motif has been increased (with lysine and arginine residues) and the proline residue removed. Both fusion proteins were tested for their antibacterial activity on P. aeruginosa bacteria.

Bacteria were grown in (Luria-Bertani) medium and diluted 1:10 in Mueller-Hinton medium. At optical density $OD_{600}$ of about 0.6 bacteria were diluted in the same medium 1:10 followed by a 1:500 dilution. Protein buffer (20 mM HEPES, 500 mM NaCl, pH 7.4) and proteins were pipetted into a 96 well plate, using different concentrations of proteins and an end volume of 20 μl including 500 μM EDTA final concentration. 180 μl of bacterial cells or a medium (Mueller-Hinton) control were given to the 96 well plate and mixed. The plate was incubated for 18-22 hours at 37° C. and the bacterial growth was determined measuring the OD600 values of the wells. The MIC which is the protein concentration of the well which showed the same OD600 value as the no-bacteria control was determined.

TABLE 7

Minimal inhibitory concentration of the tested fusion proteins

| Bacterial strain | Minimal inhibitory concentration (MIC; μg/ml) | |
| --- | --- | --- |
| | SEQ ID NO: 56 | SEQ ID NO: 38 |
| P. aeruginosa PAO1 | >91 | 17 |

>91 means, that for the non-mutated fusion protein (SEQ ID NO:56) with the original stonustoxin peptide (SEQ ID NO:55) no antibacterial activity could be observed up to a concentration of 91 μg/ml. Antibacterial activity at higher concentrations cannot be ruled out, but was not tested. This is as expected, because the stonustoxin fragment used in said fusion is not known for any antimicrobial activity and KZ144 endolysin alone is in principle inactive on P. aeruginosa. In contrast, unexpected de novo antibacterial activity was observed for the fusion protein with the mutated stonustoxin peptide fragment, with a MIC as low as 17. This result emphasizes the importance of the sequence motif identified by the inventor and shows that designing respective polypeptides will facilitate generation of new antibacterial agents.

Example 8: De Novo Generation of an Artificial Antimicrobial Peptide Starting from a Sequence Motif of CagL Protein The inventor created two further de novo antimicrobial peptides on basis of amino acids 26-48 of the CagL protein of Helicobacter pylori (GLKQLDSTYQETN-QQVLKNLDE; SEQ ID NO:57). CagL protein is specialized adhesin of Helicobacter pylori that is targeted to the pilus surface, where it binds to integrin α5β1 and mediates receptor-dependent delivery of CagA protein into gastric epithelial cells. An antimicrobial activity has not been reported.

SEQ ID NO:57 was fused to a derivative of KZ144 endolysin, yielding a fusion protein comprising SEQ ID NO:58. In parallel, two similar fusion proteins were created, in which the CagL sequence was mutated at various positions (peptide1: GLKKLKRVYRKWVKAVKKVLKL- GG GGS; SEQ ID NO: 17, including a C-terminal linker; peptide2: GLKVLKKAYRRIRKAVRKILKA; SEQ ID NO: 18) to conform with the motif of the present invention. The peptides were fused to the same derivative of KZ144 endolysin (fusion proteins: SEQ ID NO:39 and SEQ ID NO:40). Both fusion proteins were tested for their antibacterial activity on P. aeruginosa bacteria as described in example 2.

TABLE 8

Minimal inhibitory concentration of the tested fusion proteins

| Bacterial strain | Minimal inhibitory concentration (MIC; μg/ml) | | |
| --- | --- | --- | --- |
| | SEQ ID NO: 58 | SEQ ID NO: 39 | SEQ ID NO: 40 |
| P. aeruginosa PAO1 | >90 | 12.5 | 15 |

>90 means, that for the non-mutated fusion protein (SEQ ID NO:58) with the original CagL peptide (SEQ ID NO:57) no antibacterial activity could be observed up to a concentration of 90 μg/ml. This is as expected, because the CagL fragment used in said fusion is not known for any antimicrobial activity and KZ144 endolysin alone is inactive on P. aeruginosa. In contrast, unexpected de novo antibacterial activity was observed for both fusion proteins with the mutated CagL peptide fragment, with a MIC as low as 12.5 and 15 μg/ml.

Example 9: De Novo Generation of an Artificial Antimicrobial Peptide Starting from a Sequence Motif of IE1 Protein The next de novo antimicrobial peptide was created on basis of amino acids 178-198 of IE1 protein (YKEKFMVCLKQIVQYAVNS; SEQ ID NO:59). IE1 derives from human cytomegalovirus and antimicrobial activities are not known.

SEQ ID NO:59 was fused again to the derivative of KZ144 endolysin, yielding a fusion protein comprising SEQ ID NO:60. In parallel, a fusion protein was created, in which the IE1 sequence was mutated at various positions (peptide: YKRAFKKVLKRIRRYAKRS; SEQ ID NO: 19) and fused to the same derivative of KZ144 endolysin (fusion protein: SEQ ID NO:41). Both fusion proteins were tested for their antibacterial activity on *P. aeruginosa* bacteria as described in example 2.

TABLE 9

Minimal inhibitory concentration of the tested fusion proteins

| | Minimal inhibitory concentration (MIC; μg/ml) | |
|---|---|---|
| Bacterial strain | SEQ ID NO: 60 | SEQ ID NO: 41 |
| *P. aeruginosa* PAO1 | >30 | 15-20 |

>30 means, that for the non-mutated fusion protein (SEQ ID NO:60) with the original IE1 peptide (SEQ ID NO:59) no antibacterial activity could be observed up to a concentration of 30 pig/ml. Antibacterial activity at higher concentrations cannot be ruled out, but was not tested and would not be expected, because the IE1 fragment used in said fusion is not known for any antimicrobial activity. In contrast, unexpected de novo antibacterial activity was observed for the fusion protein with the mutated IE1 peptide fragment, with a MIC between 15 and 20 μg/ml.

Example 10: Generation of a Further Fusion Protein Comprising a Peptide with a Sequence Motif of the Present Invention The inventor created also a further fusion protein comprising the sequence of SEQ ID NO:42. Said fusion protein comprises a peptide conforming with the present invention (SEQ ID NO: 20). The fusion protein was tested for antibacterial activity on *P. aeruginosa* bacteria as reported in example 2.

TABLE 10

Minimal inhibitory concentration of the tested fusion protein

| Bacterial strain | Minimal inhibitory concentration (MIC; μg/ml) SEQ ID NO: 42 |
|---|---|
| *P. aeruginosa* PAO1 | ≤5 |

Significant antibacterial activity was observed for the fusion protein with the novel peptide, with a MIC of ≤5 μg/ml.

Example 11: Generation of a Further Variations of a Fusion Protein Comprising a Peptide with a Sequence Motif of the Present Invention The inventor created further fusion proteins comprising a peptide conforming with the motif of the present invention (SEQ ID NO:61, SEQ ID NO:62, SEQ ID NO:63, SEQ ID NO:64, SEQ ID NO:65, SEQ ID NO:66, SEQ ID NO:67, SEQ ID NO:68). The fusion proteins were tested for antibacterial activity on *E. coli* bacteria.

TABLE 11

Minimal inhibitory concentration of the tested fusion protein

| | Minimal inhibitory concentration (MIC; μg/ml) | | | |
|---|---|---|---|---|
| Bacterial strain | SEQ ID NO: 61 | SEQ ID NO: 62 | SEQ ID NO: 63 | SEQ ID NO: 64 |
| *E. coli* DSMZ 11753 | ≤5 | ≤5 | ≤5 | ≤5 |
| Bacterial strain | SEQ ID NO: 65 | SEQ ID NO: 66 | SEQ ID NO: 67 | SEQ ID NO: 68 |
| *E. coli* DSMZ 11753 | ≤5 | 7.5 | ≤5 | ≤5 |

Antibacterial activity was observed for all fusion proteins.

Example 12: Adaption of Peptide MW2 of Briers et al. To Sequence Motif of the Present Invention Briers et al. (MBio. 2014; 5(4):e01379-14) reported creation of various fusion proteins, including inter alia peptide MW2 (SEQ ID NO:69). Said peptide does not comply with the sequence motif of the present invention. Starting from this peptide the inventor created a fusion protein comprising said peptide and the derivative of KZ144 endolysin (SEQ ID NO:25), resulting in a fusion protein according to SEQ ID NO:70. In addition, the inventor created a number of derivatives of the peptide of SEQ ID NO:69 (SEQ ID NO:71, SEQ ID NO:72, SEQ ID NO:73, and SEQ ID NO:74). These derivatives match the sequence motif of the present invention, while MW2 does not. The resulting fusion proteins are provided in SEQ ID NO:75, SEQ ID NO:76, SEQ ID NO:77, and SEQ ID NO:78. The fusion proteins were tested for antibacterial activity on *P. aeruginosa* PAO1 bacteria as described in example 2.

TABLE 12

Minimal inhibitory concentration of the tested fusion protein

| | Minimal inhibitory concentration (MIC; μg/ml) | | | | |
|---|---|---|---|---|---|
| Bacterial strain | SEQ ID NO: 70 | SEQ ID NO: 75 | SEQ ID NO: 76 | SEQ ID NO: 77 | SEQ ID NO: 78 |
| *P. aeruginosa* PAO1 | >30 | 10 | 10 | 25 | 20 |

Antibacterial activity was observed for all fusion proteins. Noteworthy, the fusion proteins on basis of the four derivatives of MW2 peptide (i.e. adapted to the sequence motif of the present invention) yielded improved antibacterial activity as compared to the fusion protein with the "wildtype" MW2 peptide.

Example 13: Use of the Peptide Magainin in Combination with a Further Peptidoglycan Hydrolase The inventor also combined the two peptides of example 5 with a further peptidoglycan hydrolase, namely a tail baseplate protein of Vibrio phage ICP1 (SEQ ID NO:27). The resultant fusion proteins comprise the sequences of SEQ ID NO:79 and SEQ ID NO:43. The fusion proteins were tested for antibacterial activity on *E. coli* bacteria.

TABLE 13

Minimal inhibitory concentration of the tested fusion proteins

| Bacterial strain | Minimal inhibitory concentration (MIC; µg/ml) | |
| --- | --- | --- |
| | SEQ ID NO: 79 | SEQ ID NO: 43 |
| *E. coli* DSMZ 11753 | 1 | ≤0.5 |

The resulting fusion proteins exhibited both antibacterial activity. The peptide complying with the sequence motif of the present invention (SEQ ID NO: 14) provided again better activity than the wild-type peptide (SEQ ID NO:51).

Example 14: Further Peptides

In a final set of experiments the inventor created three further fusion proteins, each comprising a endolysin sequence and a peptide complying with the sequence motif according to the present invention. The three peptides were SEQ ID NO: 21, SEQ ID NO: 22 and SEQ ID NO: 23. All three resulting fusion proteins showed excellent antibacterial activity.

The invention claimed is:

1. A fusion protein comprising the sequence of:
   a) a peptidoglycan hydrolase, and
   b) a peptide sequence heterologous to the peptidoglycan hydrolase, wherein said heterologous peptide sequence comprises a sequence motif comprising SEQ ID NO: 11.

2. The fusion protein of claim 1, wherein the peptidoglycan hydrolase is Lys394, KZ144, OBPgpLys endolysin or a tail baseplate protein of Vibrio phage ICP1.

3. The fusion protein of claim 1, wherein a proline residue is located in a flanking region of said sequence motif within 1 to 5 amino acid residues N-terminal or C-terminal of SEQ ID NO: 11.

4. The fusion protein according to claim 3, wherein said proline residue is located between the sequence of the peptidoglycan hydrolase and the sequence motif.

5. The fusion protein of claim 1, wherein the sequence motif is situated N-terminal of the sequence of the peptidoglycan hydrolase.

6. A polypeptide comprising the sequence of SEQ ID NO: 11.

7. A composition comprising a fusion protein according to claim 1.

8. The composition according to claim 7, wherein the composition is a pharmaceutical composition comprising a pharmaceutically acceptable diluent, excipient or carrier or wherein the composition is a cosmetic composition comprising an acceptable diluent, excipient or carrier.

9. A method of treating a gram negative bacterial infection in a human or animal comprising administering to said subject a fusion protein according to claim 1.

10. The method of claim 2, wherein the fusion protein comprises the sequence of SEQ ID NO:24, SEQ ID NO:25, SEQ ID NO:26 or SEQ ID NO:27.

* * * * *

SEQUENCE LISTING

```
<160> NUMBER OF SEQ ID NOS: 79

<210> SEQ ID NO 1
<211> LENGTH: 29
<212> TYPE: PRT
<213> ORGANISM: unknown
<220> FEATURE:
<223> OTHER INFORMATION: Synthetic amino acid (SMAP-29 sheep)

<400> SEQUENCE: 1

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
            20                  25

<210> SEQ ID NO 2
<211> LENGTH: 5
<212> TYPE: PRT
<213> ORGANISM: Artificial sequence
<220> FEATURE:
<223> OTHER INFORMATION: Synthetic peptide (sequence, which is not part
      of the sequence motif, if the sequence motif contains at least
      three non-adjacent histidine residues)

<400> SEQUENCE: 2

Ala Ala Leu Thr His
1               5

<210> SEQ ID NO 3
<211> LENGTH: 4
<212> TYPE: PRT
<213> ORGANISM: Artificial sequence
<220> FEATURE:
<223> OTHER INFORMATION: Synthetic amino acid (Example for
      intrasequential pairwise block of amino acids of the first group)

<400> SEQUENCE: 3

Leu Lys Arg Glu
```

<210> SEQ ID NO 4
<211> LENGTH: 5
<212> TYPE: PRT
<213> ORGANISM: Artificial sequence
<220> FEATURE:
<223> OTHER INFORMATION: Synthetic amino acid (Example for
      intrasequential triplet block of amino acids of the first group)

<400> SEQUENCE: 4

Leu Lys Arg Lys Glu
1               5

<210> SEQ ID NO 5
<211> LENGTH: 4
<212> TYPE: PRT
<213> ORGANISM: Artificial sequence
<220> FEATURE:
<223> OTHER INFORMATION: Synthetic amino acid (Example for N-terminal
      triplet block of amino acids of the first group)

<400> SEQUENCE: 5

Lys Arg Lys Glu
1

<210> SEQ ID NO 6
<211> LENGTH: 4
<212> TYPE: PRT
<213> ORGANISM: Artificial sequence
<220> FEATURE:
<223> OTHER INFORMATION: Synthetic amino acid (Example for C-terminal
      triplet block of amino acids of the first group)

<400> SEQUENCE: 6

Leu Lys Arg Lys
1

<210> SEQ ID NO 7
<211> LENGTH: 7
<212> TYPE: PRT
<213> ORGANISM: Artificial sequence
<220> FEATURE:
<223> OTHER INFORMATION: Synthetic amino acid (Example of a sequence
      precluded from the sequence motif, if a triplet of amnio acids of
      the first group is present)

<400> SEQUENCE: 7

Arg Arg Arg Gly Leu Arg His
1               5

<210> SEQ ID NO 8
<211> LENGTH: 4
<212> TYPE: PRT
<213> ORGANISM: Artificial sequence
<220> FEATURE:
<223> OTHER INFORMATION: Synthetic amino acid (Example of sequence not
      allowable within the sequence motif

<400> SEQUENCE: 8

Lys Arg Lys Lys
1

<210> SEQ ID NO 9
<211> LENGTH: 4
<212> TYPE: PRT
<213> ORGANISM: Artificial sequence
<220> FEATURE:

```
<223> OTHER INFORMATION: Synthetic amino acid (Example of sequence not
      allowable within the sequence motif)

<400> SEQUENCE: 9

Arg Arg Arg Arg
1

<210> SEQ ID NO 10
<211> LENGTH: 18
<212> TYPE: PRT
<213> ORGANISM: Unknown
<220> FEATURE:
<223> OTHER INFORMATION: Synthetic amino acid (SMAP-29 sheep;aa1-18

<400> SEQUENCE: 10

Arg Gly Leu Arg Arg Leu Gly Arg Lys Ile Ala His Gly Val Lys Lys
1               5                   10                  15

Tyr Gly

<210> SEQ ID NO 11
<211> LENGTH: 25
<212> TYPE: PRT
<213> ORGANISM: Artificial sequence
<220> FEATURE:
<223> OTHER INFORMATION: Synthetic amino acid (Mutated peptide deriving
      from Cecropin A (A. aegypti))

<400> SEQUENCE: 11

Gly Gly Leu Lys Lys Leu Gly Lys Lys Leu Lys Lys Ala Gly Lys Arg
1               5                   10                  15

Val Phe Lys Ala Ala Lys Lys Ala Leu
            20                  25

<210> SEQ ID NO 12
<211> LENGTH: 28
<212> TYPE: PRT
<213> ORGANISM: Artificial sequence
<220> FEATURE:
<223> OTHER INFORMATION: Synthetic amino acid (Mutated peptide deriving
      from BMAP-28)

<400> SEQUENCE: 12

Arg Gly Leu Arg Arg Leu Gly Arg Lys Ile Leu Arg Ala Trp Lys Lys
1               5                   10                  15

Tyr Gly Pro Ile Ile Val Pro Ile Ile Arg Ile Gly
            20                  25

<210> SEQ ID NO 13
<211> LENGTH: 17
<212> TYPE: PRT
<213> ORGANISM: Artificial Sequence
<220> FEATURE:
<223> OTHER INFORMATION: Synthetic amino acid (Mutated peptide deriving
      from MSI-78 (4-20) peptide

<400> SEQUENCE: 13

Arg Phe Leu Arg Arg Ala Arg Arg Phe Gly Arg Ala Phe Val Arg Ile
1               5                   10                  15

Leu

<210> SEQ ID NO 14
<211> LENGTH: 26
<212> TYPE: PRT
<213> ORGANISM: Artificial sequence
<220> FEATURE:
```

```
<223> OTHER INFORMATION: Synthetic amino acid (Mutated peptide deriving
      from magainin

<400> SEQUENCE: 14

Gly Ile Lys Lys Phe Leu Lys Ser Ala Lys Lys Phe Gly Lys Ala Phe
1               5                   10                  15

Lys Lys Val Ile Arg Gly Gly Gly Gly Ser
            20                  25

<210> SEQ ID NO 15
<211> LENGTH: 20
<212> TYPE: PRT
<213> ORGANISM: Artificial sequence
<220> FEATURE:
<223> OTHER INFORMATION: Synthetic amino acid (Mutated peptide deriving
      from HPA-NT3 peptide

<400> SEQUENCE: 15

Lys Arg Leu Lys Lys Leu Ala Lys Lys Ile Trp Lys Trp Gly Arg Arg
1               5                   10                  15

Gly Pro Gly Ser
            20

<210> SEQ ID NO 16
<211> LENGTH: 29
<212> TYPE: PRT
<213> ORGANISM: Artificial sequence
<220> FEATURE:
<223> OTHER INFORMATION: Synthetic amino acid (Mutated peptide deriving
      from amino acids 298-326 of the alpha subunit of stonustoxin

<400> SEQUENCE: 16

Ile Lys Leu Ile Lys Arg Val Ile Lys Lys Phe Lys Lys Ile Phe Arg
1               5                   10                  15

Lys Tyr Pro Leu Thr Val Lys Lys Gly Ile Ala Val Gly
            20                  25

<210> SEQ ID NO 17
<211> LENGTH: 27
<212> TYPE: PRT
<213> ORGANISM: Artificial sequence
<220> FEATURE:
<223> OTHER INFORMATION: Synthetic amino acid (Mutated peptide deriving
      from amino acids 26-48 of CagL protein

<400> SEQUENCE: 17

Gly Leu Lys Lys Leu Lys Arg Val Tyr Arg Lys Trp Val Lys Ala Val
1               5                   10                  15

Lys Lys Val Leu Lys Leu Gly Gly Gly Gly Ser
            20                  25

<210> SEQ ID NO 18
<211> LENGTH: 22
<212> TYPE: PRT
<213> ORGANISM: Artificial sequence
<220> FEATURE:
<223> OTHER INFORMATION: Synthetic amino acid (Mutated peptide deriving
      from amino acids 26-48 of CagL protein

<400> SEQUENCE: 18

Gly Leu Lys Val Leu Lys Lys Ala Tyr Arg Arg Ile Arg Lys Ala Val
1               5                   10                  15

Arg Lys Ile Leu Lys Ala
            20
```

<210> SEQ ID NO 19
<211> LENGTH: 19
<212> TYPE: PRT
<213> ORGANISM: Artificial sequence
<220> FEATURE:
<223> OTHER INFORMATION: Synthetic amino acid (Mutated peptide deriving from amino acids 178-198 of IE1 protein

<400> SEQUENCE: 19

Tyr Lys Arg Ala Phe Lys Lys Val Leu Lys Arg Ile Arg Arg Tyr Ala
1               5                   10                  15

Lys Arg Ser

<210> SEQ ID NO 20
<211> LENGTH: 24
<212> TYPE: PRT
<213> ORGANISM: Artificial sequence
<220> FEATURE:
<223> OTHER INFORMATION: Synthetic amino acid

<400> SEQUENCE: 20

Gly Phe Phe Lys Lys Ala Trp Arg Lys Val Lys His Ala Gly Arg Arg
1               5                   10                  15

Val Leu Lys Thr Ala Lys Gly Val
            20

<210> SEQ ID NO 21
<211> LENGTH: 20
<212> TYPE: PRT
<213> ORGANISM: unknown
<220> FEATURE:
<223> OTHER INFORMATION: Synthetic amino acid (CAP18AA

<400> SEQUENCE: 21

Gly Leu Arg Lys Ala Leu Arg Lys Phe Arg Asn Lys Ile Lys Glu Ala
1               5                   10                  15

Leu Lys Lys Ile
            20

<210> SEQ ID NO 22
<211> LENGTH: 20
<212> TYPE: PRT
<213> ORGANISM: artificial sequence
<220> FEATURE:
<223> OTHER INFORMATION: Synthetic amino acid

<400> SEQUENCE: 22

Gly Leu Arg Lys Ala Leu Arg Lys Phe Arg Lys Lys Ile Lys Glu Ala
1               5                   10                  15

Leu Lys Lys Ile
            20

<210> SEQ ID NO 23
<211> LENGTH: 29
<212> TYPE: PRT
<213> ORGANISM: artificial sequence
<220> FEATURE:
<223> OTHER INFORMATION: synthetic sequence

<400> SEQUENCE: 23

Arg Gly Leu Arg Arg Leu Gly Arg Lys Ile Ala Arg Gly Val Lys Lys
1               5                   10                  15

Tyr Gly Pro Thr Val Leu Arg Ile Ile Arg Ile Ala Gly
            20                  25

<210> SEQ ID NO 24
<211> LENGTH: 136
<212> TYPE: PRT
<213> ORGANISM: Unknown
<220> FEATURE:
<223> OTHER INFORMATION: Synthetic amino acid (S394 endolysin without
      N-terminal methionine)

<400> SEQUENCE: 24

Ser Phe Lys Phe Gly Lys Asn Ser Glu Lys Gln Leu Ala Thr Val Lys
1               5                   10                  15

Pro Glu Leu Gln Lys Val Ala Arg Arg Ala Leu Glu Leu Ser Pro Tyr
            20                  25                  30

Asp Phe Thr Ile Val Gln Gly Ile Arg Thr Val Ala Gln Ser Ala Gln
        35                  40                  45

Asn Ile Ala Asn Gly Thr Ser Phe Leu Lys Asp Pro Ser Lys Ser Lys
    50                  55                  60

His Val Thr Gly Asp Ala Ile Asp Phe Ala Pro Tyr Ile Asn Gly Lys
65                  70                  75                  80

Ile Asp Trp Lys Asp Leu Glu Ala Phe Trp Ala Val Lys Lys Ala Phe
                85                  90                  95

Glu Gln Ala Gly Lys Glu Leu Gly Ile Lys Leu Arg Phe Gly Ala Asp
            100                 105                 110

Trp Asn Ser Ser Gly Asp Tyr His Asp Glu Ile Asp Arg Gly Thr Tyr
        115                 120                 125

Asp Gly Gly His Val Glu Leu Val
    130                 135

<210> SEQ ID NO 25
<211> LENGTH: 259
<212> TYPE: PRT
<213> ORGANISM: artificial sequence
<220> FEATURE:
<223> OTHER INFORMATION: Synthetic amino acid (mutated KZ144 with C14S,
      C23S and C50S, without N-terminal methionine)

<400> SEQUENCE: 25

Lys Val Leu Arg Lys Gly Asp Arg Gly Asp Glu Val Ser Gln Leu Gln
1               5                   10                  15

Thr Leu Leu Asn Leu Ser Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Ser Leu Asp Ser Asp Gly Ile Val Gly Lys Asn Thr Trp Ala Glu Leu
    50                  55                  60

Phe Ser Lys Tyr Ser Pro Ile Pro Tyr Lys Thr Ile Pro Met Pro
65                  70                  75                  80

Thr Ala Asn Lys Ser Arg Ala Ala Ala Thr Pro Val Met Asn Ala Val
                85                  90                  95

Glu Asn Ala Thr Gly Val Arg Ser Gln Leu Leu Leu Thr Phe Ala Ser
            100                 105                 110

Ile Glu Ser Ala Phe Asp Tyr Glu Ile Lys Ala Lys Thr Ser Ser Ala
        115                 120                 125

Thr Gly Trp Phe Gln Phe Leu Thr Gly Thr Trp Lys Thr Met Ile Glu
    130                 135                 140

Asn Tyr Gly Met Lys Tyr Gly Val Leu Thr Asp Pro Thr Gly Ala Leu
145                 150                 155                 160

Arg Lys Asp Pro Arg Ile Ser Ala Leu Met Gly Ala Glu Leu Ile Lys
            165                 170                 175

Glu Asn Met Asn Ile Leu Arg Pro Val Leu Lys Arg Glu Pro Thr Asp
            180                 185                 190

Thr Asp Leu Tyr Leu Ala His Phe Phe Gly Pro Gly Ala Ala Arg Arg
            195                 200                 205

Phe Leu Thr Thr Gly Gln Asn Glu Leu Ala Ala Thr His Phe Pro Lys
            210                 215                 220

Glu Ala Gln Ala Asn Pro Ser Ile Phe Tyr Asn Lys Asp Gly Ser Pro
225                 230                 235                 240

Lys Thr Ile Gln Glu Val Tyr Asn Leu Met Asp Gly Lys Val Ala Ala
            245                 250                 255

His Arg Lys

<210> SEQ ID NO 26
<211> LENGTH: 327
<212> TYPE: PRT
<213> ORGANISM: unknown
<220> FEATURE:
<223> OTHER INFORMATION: Synthetic amino acid (OBPgpLYS fragment)

<400> SEQUENCE: 26

Lys Asn Ser Glu Lys Asn Ala Ser Ile Ile Met Ser Ile Gln Arg Thr
1               5                   10                  15

Leu Ala Ser Leu Ser Leu Tyr Gly Gly Arg Ile Asp Gly Leu Phe Gly
            20                  25                  30

Glu Lys Cys Arg Gly Ala Ile Ile Leu Met Leu Asn Lys Val Tyr Pro
        35                  40                  45

Asn Phe Ser Thr Asn Lys Leu Pro Ser Asn Thr Tyr Glu Ala Glu Ser
    50                  55                  60

Val Phe Thr Phe Leu Gln Thr Ala Leu Ala Gly Val Gly Leu Tyr Thr
65                  70                  75                  80

Ile Thr Ile Asp Gly Lys Trp Gly Gly Thr Ser Gln Gly Ala Ile Asp
            85                  90                  95

Ala Leu Val Lys Ser Tyr Arg Gln Ile Thr Glu Ala Glu Arg Ala Gly
            100                 105                 110

Ser Thr Leu Pro Leu Gly Leu Ala Thr Val Met Ser Lys His Met Ser
            115                 120                 125

Ile Glu Gln Leu Arg Ala Met Leu Pro Thr Asp Arg Gln Gly Tyr Ala
        130                 135                 140

Glu Val Tyr Ile Asp Pro Leu Asn Glu Thr Met Asp Ile Phe Glu Ile
145                 150                 155                 160

Asn Thr Pro Leu Arg Ile Ala His Phe Met Ala Gln Ile Leu His Glu
            165                 170                 175

Thr Ala Cys Phe Lys Tyr Thr Glu Glu Leu Ala Ser Gly Lys Ala Tyr
            180                 185                 190

Glu Gly Arg Ala Asp Leu Gly Asn Thr Arg Pro Gly Asp Gly Pro Leu
            195                 200                 205

Phe Lys Gly Arg Gly Leu Leu Gln Ile Thr Gly Arg Leu Asn Tyr Val
            210                 215                 220

Lys Cys Gln Val Tyr Leu Arg Glu Lys Leu Lys Asp Pro Thr Phe Asp
225                 230                 235                 240

Ile Thr Ser Ser Val Thr Cys Ala Gln Gln Leu Ser Glu Ser Pro Leu
            245                 250                 255

```
Leu Ala Ala Leu Ala Ser Gly Tyr Phe Trp Arg Phe Ile Lys Pro Lys
            260                 265                 270

Leu Asn Glu Thr Ala Asp Lys Asp Ile Tyr Trp Val Ser Val Tyr
            275                 280                 285

Val Asn Gly Tyr Ala Lys Gln Ala Asn Pro Tyr Tyr Pro Asn Arg Asp
290                 295                 300

Lys Glu Pro Asn His Met Lys Glu Arg Val Gln Met Leu Ala Val Thr
305                 310                 315                 320

Lys Lys Ala Leu Gly Ile Val
            325

<210> SEQ ID NO 27
<211> LENGTH: 237
<212> TYPE: PRT
<213> ORGANISM: unknown
<220> FEATURE:
<223> OTHER INFORMATION: Synthetic amino acid (Tail baseplate protein of
      Vibrio phage ICP1 without N-terminal methionine)

<400> SEQUENCE: 27

Ile Leu Lys Arg Gly Ser Ser Gly Ala Asp Val Lys Asn Met Gln Glu
1               5                   10                  15

Tyr Leu Thr Ala Leu Gly Tyr Asp Thr Lys Gly Val Glu Gly Thr Phe
            20                  25                  30

Glu Gly Gly Thr Glu Ser Ala Val Lys Ala Phe Gln Lys Asp Met Ser
        35                  40                  45

Phe Thr Val Val Asp Gly Ile Ile Gly Asn Gln Thr Ala Lys His Leu
    50                  55                  60

Val Asp Met Tyr Tyr Gly Lys Val Val Pro Phe Gly Tyr Val Thr Asn
65                  70                  75                  80

Thr Pro Trp Val Ser Glu Ala Ile Glu Asp Tyr Phe Val Ser Glu Ile
                85                  90                  95

Lys Gly Glu Lys His Asn Pro Arg Val Val Gln Tyr Phe Lys Asp Ala
            100                 105                 110

His Ser Ser Trp Phe Thr Asp Asp Glu Thr Pro Trp Cys Ala Ala Ala
        115                 120                 125

Val Ser Ser Trp Leu Glu Arg Ala Gly Ile Arg Ser Val Arg Ser Ala
    130                 135                 140

Arg Ala Arg Asp His Ile Asn Phe Gly Thr Lys Leu Leu Glu Pro Arg
145                 150                 155                 160

Phe Gly Ala Ile Val Val Leu Glu Arg Gly Ala Asn Ser Gly His Val
                165                 170                 175

Gly Phe Val Asn Gly Val Thr Ala Asp Gly Lys Gln Ile Lys Val Leu
            180                 185                 190

Gly Gly Asn Gln Ser Asp Ser Val Asn Glu Arg Met Phe Gln Val Thr
        195                 200                 205

Arg Val Leu Gly Tyr Arg Gln Pro Glu Gly Phe Val Leu Pro Pro Cys
    210                 215                 220

Pro Ile Val Gly Lys Gly Glu Leu Ser Lys Ser Glu Ala
225                 230                 235

<210> SEQ ID NO 28
<211> LENGTH: 4
<212> TYPE: PRT
<213> ORGANISM: artificial
<220> FEATURE:
<223> OTHER INFORMATION: Synthetic amino acid linker
```

```
<400> SEQUENCE: 28

Gly Ala Gly Ala
1

<210> SEQ ID NO 29
<211> LENGTH: 8
<212> TYPE: PRT
<213> ORGANISM: artificial
<220> FEATURE:
<223> OTHER INFORMATION: Synthetic amino acid linker

<400> SEQUENCE: 29

Gly Ala Gly Ala Gly Ala Gly Ala
1               5

<210> SEQ ID NO 30
<211> LENGTH: 12
<212> TYPE: PRT
<213> ORGANISM: artificial
<220> FEATURE:
<223> OTHER INFORMATION: Synthetic amino acid linker

<400> SEQUENCE: 30

Gly Ala Gly Ala Gly Ala Gly Ala Gly Ala Gly Ala
1               5                   10

<210> SEQ ID NO 31
<211> LENGTH: 6
<212> TYPE: PRT
<213> ORGANISM: artificial sequence
<220> FEATURE:
<223> OTHER INFORMATION: Synthetic amino acid (His-Tag (6x))

<400> SEQUENCE: 31

His His His His His His
1               5

<210> SEQ ID NO 32
<211> LENGTH: 169
<212> TYPE: PRT
<213> ORGANISM: Artificial sequence
<220> FEATURE:
<223> OTHER INFORMATION: Synthetic amino acid (Mutated peptide deriving
      from Cecropin A (A. aegypti) linked to S394 endolysin)

<400> SEQUENCE: 32

Met Gly Gly Leu Lys Lys Leu Gly Lys Lys Leu Lys Lys Ala Gly Lys
1               5                   10                  15

Arg Val Phe Lys Ala Ala Lys Lys Ala Leu Gly Gly Ser Gly Ser
            20                  25                  30

Met Ser Phe Lys Phe Gly Lys Asn Ser Glu Lys Gln Leu Ala Thr Val
        35                  40                  45

Lys Pro Glu Leu Gln Lys Val Ala Arg Arg Ala Leu Glu Leu Ser Pro
    50                  55                  60

Tyr Asp Phe Thr Ile Val Gln Gly Ile Arg Thr Val Ala Gln Ser Ala
65                  70                  75                  80

Gln Asn Ile Ala Asn Gly Thr Ser Phe Leu Lys Asp Pro Ser Lys Ser
                85                  90                  95

Lys His Val Thr Gly Asp Ala Ile Asp Phe Ala Pro Tyr Ile Asn Gly
            100                 105                 110

Lys Ile Asp Trp Lys Asp Leu Glu Ala Phe Trp Ala Val Lys Lys Ala
        115                 120                 125
```

Phe Gln Ala Gly Lys Glu Leu Gly Ile Lys Leu Arg Phe Gly Ala
    130                 135                 140
Asp Trp Asn Ser Ser Gly Asp Tyr His Asp Glu Ile Asp Arg Gly Thr
145                 150                 155                 160
Tyr Asp Gly Gly His Val Glu Leu Val
                165

<210> SEQ ID NO 33
<211> LENGTH: 355
<212> TYPE: PRT
<213> ORGANISM: Artificial sequence
<220> FEATURE:
<223> OTHER INFORMATION: Synthetic amino acid (Mutated peptide deriving
      from Cecropin A (A. aegypti) linked to OBPgpLys endolysin)

<400> SEQUENCE: 33

Met Arg Gly Leu Lys Lys Leu Gly Arg Lys Leu Lys Lys Ala Gly Lys
1               5                   10                  15
Arg Val Phe Lys Ala Ala Lys Lys Ala Leu Gly Ser Lys Asn Ser Glu
                20                  25                  30
Lys Asn Ala Ser Ile Ile Met Ser Ile Gln Arg Thr Leu Ala Ser Leu
            35                  40                  45
Ser Leu Tyr Gly Gly Arg Ile Asp Gly Leu Phe Gly Glu Lys Cys Arg
        50                  55                  60
Gly Ala Ile Ile Leu Met Leu Asn Lys Val Tyr Pro Asn Phe Ser Thr
65                  70                  75                  80
Asn Lys Leu Pro Ser Asn Thr Tyr Glu Ala Glu Ser Val Phe Thr Phe
                85                  90                  95
Leu Gln Thr Ala Leu Ala Gly Val Gly Leu Tyr Thr Ile Thr Ile Asp
            100                 105                 110
Gly Lys Trp Gly Gly Thr Ser Gln Gly Ala Ile Asp Ala Leu Val Lys
        115                 120                 125
Ser Tyr Arg Gln Ile Thr Glu Ala Glu Arg Ala Gly Ser Thr Leu Pro
    130                 135                 140
Leu Gly Leu Ala Thr Val Met Ser Lys His Met Ser Ile Glu Gln Leu
145                 150                 155                 160
Arg Ala Met Leu Pro Thr Asp Arg Gln Gly Tyr Ala Glu Val Tyr Ile
                165                 170                 175
Asp Pro Leu Asn Glu Thr Met Asp Ile Phe Glu Ile Asn Thr Pro Leu
            180                 185                 190
Arg Ile Ala His Phe Met Ala Gln Ile Leu His Glu Thr Ala Cys Phe
        195                 200                 205
Lys Tyr Thr Glu Glu Leu Ala Ser Gly Lys Ala Tyr Glu Gly Arg Ala
    210                 215                 220
Asp Leu Gly Asn Thr Arg Pro Gly Asp Gly Pro Leu Phe Lys Gly Arg
225                 230                 235                 240
Gly Leu Leu Gln Ile Thr Gly Arg Leu Asn Tyr Val Lys Cys Gln Val
                245                 250                 255
Tyr Leu Arg Glu Lys Leu Lys Asp Pro Thr Phe Asp Ile Thr Ser Ser
            260                 265                 270
Val Thr Cys Ala Gln Gln Leu Ser Glu Ser Pro Leu Leu Ala Ala Leu
        275                 280                 285
Ala Ser Gly Tyr Phe Trp Arg Phe Ile Lys Pro Lys Leu Asn Glu Thr
    290                 295                 300
Ala Asp Lys Asp Asp Ile Tyr Trp Val Ser Val Tyr Val Asn Gly Tyr
305                 310                 315                 320

```
Ala Lys Gln Ala Asn Pro Tyr Tyr Pro Asn Arg Asp Lys Glu Pro Asn
            325                 330                 335

His Met Lys Glu Arg Val Gln Met Leu Ala Val Thr Lys Lys Ala Leu
        340                 345                 350

Gly Ile Val
        355
```

<210> SEQ ID NO 34
<211> LENGTH: 290
<212> TYPE: PRT
<213> ORGANISM: Artificial Sequence
<220> FEATURE:
<223> OTHER INFORMATION: Synthetic amino acid (Mutated peptide deriving
      from BMAP-28 linked to mutated KZ144 with C14S, C23S and C50S)

<400> SEQUENCE: 34

```
Met Arg Gly Leu Arg Arg Leu Gly Arg Lys Ile Leu Arg Ala Trp Lys
1               5                   10                  15

Lys Tyr Gly Pro Ile Ile Val Pro Ile Ile Arg Ile Gly Gly Ser Lys
            20                  25                  30

Val Leu Arg Lys Gly Asp Arg Gly Asp Glu Val Ser Gln Leu Gln Thr
        35                  40                  45

Leu Leu Asn Leu Ser Gly Tyr Asp Val Gly Lys Pro Asp Gly Ile Phe
    50                  55                  60

Gly Asn Asn Thr Phe Asn Gln Val Val Lys Phe Gln Lys Asp Asn Ser
65                  70                  75                  80

Leu Asp Ser Asp Gly Ile Val Gly Lys Asn Thr Trp Ala Glu Leu Phe
                85                  90                  95

Ser Lys Tyr Ser Pro Pro Ile Pro Tyr Lys Thr Ile Pro Met Pro Thr
            100                 105                 110

Ala Asn Lys Ser Arg Ala Ala Ala Thr Pro Val Met Asn Ala Val Glu
        115                 120                 125

Asn Ala Thr Gly Val Arg Ser Gln Leu Leu Thr Phe Ala Ser Ile
    130                 135                 140

Glu Ser Ala Phe Asp Tyr Glu Ile Lys Ala Lys Thr Ser Ser Ala Thr
145                 150                 155                 160

Gly Trp Phe Gln Phe Leu Thr Gly Thr Trp Lys Thr Met Ile Glu Asn
                165                 170                 175

Tyr Gly Met Lys Tyr Gly Val Leu Thr Asp Pro Thr Gly Ala Leu Arg
            180                 185                 190

Lys Asp Pro Arg Ile Ser Ala Leu Met Gly Ala Glu Leu Ile Lys Glu
        195                 200                 205

Asn Met Asn Ile Leu Arg Pro Val Leu Lys Arg Glu Pro Thr Asp Thr
    210                 215                 220

Asp Leu Tyr Leu Ala His Phe Phe Gly Pro Gly Ala Ala Arg Arg Phe
225                 230                 235                 240

Leu Thr Thr Gly Gln Asn Glu Leu Ala Ala Thr His Phe Pro Lys Glu
                245                 250                 255

Ala Gln Ala Asn Pro Ser Ile Phe Tyr Asn Lys Asp Gly Ser Pro Lys
            260                 265                 270

Thr Ile Gln Glu Val Tyr Asn Leu Met Asp Gly Lys Val Ala Ala His
        275                 280                 285

Arg Lys
    290
```

-continued

```
<210> SEQ ID NO 35
<211> LENGTH: 162
<212> TYPE: PRT
<213> ORGANISM: Artificial sequence
<220> FEATURE:
<223> OTHER INFORMATION: Synthetic amino acid (Mutated peptide deriving
      from MSI-78 (4-20) peptide linked to S394 endolysin)

<400> SEQUENCE: 35

Met Arg Phe Leu Arg Arg Ala Arg Arg Phe Gly Arg Ala Phe Val Arg
1               5                   10                  15

Ile Leu Gly Gly Gly Gly Ser Gly Ser Met Ser Phe Lys Phe Gly Lys
            20                  25                  30

Asn Ser Glu Lys Gln Leu Ala Thr Val Lys Pro Glu Leu Gln Lys Val
        35                  40                  45

Ala Arg Arg Ala Leu Glu Leu Ser Pro Tyr Asp Phe Thr Ile Val Gln
    50                  55                  60

Gly Ile Arg Thr Val Ala Gln Ser Ala Gln Asn Ile Ala Asn Gly Thr
65                  70                  75                  80

Ser Phe Leu Lys Asp Pro Ser Lys Ser Lys His Val Thr Gly Asp Ala
                85                  90                  95

Ile Asp Phe Ala Pro Tyr Ile Asn Gly Lys Ile Asp Trp Lys Asp Leu
            100                 105                 110

Glu Ala Phe Trp Ala Val Lys Lys Ala Phe Glu Gln Ala Gly Lys Glu
        115                 120                 125

Leu Gly Ile Lys Leu Arg Phe Gly Ala Asp Trp Asn Ser Ser Gly Asp
    130                 135                 140

Tyr His Asp Glu Ile Asp Arg Gly Thr Tyr Asp Gly Gly His Val Glu
145                 150                 155                 160

Leu Val

<210> SEQ ID NO 36
<211> LENGTH: 166
<212> TYPE: PRT
<213> ORGANISM: Artificial sequence
<220> FEATURE:
<223> OTHER INFORMATION: Synthetic amino acid (Mutated peptide deriving
      from magainin peptide linked to S394 endolysin)

<400> SEQUENCE: 36

Met Gly Ile Lys Lys Phe Leu Lys Ser Ala Lys Lys Phe Gly Lys Ala
1               5                   10                  15

Phe Lys Lys Val Ile Arg Gly Gly Gly Ser Gly Ser Met Ser Phe
            20                  25                  30

Lys Phe Gly Lys Asn Ser Glu Lys Gln Leu Ala Thr Val Lys Pro Glu
        35                  40                  45

Leu Gln Lys Val Ala Arg Arg Ala Leu Glu Leu Ser Pro Tyr Asp Phe
    50                  55                  60

Thr Ile Val Gln Gly Ile Arg Thr Val Ala Gln Ser Ala Gln Asn Ile
65                  70                  75                  80

Ala Asn Gly Thr Ser Phe Leu Lys Asp Pro Ser Lys Ser Lys His Val
                85                  90                  95

Thr Gly Asp Ala Ile Asp Phe Ala Pro Tyr Ile Asn Gly Lys Ile Asp
            100                 105                 110

Trp Lys Asp Leu Glu Ala Phe Trp Ala Val Lys Lys Ala Phe Glu Gln
        115                 120                 125

Ala Gly Lys Glu Leu Gly Ile Lys Leu Arg Phe Gly Ala Asp Trp Asn
    130                 135                 140
```

```
Ser Ser Gly Asp Tyr His Asp Glu Ile Asp Arg Gly Thr Tyr Asp Gly
145                 150                 155                 160

Gly His Val Glu Leu Val
                165

<210> SEQ ID NO 37
<211> LENGTH: 282
<212> TYPE: PRT
<213> ORGANISM: Artificial sequence
<220> FEATURE:
<223> OTHER INFORMATION: Synthetic amino acid (Mutated peptide deriving
      from HPA-NT3 peptide linked to mutated KZ144 with C14S, C23S and
      C50S)

<400> SEQUENCE: 37

Met Lys Arg Leu Lys Lys Leu Ala Lys Lys Ile Trp Lys Trp Gly Arg
1               5                   10                  15

Arg Gly Pro Gly Ser Gly Ser Lys Val Leu Arg Lys Gly Asp Arg Gly
                20                  25                  30

Asp Glu Val Ser Gln Leu Gln Thr Leu Leu Asn Leu Ser Gly Tyr Asp
                35                  40                  45

Val Gly Lys Pro Asp Gly Ile Phe Gly Asn Asn Thr Phe Asn Gln Val
50                  55                  60

Val Lys Phe Gln Lys Asp Asn Ser Leu Asp Ser Asp Gly Ile Val Gly
65                  70                  75                  80

Lys Asn Thr Trp Ala Glu Leu Phe Ser Lys Tyr Ser Pro Ile Pro
                85                  90                  95

Tyr Lys Thr Ile Pro Met Pro Thr Ala Asn Lys Ser Arg Ala Ala Ala
                100                 105                 110

Thr Pro Val Met Asn Ala Val Glu Asn Ala Thr Gly Val Arg Ser Gln
                115                 120                 125

Leu Leu Leu Thr Phe Ala Ser Ile Glu Ser Ala Phe Asp Tyr Glu Ile
130                 135                 140

Lys Ala Lys Thr Ser Ser Ala Thr Gly Trp Phe Gln Phe Leu Thr Gly
145                 150                 155                 160

Thr Trp Lys Thr Met Ile Glu Asn Tyr Gly Met Lys Tyr Gly Val Leu
                165                 170                 175

Thr Asp Pro Thr Gly Ala Leu Arg Lys Asp Pro Arg Ile Ser Ala Leu
                180                 185                 190

Met Gly Ala Glu Leu Ile Lys Glu Asn Met Asn Ile Leu Arg Pro Val
                195                 200                 205

Leu Lys Arg Glu Pro Thr Asp Thr Asp Leu Tyr Leu Ala His Phe Phe
210                 215                 220

Gly Pro Gly Ala Ala Arg Arg Phe Leu Thr Thr Gly Gln Asn Glu Leu
225                 230                 235                 240

Ala Ala Thr His Phe Pro Lys Glu Ala Gln Ala Asn Pro Ser Ile Phe
                245                 250                 255

Tyr Asn Lys Asp Gly Ser Pro Lys Thr Ile Gln Glu Val Tyr Asn Leu
                260                 265                 270

Met Asp Gly Lys Val Ala Ala His Arg Lys
                275                 280

<210> SEQ ID NO 38
<211> LENGTH: 291
<212> TYPE: PRT
<213> ORGANISM: Artificial sequence
<220> FEATURE:
```

```
<223> OTHER INFORMATION: Synthetic amino acid (Mutated peptide deriving
      from amino acids 298-326 of the alpha subunit of stonustoxin
      linked to mutated KZ144 with C14S, C23S and C50S)

<400> SEQUENCE: 38

Met Ile Lys Leu Ile Lys Arg Val Ile Lys Phe Lys Lys Ile Phe
1               5                   10                  15

Arg Lys Tyr Pro Leu Thr Val Lys Lys Gly Ile Ala Val Gly Gly Ser
                20                  25                  30

Lys Val Leu Arg Lys Gly Asp Arg Gly Asp Glu Val Ser Gln Leu Gln
            35                  40                  45

Thr Leu Leu Asn Leu Ser Gly Tyr Asp Val Gly Lys Pro Asp Gly Ile
    50                  55                  60

Phe Gly Asn Asn Thr Phe Asn Gln Val Val Lys Phe Gln Lys Asp Asn
65                  70                  75                  80

Ser Leu Asp Ser Asp Gly Ile Val Gly Lys Asn Thr Trp Ala Glu Leu
                85                  90                  95

Phe Ser Lys Tyr Ser Pro Pro Ile Pro Tyr Lys Thr Ile Pro Met Pro
                100                 105                 110

Thr Ala Asn Lys Ser Arg Ala Ala Ala Thr Pro Val Met Asn Ala Val
            115                 120                 125

Glu Asn Ala Thr Gly Val Arg Ser Gln Leu Leu Thr Phe Ala Ser
    130                 135                 140

Ile Glu Ser Ala Phe Asp Tyr Glu Ile Lys Ala Lys Thr Ser Ser Ala
145                 150                 155                 160

Thr Gly Trp Phe Gln Phe Leu Thr Gly Thr Trp Lys Thr Met Ile Glu
                165                 170                 175

Asn Tyr Gly Met Lys Tyr Gly Val Leu Thr Asp Pro Thr Gly Ala Leu
                180                 185                 190

Arg Lys Asp Pro Arg Ile Ser Ala Leu Met Gly Ala Glu Leu Ile Lys
            195                 200                 205

Glu Asn Met Asn Ile Leu Arg Pro Val Leu Lys Arg Glu Pro Thr Asp
    210                 215                 220

Thr Asp Leu Tyr Leu Ala His Phe Phe Gly Pro Gly Ala Ala Arg Arg
225                 230                 235                 240

Phe Leu Thr Thr Gly Gln Asn Glu Leu Ala Ala Thr His Phe Pro Lys
                245                 250                 255

Glu Ala Gln Ala Asn Pro Ser Ile Phe Tyr Asn Lys Asp Gly Ser Pro
                260                 265                 270

Lys Thr Ile Gln Glu Val Tyr Asn Leu Met Asp Gly Lys Val Ala Ala
            275                 280                 285

His Arg Lys
    290

<210> SEQ ID NO 39
<211> LENGTH: 289
<212> TYPE: PRT
<213> ORGANISM: Artificial sequence
<220> FEATURE:
<223> OTHER INFORMATION: Synthetic amino acid (Mutated peptide deriving
      from amino acids 26-48 of CagL protein linked to mutated KZ144
      with C14S, C23S and C50S)

<400> SEQUENCE: 39

Met Gly Leu Lys Lys Leu Lys Arg Val Tyr Arg Lys Trp Val Lys Ala
1               5                   10                  15

Val Lys Lys Val Leu Lys Leu Gly Gly Gly Gly Ser Gly Ser Lys Val
```

```
                 20                  25                  30

Leu Arg Lys Gly Asp Arg Gly Asp Glu Val Ser Gln Leu Gln Thr Leu
             35                  40                  45

Leu Asn Leu Ser Gly Tyr Asp Val Gly Lys Pro Asp Gly Ile Phe Gly
 50                  55                  60

Asn Asn Thr Phe Asn Gln Val Val Lys Phe Gln Lys Asp Asn Ser Leu
 65                  70                  75                  80

Asp Ser Asp Gly Ile Val Gly Lys Asn Thr Trp Ala Glu Leu Phe Ser
                 85                  90                  95

Lys Tyr Ser Pro Pro Ile Pro Tyr Lys Thr Ile Pro Met Pro Thr Ala
             100                 105                 110

Asn Lys Ser Arg Ala Ala Ala Thr Pro Val Met Asn Ala Val Glu Asn
             115                 120                 125

Ala Thr Gly Val Arg Ser Gln Leu Leu Leu Thr Phe Ala Ser Ile Glu
             130                 135                 140

Ser Ala Phe Asp Tyr Glu Ile Lys Ala Lys Thr Ser Ser Ala Thr Gly
145                 150                 155                 160

Trp Phe Gln Phe Leu Thr Gly Thr Trp Lys Thr Met Ile Glu Asn Tyr
                 165                 170                 175

Gly Met Lys Tyr Gly Val Leu Thr Asp Pro Thr Gly Ala Leu Arg Lys
             180                 185                 190

Asp Pro Arg Ile Ser Ala Leu Met Gly Ala Glu Leu Ile Lys Glu Asn
             195                 200                 205

Met Asn Ile Leu Arg Pro Val Leu Lys Arg Glu Pro Thr Asp Thr Asp
             210                 215                 220

Leu Tyr Leu Ala His Phe Phe Gly Pro Gly Ala Ala Arg Arg Phe Leu
225                 230                 235                 240

Thr Thr Gly Gln Asn Glu Leu Ala Ala Thr His Phe Pro Lys Glu Ala
                 245                 250                 255

Gln Ala Asn Pro Ser Ile Phe Tyr Asn Lys Asp Gly Ser Pro Lys Thr
             260                 265                 270

Ile Gln Glu Val Tyr Asn Leu Met Asp Gly Lys Val Ala Ala His Arg
             275                 280                 285

Lys

<210> SEQ ID NO 40
<211> LENGTH: 284
<212> TYPE: PRT
<213> ORGANISM: Artificial sequence
<220> FEATURE:
<223> OTHER INFORMATION: Synthetic amino acid (Mutated peptide deriving
      from amino acids 26-48 of CagL protein linked to mutated KZ144
      with C14S, C23S and C50S)

<400> SEQUENCE: 40

Met Gly Leu Lys Val Leu Lys Lys Ala Tyr Arg Arg Ile Arg Lys Ala
1               5                   10                  15

Val Arg Lys Ile Leu Lys Ala Gly Ser Lys Val Leu Arg Lys Gly Asp
             20                  25                  30

Arg Gly Asp Glu Val Ser Gln Leu Gln Thr Leu Leu Asn Leu Ser Gly
             35                  40                  45

Tyr Asp Val Gly Lys Pro Asp Gly Ile Phe Gly Asn Asn Thr Phe Asn
 50                  55                  60

Gln Val Val Lys Phe Gln Lys Asp Asn Ser Leu Asp Ser Asp Gly Ile
 65                  70                  75                  80
```

Val Gly Lys Asn Thr Trp Ala Glu Leu Phe Ser Lys Tyr Ser Pro Pro
                85                  90                  95

Ile Pro Tyr Lys Thr Ile Pro Met Pro Thr Ala Asn Lys Ser Arg Ala
            100                 105                 110

Ala Ala Thr Pro Val Met Asn Ala Val Glu Asn Ala Thr Gly Val Arg
        115                 120                 125

Ser Gln Leu Leu Leu Thr Phe Ala Ser Ile Glu Ser Ala Phe Asp Tyr
    130                 135                 140

Glu Ile Lys Ala Lys Thr Ser Ser Ala Thr Gly Trp Phe Gln Phe Leu
145                 150                 155                 160

Thr Gly Thr Trp Lys Thr Met Ile Glu Asn Tyr Gly Met Lys Tyr Gly
                165                 170                 175

Val Leu Thr Asp Pro Thr Gly Ala Leu Arg Lys Asp Pro Arg Ile Ser
            180                 185                 190

Ala Leu Met Gly Ala Glu Leu Ile Lys Glu Asn Met Asn Ile Leu Arg
        195                 200                 205

Pro Val Leu Lys Arg Glu Pro Thr Asp Thr Asp Leu Tyr Leu Ala His
    210                 215                 220

Phe Phe Gly Pro Gly Ala Ala Arg Arg Phe Leu Thr Thr Gly Gln Asn
225                 230                 235                 240

Glu Leu Ala Ala Thr His Phe Pro Lys Glu Ala Gln Ala Asn Pro Ser
                245                 250                 255

Ile Phe Tyr Asn Lys Asp Gly Ser Pro Lys Thr Ile Gln Glu Val Tyr
            260                 265                 270

Asn Leu Met Asp Gly Lys Val Ala Ala His Arg Lys
        275                 280

<210> SEQ ID NO 41
<211> LENGTH: 281
<212> TYPE: PRT
<213> ORGANISM: Artificial sequence
<220> FEATURE:
<223> OTHER INFORMATION: Synthetic amino acid (Mutated peptide deriving
      from amino acids 178-198 of IE1 protein linked to mutated KZ144
      with C14S, C23S and C50S)

<400> SEQUENCE: 41

Met Tyr Lys Arg Ala Phe Lys Lys Val Leu Lys Arg Ile Arg Arg Tyr
1               5                   10                  15

Ala Lys Arg Ser Gly Ser Lys Val Leu Arg Lys Gly Asp Arg Gly Asp
            20                  25                  30

Glu Val Ser Gln Leu Gln Thr Leu Leu Asn Leu Ser Gly Tyr Asp Val
        35                  40                  45

Gly Lys Pro Asp Gly Ile Phe Gly Asn Asn Thr Phe Asn Gln Val Val
    50                  55                  60

Lys Phe Gln Lys Asp Asn Ser Leu Asp Ser Asp Gly Ile Val Gly Lys
65                  70                  75                  80

Asn Thr Trp Ala Glu Leu Phe Ser Lys Tyr Ser Pro Pro Ile Pro Tyr
                85                  90                  95

Lys Thr Ile Pro Met Pro Thr Ala Asn Lys Ser Arg Ala Ala Ala Thr
            100                 105                 110

Pro Val Met Asn Ala Val Glu Asn Ala Thr Gly Val Arg Ser Gln Leu
        115                 120                 125

Leu Leu Thr Phe Ala Ser Ile Glu Ser Ala Phe Asp Tyr Glu Ile Lys
    130                 135                 140

Ala Lys Thr Ser Ser Ala Thr Gly Trp Phe Gln Phe Leu Thr Gly Thr

```
145                 150                 155                 160
Trp Lys Thr Met Ile Glu Asn Tyr Gly Met Lys Tyr Gly Val Leu Thr
                165                 170                 175

Asp Pro Thr Gly Ala Leu Arg Lys Asp Pro Arg Ile Ser Ala Leu Met
            180                 185                 190

Gly Ala Glu Leu Ile Lys Glu Asn Met Asn Ile Leu Arg Pro Val Leu
        195                 200                 205

Lys Arg Glu Pro Thr Asp Thr Asp Leu Tyr Leu Ala His Phe Phe Gly
    210                 215                 220

Pro Gly Ala Ala Arg Arg Phe Leu Thr Thr Gly Gln Asn Glu Leu Ala
225                 230                 235                 240

Ala Thr His Phe Pro Lys Glu Ala Gln Ala Asn Pro Ser Ile Phe Tyr
                245                 250                 255

Asn Lys Asp Gly Ser Pro Lys Thr Ile Gln Glu Val Tyr Asn Leu Met
            260                 265                 270

Asp Gly Lys Val Ala Ala His Arg Lys
        275                 280

<210> SEQ ID NO 42
<211> LENGTH: 168
<212> TYPE: PRT
<213> ORGANISM: Artificial sequence
<220> FEATURE:
<223> OTHER INFORMATION: Synthetic amino acid

<400> SEQUENCE: 42

Met Gly Phe Phe Lys Lys Ala Trp Arg Lys Val Lys His Ala Gly Arg
1               5                   10                  15

Arg Val Leu Lys Thr Ala Lys Gly Val Gly Gly Ser Gly Ser Met
            20                  25                  30

Ser Phe Lys Phe Gly Lys Asn Ser Glu Lys Gln Leu Ala Thr Val Lys
        35                  40                  45

Pro Glu Leu Gln Lys Val Ala Arg Arg Ala Leu Glu Leu Ser Pro Tyr
    50                  55                  60

Asp Phe Thr Ile Val Gln Gly Ile Arg Thr Val Ala Gln Ser Ala Gln
65                  70                  75                  80

Asn Ile Ala Asn Gly Thr Ser Phe Leu Lys Asp Pro Ser Lys Ser Lys
                85                  90                  95

His Val Thr Gly Asp Ala Ile Asp Phe Ala Pro Tyr Ile Asn Gly Lys
            100                 105                 110

Ile Asp Trp Lys Asp Leu Glu Ala Phe Trp Ala Val Lys Lys Ala Phe
        115                 120                 125

Glu Gln Ala Gly Lys Glu Leu Gly Ile Lys Leu Arg Phe Gly Ala Asp
    130                 135                 140

Trp Asn Ser Ser Gly Asp Tyr His Asp Glu Ile Asp Arg Gly Thr Tyr
145                 150                 155                 160

Asp Gly Gly His Val Glu Leu Val
                165

<210> SEQ ID NO 43
<211> LENGTH: 267
<212> TYPE: PRT
<213> ORGANISM: artificial sequence
<220> FEATURE:
<223> OTHER INFORMATION: Synthetic amino acid (Mutated peptide deriving
      from magainin peptide linked to tail baseplate protein of Vibrio
      phage ICP1)
```

<400> SEQUENCE: 43

| | | | | | | | | | | | | | | | |
|---|---|---|---|---|---|---|---|---|---|---|---|---|---|---|---|
| Met | Gly | Ile | Lys | Lys | Phe | Leu | Lys | Ser | Ala | Lys | Lys | Phe | Gly | Lys | Ala |
| 1 | | | | 5 | | | | | 10 | | | | | 15 | |
| Phe | Lys | Lys | Val | Ile | Arg | Gly | Gly | Gly | Ser | Gly | Ser | Met | Ile | Leu | |
| | | | 20 | | | | | 25 | | | | | 30 | | |
| Lys | Arg | Gly | Ser | Ser | Gly | Ala | Asp | Val | Lys | Asn | Met | Gln | Glu | Tyr | Leu |
| | | 35 | | | | | 40 | | | | | 45 | | | |
| Thr | Ala | Leu | Gly | Tyr | Asp | Thr | Lys | Gly | Val | Glu | Gly | Thr | Phe | Glu | Gly |
| 50 | | | | | 55 | | | | | 60 | | | | | |
| Gly | Thr | Glu | Ser | Ala | Val | Lys | Ala | Phe | Gln | Lys | Asp | Met | Ser | Phe | Thr |
| 65 | | | | | 70 | | | | | 75 | | | | | 80 |
| Val | Val | Asp | Gly | Ile | Ile | Gly | Asn | Gln | Thr | Ala | Lys | His | Leu | Val | Asp |
| | | | | 85 | | | | | 90 | | | | | 95 | |
| Met | Tyr | Tyr | Gly | Lys | Val | Val | Pro | Phe | Gly | Tyr | Val | Thr | Asn | Thr | Pro |
| | | | 100 | | | | | 105 | | | | | 110 | | |
| Trp | Val | Ser | Glu | Ala | Ile | Glu | Asp | Tyr | Phe | Val | Ser | Glu | Ile | Lys | Gly |
| | | | 115 | | | | | 120 | | | | | 125 | | |
| Glu | Lys | His | Asn | Pro | Arg | Val | Val | Gln | Tyr | Phe | Lys | Asp | Ala | His | Ser |
| | 130 | | | | | 135 | | | | | 140 | | | | |
| Ser | Trp | Phe | Thr | Asp | Asp | Glu | Thr | Pro | Trp | Cys | Ala | Ala | Ala | Val | Ser |
| 145 | | | | | 150 | | | | | 155 | | | | | 160 |
| Ser | Trp | Leu | Glu | Arg | Ala | Gly | Ile | Arg | Ser | Val | Arg | Ser | Ala | Arg | Ala |
| | | | | 165 | | | | | 170 | | | | | 175 | |
| Arg | Asp | His | Ile | Asn | Phe | Gly | Thr | Lys | Leu | Leu | Glu | Pro | Arg | Phe | Gly |
| | | | 180 | | | | | 185 | | | | | 190 | | |
| Ala | Ile | Val | Val | Leu | Glu | Arg | Gly | Ala | Asn | Ser | Gly | His | Val | Gly | Phe |
| | | | 195 | | | | | 200 | | | | | 205 | | |
| Val | Asn | Gly | Val | Thr | Ala | Asp | Gly | Lys | Gln | Ile | Lys | Val | Leu | Gly | Gly |
| | | | 210 | | | | | 215 | | | | | 220 | | |
| Asn | Gln | Ser | Asp | Ser | Val | Asn | Glu | Arg | Met | Phe | Gln | Val | Thr | Arg | Val |
| 225 | | | | | 230 | | | | | 235 | | | | | 240 |
| Leu | Gly | Tyr | Arg | Gln | Pro | Glu | Gly | Phe | Val | Leu | Pro | Pro | Cys | Pro | Ile |
| | | | | 245 | | | | | 250 | | | | | 255 | |
| Val | Gly | Lys | Gly | Glu | Leu | Ser | Lys | Ser | Glu | Ala | | | | | |
| | | | 260 | | | | | 265 | | | | | | | |

<210> SEQ ID NO 44
<211> LENGTH: 36
<212> TYPE: PRT
<213> ORGANISM: Aedes aegypti

<400> SEQUENCE: 44

| | | | | | | | | | | | | | | | |
|---|---|---|---|---|---|---|---|---|---|---|---|---|---|---|---|
| Gly | Gly | Leu | Lys | Lys | Leu | Gly | Lys | Lys | Leu | Glu | Gly | Ala | Gly | Lys | Arg |
| 1 | | | | 5 | | | | | 10 | | | | | 15 | |
| Val | Phe | Asn | Ala | Ala | Glu | Lys | Ala | Leu | Pro | Val | Val | Ala | Gly | Ala | Lys |
| | | | 20 | | | | | 25 | | | | | 30 | | |
| Ala | Leu | Arg | Lys | | | | | | | | | | | | |
| | | | 35 | | | | | | | | | | | | |

<210> SEQ ID NO 45
<211> LENGTH: 184
<212> TYPE: PRT
<213> ORGANISM: Artificial sequence
<220> FEATURE:
<223> OTHER INFORMATION: Synthetic amino acid (Cecropin A (A. aegypti) linked to S394 endolysin)

<400> SEQUENCE: 45

Met Gly Gly Leu Lys Lys Leu Gly Lys Lys Leu Glu Gly Ala Gly Lys
1               5                   10                  15

Arg Val Phe Asn Ala Ala Glu Lys Ala Leu Pro Val Val Ala Gly Ala
            20                  25                  30

Lys Ala Leu Arg Lys Gly Ala Gly Ala Gly Ala Gly Ser Met
        35                  40                  45

Ser Phe Lys Phe Gly Lys Asn Ser Glu Lys Gln Leu Ala Thr Val Lys
50                  55                  60

Pro Glu Leu Gln Lys Val Ala Arg Arg Ala Leu Glu Leu Ser Pro Tyr
65                  70                  75                  80

Asp Phe Thr Ile Val Gln Gly Ile Arg Thr Val Ala Gln Ser Ala Gln
                85                  90                  95

Asn Ile Ala Asn Gly Thr Ser Phe Leu Lys Asp Pro Ser Lys Ser Lys
            100                 105                 110

His Val Thr Gly Asp Ala Ile Asp Phe Ala Pro Tyr Ile Asn Gly Lys
        115                 120                 125

Ile Asp Trp Lys Asp Leu Glu Ala Phe Trp Ala Val Lys Lys Ala Phe
    130                 135                 140

Glu Gln Ala Gly Lys Glu Leu Gly Ile Lys Leu Arg Phe Gly Ala Asp
145                 150                 155                 160

Trp Asn Ser Ser Gly Asp Tyr His Asp Glu Ile Asp Arg Gly Thr Tyr
                165                 170                 175

Asp Gly Gly His Val Glu Leu Val
            180

<210> SEQ ID NO 46
<211> LENGTH: 366
<212> TYPE: PRT
<213> ORGANISM: Artificial sequence
<220> FEATURE:
<223> OTHER INFORMATION: Synthetic amino acid (Cecropin A (A. aegypti)
      linked to OBPgpLys endolysin)

<400> SEQUENCE: 46

Met Gly Gly Leu Lys Lys Leu Gly Lys Lys Leu Glu Gly Ala Gly Lys
1               5                   10                  15

Arg Val Phe Asn Ala Ala Glu Lys Ala Leu Pro Val Val Ala Gly Ala
            20                  25                  30

Lys Ala Leu Arg Lys Gly Ser Lys Asn Ser Glu Lys Asn Ala Ser Ile
        35                  40                  45

Ile Met Ser Ile Gln Arg Thr Leu Ala Ser Leu Ser Leu Tyr Gly Gly
50                  55                  60

Arg Ile Asp Gly Leu Phe Gly Glu Lys Cys Arg Gly Ala Ile Ile Leu
65                  70                  75                  80

Met Leu Asn Lys Val Tyr Pro Asn Phe Ser Thr Asn Lys Leu Pro Ser
                85                  90                  95

Asn Thr Tyr Glu Ala Glu Ser Val Phe Thr Phe Leu Gln Thr Ala Leu
            100                 105                 110

Ala Gly Val Gly Leu Tyr Thr Ile Thr Ile Asp Gly Lys Trp Gly Gly
        115                 120                 125

Thr Ser Gln Gly Ala Ile Asp Ala Leu Val Lys Ser Tyr Arg Gln Ile
    130                 135                 140

Thr Glu Ala Glu Arg Ala Gly Ser Thr Leu Pro Leu Gly Leu Ala Thr
145                 150                 155                 160

```
Val Met Ser Lys His Met Ser Ile Glu Gln Leu Arg Ala Met Leu Pro
            165                 170                 175

Thr Asp Arg Gln Gly Tyr Ala Glu Val Tyr Ile Asp Pro Leu Asn Glu
        180                 185                 190

Thr Met Asp Ile Phe Glu Ile Asn Thr Pro Leu Arg Ile Ala His Phe
        195                 200                 205

Met Ala Gln Ile Leu His Glu Thr Ala Cys Phe Lys Tyr Thr Glu Glu
        210                 215                 220

Leu Ala Ser Gly Lys Ala Tyr Glu Gly Arg Ala Asp Leu Gly Asn Thr
225                 230                 235                 240

Arg Pro Gly Asp Gly Pro Leu Phe Lys Gly Arg Gly Leu Leu Gln Ile
            245                 250                 255

Thr Gly Arg Leu Asn Tyr Val Lys Cys Gln Val Tyr Leu Arg Glu Lys
            260                 265                 270

Leu Lys Asp Pro Thr Phe Asp Ile Thr Ser Ser Val Thr Cys Ala Gln
            275                 280                 285

Gln Leu Ser Glu Ser Pro Leu Leu Ala Ala Leu Ala Ser Gly Tyr Phe
            290                 295                 300

Trp Arg Phe Ile Lys Pro Lys Leu Asn Glu Thr Ala Asp Lys Asp Asp
305                 310                 315                 320

Ile Tyr Trp Val Ser Val Tyr Val Asn Gly Tyr Ala Lys Gln Ala Asn
                325                 330                 335

Pro Tyr Tyr Pro Asn Arg Asp Lys Glu Pro Asn His Met Lys Glu Arg
            340                 345                 350

Val Gln Met Leu Ala Val Thr Lys Lys Ala Leu Gly Ile Val
            355                 360                 365

<210> SEQ ID NO 47
<211> LENGTH: 28
<212> TYPE: PRT
<213> ORGANISM: Unknown
<220> FEATURE:
<223> OTHER INFORMATION: Synthetic amino acid (BMAP-28, bovines)

<400> SEQUENCE: 47

Gly Gly Leu Arg Ser Leu Gly Arg Lys Ile Leu Arg Ala Trp Lys Lys
1               5                   10                  15

Tyr Gly Pro Ile Ile Val Pro Ile Ile Arg Ile Gly
            20                  25

<210> SEQ ID NO 48
<211> LENGTH: 290
<212> TYPE: PRT
<213> ORGANISM: Artificial sequence
<220> FEATURE:
<223> OTHER INFORMATION: Synthetic amino acid (BMAP-28 linked to mutated
    KZ144 with C14S, C23S and C50S)

<400> SEQUENCE: 48

Met Gly Gly Leu Arg Ser Leu Gly Arg Lys Ile Leu Arg Ala Trp Lys
1               5                   10                  15

Lys Tyr Gly Pro Ile Ile Val Pro Ile Ile Arg Ile Gly Gly Ser Lys
            20                  25                  30

Val Leu Arg Lys Gly Asp Arg Gly Asp Glu Val Ser Gln Leu Gln Thr
        35                  40                  45

Leu Leu Asn Leu Ser Gly Tyr Asp Val Gly Lys Pro Asp Gly Ile Phe
50                  55                  60

Gly Asn Asn Thr Phe Asn Gln Val Val Lys Phe Gln Lys Asp Asn Ser
```

```
                65                  70                  75                  80
Leu Asp Ser Asp Gly Ile Val Gly Lys Asn Thr Trp Ala Glu Leu Phe
                    85                  90                  95

Ser Lys Tyr Ser Pro Pro Ile Pro Tyr Lys Thr Ile Pro Met Pro Thr
                100                 105                 110

Ala Asn Lys Ser Arg Ala Ala Ala Thr Pro Val Met Asn Ala Val Glu
                115                 120                 125

Asn Ala Thr Gly Val Arg Ser Gln Leu Leu Thr Phe Ala Ser Ile
            130                 135                 140

Glu Ser Ala Phe Asp Tyr Glu Ile Lys Ala Lys Thr Ser Ser Ala Thr
145                 150                 155                 160

Gly Trp Phe Gln Phe Leu Thr Gly Thr Trp Lys Thr Met Ile Glu Asn
                    165                 170                 175

Tyr Gly Met Lys Tyr Gly Val Leu Thr Asp Pro Thr Gly Ala Leu Arg
                180                 185                 190

Lys Asp Pro Arg Ile Ser Ala Leu Met Gly Ala Glu Leu Ile Lys Glu
                195                 200                 205

Asn Met Asn Ile Leu Arg Pro Val Leu Lys Arg Glu Pro Thr Asp Thr
            210                 215                 220

Asp Leu Tyr Leu Ala His Phe Phe Gly Pro Gly Ala Ala Arg Arg Phe
225                 230                 235                 240

Leu Thr Thr Gly Gln Asn Glu Leu Ala Ala Thr His Phe Pro Lys Glu
                    245                 250                 255

Ala Gln Ala Asn Pro Ser Ile Phe Tyr Asn Lys Asp Gly Ser Pro Lys
                260                 265                 270

Thr Ile Gln Glu Val Tyr Asn Leu Met Asp Gly Lys Val Ala Ala His
            275                 280                 285

Arg Lys
    290

<210> SEQ ID NO 49
<211> LENGTH: 17
<212> TYPE: PRT
<213> ORGANISM: Artificial Sequence
<220> FEATURE:
<223> OTHER INFORMATION: Synthetic amino acid (MSI-78 (4-20) peptide)

<400> SEQUENCE: 49

Lys Phe Leu Lys Lys Ala Lys Lys Phe Gly Lys Ala Phe Val Lys Ile
1               5                   10                  15

Leu

<210> SEQ ID NO 50
<211> LENGTH: 162
<212> TYPE: PRT
<213> ORGANISM: Artificial sequence
<220> FEATURE:
<223> OTHER INFORMATION: Synthetic amino acid (MSI-78 (4-20) peptide
      linked to S394 endolysin)

<400> SEQUENCE: 50

Met Lys Phe Leu Lys Lys Ala Lys Lys Phe Gly Lys Ala Phe Val Lys
1               5                   10                  15

Ile Leu Gly Gly Gly Gly Ser Gly Ser Met Ser Phe Lys Phe Gly Lys
                20                  25                  30

Asn Ser Glu Lys Gln Leu Ala Thr Val Lys Pro Glu Leu Gln Lys Val
            35                  40                  45
```

```
Ala Arg Arg Ala Leu Glu Leu Ser Pro Tyr Asp Phe Thr Ile Val Gln
    50                  55                  60

Gly Ile Arg Thr Val Ala Gln Ser Ala Gln Asn Ile Ala Asn Gly Thr
65                  70                  75                  80

Ser Phe Leu Lys Asp Pro Ser Lys Ser Lys His Val Thr Gly Asp Ala
                85                  90                  95

Ile Asp Phe Ala Pro Tyr Ile Asn Gly Lys Ile Asp Trp Lys Asp Leu
                100                 105                 110

Glu Ala Phe Trp Ala Val Lys Lys Ala Phe Glu Gln Ala Gly Lys Glu
                115                 120                 125

Leu Gly Ile Lys Leu Arg Phe Gly Ala Asp Trp Asn Ser Ser Gly Asp
130                 135                 140

Tyr His Asp Glu Ile Asp Arg Gly Thr Tyr Asp Gly Gly His Val Glu
145                 150                 155                 160

Leu Val
```

<210> SEQ ID NO 51
<211> LENGTH: 23
<212> TYPE: PRT
<213> ORGANISM: Xenopus laevis

<400> SEQUENCE: 51

```
Gly Ile Gly Lys Phe Leu His Ser Ala Lys Lys Phe Gly Lys Ala Phe
1               5                   10                  15

Val Gly Glu Ile Met Asn Ser
                20
```

<210> SEQ ID NO 52
<211> LENGTH: 163
<212> TYPE: PRT
<213> ORGANISM: Artificial sequence
<220> FEATURE:
<223> OTHER INFORMATION: Synthetic amino acid (Magainin peptide linked to S394 endolysin)

<400> SEQUENCE: 52

```
Met Gly Ile Gly Lys Phe Leu His Ser Ala Lys Lys Phe Gly Lys Ala
1               5                   10                  15

Phe Val Gly Glu Ile Met Asn Ser Gly Ser Met Ser Phe Lys Phe Gly
                20                  25                  30

Lys Asn Ser Glu Lys Gln Leu Ala Thr Val Lys Pro Glu Leu Gln Lys
                35                  40                  45

Val Ala Arg Arg Ala Leu Glu Leu Ser Pro Tyr Asp Phe Thr Ile Val
    50                  55                  60

Gln Gly Ile Arg Thr Val Ala Gln Ser Ala Gln Asn Ile Ala Asn Gly
65                  70                  75                  80

Thr Ser Phe Leu Lys Asp Pro Ser Lys Ser Lys His Val Thr Gly Asp
                85                  90                  95

Ala Ile Asp Phe Ala Pro Tyr Ile Asn Gly Lys Ile Asp Trp Lys Asp
                100                 105                 110

Leu Glu Ala Phe Trp Ala Val Lys Lys Ala Phe Glu Gln Ala Gly Lys
                115                 120                 125

Glu Leu Gly Ile Lys Leu Arg Phe Gly Ala Asp Trp Asn Ser Ser Gly
130                 135                 140

Asp Tyr His Asp Glu Ile Asp Arg Gly Thr Tyr Asp Gly Gly His Val
145                 150                 155                 160

Glu Leu Val
```

<210> SEQ ID NO 53
<211> LENGTH: 15
<212> TYPE: PRT
<213> ORGANISM: Helicobacter pylori

<400> SEQUENCE: 53

Phe Lys Arg Leu Lys Lys Leu Phe Lys Lys Ile Trp Asn Trp Lys
1               5                   10                  15

<210> SEQ ID NO 54
<211> LENGTH: 277
<212> TYPE: PRT
<213> ORGANISM: Artificial sequence
<220> FEATURE:
<223> OTHER INFORMATION: Synthetic amino acid (Amino acids XXX of
      HPA-NT3 peptide linked to mutated KZ144 with C14S, C23S and C50S)

<400> SEQUENCE: 54

Met Phe Lys Arg Leu Lys Lys Leu Phe Lys Lys Ile Trp Asn Trp Lys
1               5                   10                  15

Gly Ser Lys Val Le

```
<211> LENGTH: 29
<212> TYPE: PRT
<213> ORGANISM: Synanceia verrucosa

<400> SEQUENCE: 55

Ile Pro Leu Ile His Asp Lys Ile Ser Asn Phe Gln Gln Ile Phe Gln
1               5                   10                  15

Asp Tyr Met Leu Thr Val Gln Lys Lys Ile Ala Glu Lys
            20                  25

<210> SEQ ID NO 56
<211> LENGTH: 291
<212> TYPE: PRT
<213> ORGANISM: Artificial sequence
<220> FEATURE:
<223> OTHER INFORMATION: Synthetic amino acid (Amino acids 298-326 of
      the alpha subunit of stonustoxin linked to mutated KZ144 with
      C14S, C23S and C50S)

<400> SEQUENCE: 56

Met Ile Pro Leu Ile His Asp Lys Ile Ser Asn Phe Gln Gln Ile Phe
1               5                   10                  15

Gln Asp Tyr Met Leu Thr Val Gln Lys Lys Ile Ala Glu Lys Gly Ser
            20                  25                  30

Lys Val Leu Arg Lys Gly Asp Arg Gly Asp Glu Val Ser Gln Leu Gln
        35                  40                  45

Thr Leu Asn Leu Ser Gly Tyr Asp Val Gly Lys Pro Asp Gly Ile
    50                  55                  60

Phe Gly Asn Asn Thr Phe Asn Gln Val Val Lys Phe Gln Lys Asp Asn
65                  70                  75                  80

Ser Leu Asp Ser Asp Gly Ile Val Gly Lys Asn Thr Trp Ala Glu Leu
                85                  90                  95

Phe Ser Lys Tyr Ser Pro Pro Ile Pro Tyr Lys Thr Ile Pro Met Pro
            100                 105                 110

Thr Ala Asn Lys Ser Arg Ala Ala Ala Thr Pro Val Met Asn Ala Val
        115                 120                 125

Glu Asn Ala Thr Gly Val Arg Ser Gln Leu Leu Leu Thr Phe Ala Ser
    130                 135                 140

Ile Glu Ser Ala Phe Asp Tyr Glu Ile Lys Ala Lys Thr Ser Ser Ala
145                 150                 155                 160

Thr Gly Trp Phe Gln Phe Leu Thr Gly Thr Trp Lys Thr Met Ile Glu
                165                 170                 175

Asn Tyr Gly Met Lys Tyr Gly Val Leu Thr Asp Pro Thr Gly Ala Leu
            180                 185                 190

Arg Lys Asp Pro Arg Ile Ser Ala Leu Met Gly Ala Glu Leu Ile Lys
        195                 200                 205

Glu Asn Met Asn Ile Leu Arg Pro Val Leu Lys Arg Glu Pro Thr Asp
    210                 215                 220

Thr Asp Leu Tyr Leu Ala His Phe Phe Gly Pro Gly Ala Ala Arg Arg
225                 230                 235                 240

Phe Leu Thr Thr Gly Gln Asn Glu Leu Ala Ala Thr His Phe Pro Lys
                245                 250                 255

Glu Ala Gln Ala Asn Pro Ser Ile Phe Tyr Asn Lys Asp Gly Ser Pro
            260                 265                 270

Lys Thr Ile Gln Glu Val Tyr Asn Leu Met Asp Gly Lys Val Ala Ala
        275                 280                 285

His Arg Lys
```

<210> SEQ ID NO 57
<211> LENGTH: 22
<212> TYPE: PRT
<213> ORGANISM: Helicobacter pylori

<400> SEQUENCE: 57

Gly Leu Lys Gln Leu Asp Ser Thr Tyr Gln Glu Thr Asn Gln Gln Val
1               5                   10                  15

Leu Lys Asn Leu Asp Glu
            20

<210> SEQ ID NO 58
<211> LENGTH: 284
<212> TYPE: PRT
<213> ORGANISM: Artificial sequence
<220> FEATURE:
<223> OTHER INFORMATION: Synthetic amino acid (Amino acids 26-48 of CagL
      protein linked to mutated KZ144 with C14S, C23S and C50S)

<400> SEQUENCE: 58

Met Gly Leu Lys Gln Leu Asp Ser Thr Tyr Gln Glu Thr Asn Gln Gln
1               5                   10                  15

Val Leu Lys Asn Leu Asp Glu Gly Ser Lys Val Leu Arg Lys Gly Asp
            20                  25                  30

Arg Gly Asp Glu Val Ser Gln Leu Gln Thr Leu Leu Asn Leu Ser Gly
        35                  40                  45

Tyr Asp Val Gly Lys Pro Asp Gly Ile Phe Gly Asn Asn Thr Phe Asn
    50                  55                  60

Gln Val Val Lys Phe Gln Lys Asp Asn Ser Leu Asp Ser Asp Gly Ile
65                  70                  75                  80

Val Gly Lys Asn Thr Trp Ala Glu Leu Phe Ser Lys Tyr Ser Pro Pro
                85                  90                  95

Ile Pro Tyr Lys Thr Ile Pro Met Pro Thr Ala Asn Lys Ser Arg Ala
            100                 105                 110

Ala Ala Thr Pro Val Met Asn Ala Val Glu Asn Ala Thr Gly Val Arg
        115                 120                 125

Ser Gln Leu Leu Leu Thr Phe Ala Ser Ile Glu Ser Ala Phe Asp Tyr
    130                 135                 140

Glu Ile Lys Ala Lys Thr Ser Ser Ala Thr Gly Trp Phe Gln Phe Leu
145                 150                 155                 160

Thr Gly Thr Trp Lys Thr Met Ile Glu Asn Tyr Gly Met Lys Tyr Gly
                165                 170                 175

Val Leu Thr Asp Pro Thr Gly Ala Leu Arg Lys Asp Pro Arg Ile Ser
            180                 185                 190

Ala Leu Met Gly Ala Glu Leu Ile Lys Glu Asn Met Asn Ile Leu Arg
        195                 200                 205

Pro Val Leu Lys Arg Glu Pro Thr Asp Thr Asp Leu Tyr Leu Ala His
    210                 215                 220

Phe Phe Gly Pro Gly Ala Ala Arg Arg Phe Leu Thr Thr Gly Gln Asn
225                 230                 235                 240

Glu Leu Ala Ala Thr His Phe Pro Lys Glu Ala Gln Ala Asn Pro Ser
                245                 250                 255

Ile Phe Tyr Asn Lys Asp Gly Ser Pro Lys Thr Ile Gln Glu Val Tyr
            260                 265                 270

Asn Leu Met Asp Gly Lys Val Ala Ala His Arg Lys

```
                      275                 280

<210> SEQ ID NO 59
<211> LENGTH: 19
<212> TYPE: PRT
<213> ORGANISM: Human cytomegalovirus

<400> SEQUENCE: 59

Tyr Lys Glu Lys Phe Met Val Cys Leu Lys Gln Ile Val Gln Tyr Ala
1               5                   10                  15

Val Asn Ser

<210> SEQ ID NO 60
<211> LENGTH: 281
<212> TYPE: PRT
<213> ORGANISM: Artificial sequence
<220> FEATURE:
<223> OTHER INFORMATION: Synthetic amino acid (Amino acids 178-198 of
      IE1 protein linked to mutated KZ144 with C14S, C23S and C50S)

<400> SEQUENCE: 60

Met Tyr Lys Glu Lys Phe Met Val Cys Leu Lys Gln Ile Val Gln Tyr
1               5                   10                  15

Ala Val Asn Ser Gly Ser Lys Val Leu Arg Lys Gly Asp Arg Gly Asp
                20                  25                  30

Glu Val Ser Gln Leu Gln Thr Leu Leu Asn Leu Ser Gly Tyr Asp Val
            35                  40                  45

Gly Lys Pro Asp Gly Ile Phe Gly Asn Asn Thr Phe Asn Gln Val Val
        50                  55                  60

Lys Phe Gln Lys Asp Asn Ser Leu Asp Ser Asp Gly Ile Val Gly Lys
65                  70                  75                  80

Asn Thr Trp Ala Glu Leu Phe Ser Lys Tyr Ser Pro Pro Ile Pro Tyr
                85                  90                  95

Lys Thr Ile Pro Met Pro Thr Ala Asn Lys Ser Arg Ala Ala Ala Thr
            100                 105                 110

Pro Val Met Asn Ala Val Glu Asn Ala Thr Gly Val Arg Ser Gln Leu
        115                 120                 125

Leu Leu Thr Phe Ala Ser Ile Glu Ser Ala Phe Asp Tyr Glu Ile Lys
130                 135                 140

Ala Lys Thr Ser Ser Ala Thr Gly Trp Phe Gln Phe Leu Thr Gly Thr
145                 150                 155                 160

Trp Lys Thr Met Ile Glu Asn Tyr Gly Met Lys Tyr Gly Val Leu Thr
                165                 170                 175

Asp Pro Thr Gly Ala Leu Arg Lys Asp Pro Arg Ile Ser Ala Leu Met
            180                 185                 190

Gly Ala Glu Leu Ile Lys Glu Asn Met Asn Ile Leu Arg Pro Val Leu
        195                 200                 205

Lys Arg Glu Pro Thr Asp Thr Asp Leu Tyr Leu Ala His Phe Phe Gly
    210                 215                 220

Pro Gly Ala Ala Arg Arg Phe Leu Thr Thr Gly Gln Asn Glu Leu Ala
225                 230                 235                 240

Ala Thr His Phe Pro Lys Glu Ala Gln Ala Asn Pro Ser Ile Phe Tyr
                245                 250                 255

Asn Lys Asp Gly Ser Pro Lys Thr Ile Gln Glu Val Tyr Asn Leu Met
            260                 265                 270

Asp Gly Lys Val Ala Ala His Arg Lys
        275                 280
```

<210> SEQ ID NO 61
<211> LENGTH: 278
<212> TYPE: PRT
<213> ORGANISM: Artificial sequence
<220> FEATURE:
<223> OTHER INFORMATION: Synthetic amino acid

<400> SEQUENCE: 61

```
Met Arg Gly Leu Arg Arg Leu Gly Arg Lys Ile Ala His Gly Val Lys
1               5                   10                  15

Lys Gly Ser Lys Val Leu Arg Lys Gly Asp Arg Gly Asp Glu Val Ser
            20                  25                  30

Gln Leu Gln Thr Leu Leu Asn Leu Ser Gly Tyr Asp Val Gly Lys Pro
        35                  40                  45

Asp Gly Ile Phe Gly Asn Asn Thr Phe Asn Gln Val Val Lys Phe Gln
    50                  55                  60

Lys Asp Asn Ser Leu Asp Ser Asp Gly Ile Val Gly Lys Asn Thr Trp
65                  70                  75                  80

Ala Glu Leu Phe Ser Lys Tyr Ser Pro Pro Ile Pro Tyr Lys Thr Ile
                85                  90                  95

Pro Met Pro Thr Ala Asn Lys Ser Arg Ala Ala Ala Thr Pro Val Met
            100                 105                 110

Asn Ala Val Glu Asn Ala Thr Gly Val Arg Ser Gln Leu Leu Leu Thr
        115                 120                 125

Phe Ala Ser Ile Glu Ser Ala Phe Asp Tyr Glu Ile Lys Ala Lys Thr
    130                 135                 140

Ser Ser Ala Thr Gly Trp Phe Gln Phe Leu Thr Gly Thr Trp Lys Thr
145                 150                 155                 160

Met Ile Glu Asn Tyr Gly Met Lys Tyr Gly Val Leu Thr Asp Pro Thr
                165                 170                 175

Gly Ala Leu Arg Lys Asp Pro Arg Ile Ser Ala Leu Met Gly Ala Glu
            180                 185                 190

Leu Ile Lys Glu Asn Met Asn Ile Leu Arg Pro Val Leu Lys Arg Glu
        195                 200                 205

Pro Thr Asp Thr Asp Leu Tyr Leu Ala His Phe Phe Gly Pro Gly Ala
    210                 215                 220

Ala Arg Arg Phe Leu Thr Thr Gly Gln Asn Glu Leu Ala Ala Thr His
225                 230                 235                 240

Phe Pro Lys Glu Ala Gln Ala Asn Pro Ser Ile Phe Tyr Asn Lys Asp
                245                 250                 255

Gly Ser Pro Lys Thr Ile Gln Glu Val Tyr Asn Leu Met Asp Gly Lys
            260                 265                 270

Val Ala Ala His Arg Lys
        275
```

<210> SEQ ID NO 62
<211> LENGTH: 286
<212> TYPE: PRT
<213> ORGANISM: Artificial sequence
<220> FEATURE:
<223> OTHER INFORMATION: Synthetic amino acid

<400> SEQUENCE: 62

```
Met Arg Gly Leu Arg Arg Leu Gly Arg Lys Ile Ala His Gly Val Lys
1               5                   10                  15

Lys Gly Ala Gly Ala Gly Ala Gly Ala Gly Ser Lys Val Leu Arg Lys
```

```
            20                  25                  30
Gly Asp Arg Gly Asp Glu Val Ser Gln Leu Gln Thr Leu Leu Asn Leu
        35                  40                  45

Ser Gly Tyr Asp Val Gly Lys Pro Asp Gly Ile Phe Gly Asn Asn Thr
    50                  55                  60

Phe Asn Gln Val Val Lys Phe Gln Lys Asp Asn Ser Leu Asp Ser Asp
65                  70                  75                  80

Gly Ile Val Gly Lys Asn Thr Trp Ala Glu Leu Phe Ser Lys Tyr Ser
                85                  90                  95

Pro Pro Ile Pro Tyr Lys Thr Ile Pro Met Pro Thr Ala Asn Lys Ser
            100                 105                 110

Arg Ala Ala Ala Thr Pro Val Met Asn Ala Val Glu Asn Ala Thr Gly
        115                 120                 125

Val Arg Ser Gln Leu Leu Leu Thr Phe Ala Ser Ile Glu Ser Ala Phe
    130                 135                 140

Asp Tyr Glu Ile Lys Ala Lys Thr Ser Ser Ala Thr Gly Trp Phe Gln
145                 150                 155                 160

Phe Leu Thr Gly Thr Trp Lys Thr Met Ile Glu Asn Tyr Gly Met Lys
                165                 170                 175

Tyr Gly Val Leu Thr Asp Pro Thr Gly Ala Leu Arg Lys Asp Pro Arg
            180                 185                 190

Ile Ser Ala Leu Met Gly Ala Glu Leu Ile Lys Glu Asn Met Asn Ile
        195                 200                 205

Leu Arg Pro Val Leu Lys Arg Glu Pro Thr Asp Thr Asp Leu Tyr Leu
    210                 215                 220

Ala His Phe Phe Gly Pro Gly Ala Ala Arg Arg Phe Leu Thr Thr Gly
225                 230                 235                 240

Gln Asn Glu Leu Ala Ala Thr His Phe Pro Lys Glu Ala Gln Ala Asn
                245                 250                 255

Pro Ser Ile Phe Tyr Asn Lys Asp Gly Ser Pro Lys Thr Ile Gln Glu
            260                 265                 270

Val Tyr Asn Leu Met Asp Gly Lys Val Ala Ala His Arg Lys
        275                 280                 285

<210> SEQ ID NO 63
<211> LENGTH: 279
<212> TYPE: PRT
<213> ORGANISM: Artificial sequence
<220> FEATURE:
<223> OTHER INFORMATION: Synthetic amino acid

<400> SEQUENCE: 63

Met Arg Gly Leu Arg Arg Leu Gly Arg Lys Ile Ala His Gly Val Lys
1               5                   10                  15

Lys Tyr Gly Ser Lys Val Leu Arg Lys Gly Asp Arg Gly Asp Glu Val
            20                  25                  30

Ser Gln Leu Gln Thr Leu Leu Asn Leu Ser Gly Tyr Asp Val Gly Lys
        35                  40                  45

Pro Asp Gly Ile Phe Gly Asn Asn Thr Phe Asn Gln Val Val Lys Phe
    50                  55                  60

Gln Lys Asp Asn Ser Leu Asp Ser Asp Gly Ile Val Gly Lys Asn Thr
65                  70                  75                  80

Trp Ala Glu Leu Phe Ser Lys Tyr Ser Pro Pro Ile Pro Tyr Lys Thr
                85                  90                  95

Ile Pro Met Pro Thr Ala Asn Lys Ser Arg Ala Ala Ala Thr Pro Val
```

```
                        100                 105                 110
Met Asn Ala Val Glu Asn Ala Thr Gly Val Arg Ser Gln Leu Leu Leu
                    115                 120                 125

Thr Phe Ala Ser Ile Glu Ser Ala Phe Asp Tyr Glu Ile Lys Ala Lys
    130                 135                 140

Thr Ser Ser Ala Thr Gly Trp Phe Gln Phe Leu Thr Gly Thr Trp Lys
145                 150                 155                 160

Thr Met Ile Glu Asn Tyr Gly Met Lys Tyr Gly Val Leu Thr Asp Pro
                165                 170                 175

Thr Gly Ala Leu Arg Lys Asp Pro Arg Ile Ser Ala Leu Met Gly Ala
            180                 185                 190

Glu Leu Ile Lys Glu Asn Met Asn Ile Leu Arg Pro Val Leu Lys Arg
        195                 200                 205

Glu Pro Thr Asp Thr Asp Leu Tyr Leu Ala His Phe Phe Gly Pro Gly
    210                 215                 220

Ala Ala Arg Arg Phe Leu Thr Thr Gly Gln Asn Glu Leu Ala Ala Thr
225                 230                 235                 240

His Phe Pro Lys Glu Ala Gln Ala Asn Pro Ser Ile Phe Tyr Asn Lys
                245                 250                 255

Asp Gly Ser Pro Lys Thr Ile Gln Glu Val Tyr Asn Leu Met Asp Gly
            260                 265                 270

Lys Val Ala Ala His Arg Lys
        275

<210> SEQ ID NO 64
<211> LENGTH: 285
<212> TYPE: PRT
<213> ORGANISM: Artificial sequence
<220> FEATURE:
<223> OTHER INFORMATION: Synthetic amino acid

<400> SEQUENCE: 64

Met Arg Gly Leu Arg Arg Leu Gly Arg Lys Ile Ala His Gly Val Lys
1               5                   10                  15

Lys Tyr Lys Pro Lys Pro Lys Pro Gly Ser Lys Val Leu Arg Lys Gly
            20                  25                  30

Asp Arg Gly Asp Glu Val Ser Gln Leu Gln Thr Leu Leu Asn Leu Ser
        35                  40                  45

Gly Tyr Asp Val Gly Lys Pro Asp Gly Ile Phe Gly Asn Asn Thr Phe
    50                  55                  60

Asn Gln Val Val Lys Phe Gln Lys Asp Asn Ser Leu Asp Ser Asp Gly
65                  70                  75                  80

Ile Val Gly Lys Asn Thr Trp Ala Glu Leu Phe Ser Lys Tyr Ser Pro
                85                  90                  95

Pro Ile Pro Tyr Lys Thr Ile Pro Met Pro Thr Ala Asn Lys Ser Arg
            100                 105                 110

Ala Ala Ala Thr Pro Val Met Asn Ala Val Glu Asn Ala Thr Gly Val
        115                 120                 125

Arg Ser Gln Leu Leu Leu Thr Phe Ala Ser Ile Glu Ser Ala Phe Asp
    130                 135                 140

Tyr Glu Ile Lys Ala Lys Thr Ser Ser Ala Thr Gly Trp Phe Gln Phe
145                 150                 155                 160

Leu Thr Gly Thr Trp Lys Thr Met Ile Glu Asn Tyr Gly Met Lys Tyr
                165                 170                 175

Gly Val Leu Thr Asp Pro Thr Gly Ala Leu Arg Lys Asp Pro Arg Ile
```

```
            180                 185                 190
Ser Ala Leu Met Gly Ala Glu Leu Ile Lys Glu Asn Met Asn Ile Leu
            195                 200                 205

Arg Pro Val Leu Lys Arg Glu Pro Thr Asp Thr Asp Leu Tyr Leu Ala
        210                 215                 220

His Phe Phe Gly Pro Gly Ala Ala Arg Arg Phe Leu Thr Thr Gly Gln
225                 230                 235                 240

Asn Glu Leu Ala Ala Thr His Phe Pro Lys Glu Ala Gln Ala Asn Pro
                245                 250                 255

Ser Ile Phe Tyr Asn Lys Asp Gly Ser Pro Lys Thr Ile Gln Glu Val
            260                 265                 270

Tyr Asn Leu Met Asp Gly Lys Val Ala Ala His Arg Lys
            275                 280                 285

<210> SEQ ID NO 65
<211> LENGTH: 280
<212> TYPE: PRT
<213> ORGANISM: Artificial sequence
<220> FEATURE:
<223> OTHER INFORMATION: Synthetic amino acid

<400> SEQUENCE: 65

Met Arg Gly Leu Arg Arg Leu Gly Arg Lys Ile Ala His Gly Val Lys
1               5                   10                  15

Lys Tyr Gly Gly Ser Lys Val Leu Arg Lys Gly Asp Arg Gly Asp Glu
            20                  25                  30

Val Ser Gln Leu Gln Thr Leu Leu Asn Leu Ser Gly Tyr Asp Val Gly
        35                  40                  45

Lys Pro Asp Gly Ile Phe Gly Asn Asn Thr Phe Asn Gln Val Val Lys
    50                  55                  60

Phe Gln Lys Asp Asn Ser Leu Asp Ser Asp Gly Ile Val Gly Lys Asn
65                  70                  75                  80

Thr Trp Ala Glu Leu Phe Ser Lys Tyr Ser Pro Pro Ile Pro Tyr Lys
                85                  90                  95

Thr Ile Pro Met Pro Thr Ala Asn Lys Ser Arg Ala Ala Ala Thr Pro
            100                 105                 110

Val Met Asn Ala Val Glu Asn Ala Thr Gly Val Arg Ser Gln Leu Leu
        115                 120                 125

Leu Thr Phe Ala Ser Ile Glu Ser Ala Phe Asp Tyr Glu Ile Lys Ala
    130                 135                 140

Lys Thr Ser Ser Ala Thr Gly Trp Phe Gln Phe Leu Thr Gly Thr Trp
145                 150                 155                 160

Lys Thr Met Ile Glu Asn Tyr Gly Met Lys Tyr Gly Val Leu Thr Asp
                165                 170                 175

Pro Thr Gly Ala Leu Arg Lys Asp Pro Arg Ile Ser Ala Leu Met Gly
            180                 185                 190

Ala Glu Leu Ile Lys Glu Asn Met Asn Ile Leu Arg Pro Val Leu Lys
        195                 200                 205

Arg Glu Pro Thr Asp Thr Asp Leu Tyr Leu Ala His Phe Phe Gly Pro
    210                 215                 220

Gly Ala Ala Arg Arg Phe Leu Thr Thr Gly Gln Asn Glu Leu Ala Ala
225                 230                 235                 240

Thr His Phe Pro Lys Glu Ala Gln Ala Asn Pro Ser Ile Phe Tyr Asn
                245                 250                 255

Lys Asp Gly Ser Pro Lys Thr Ile Gln Glu Val Tyr Asn Leu Met Asp
```

-continued

```
                    260                 265                 270
Gly Lys Val Ala Ala His Arg Lys
            275                 280

<210> SEQ ID NO 66
<211> LENGTH: 284
<212> TYPE: PRT
<213> ORGANISM: Artificial sequence
<220> FEATURE:
<223> OTHER INFORMATION: Synthetic amino acid

<400> SEQUENCE: 66

Met Arg Gly Leu Arg Arg Leu Gly Arg Lys Ile Ala His Gly Val Lys
1               5                   10                  15

Lys Tyr Gly Gly Gly Ser Gly Ser Lys Val Leu Arg Lys Gly Asp
            20                  25                  30

Arg Gly Asp Glu Val Ser Gln Leu Gln Thr Leu Leu Asn Leu Ser Gly
        35                  40                  45

Tyr Asp Val Gly Lys Pro Asp Gly Ile Phe Gly Asn Asn Thr Phe Asn
50                  55                  60

Gln Val Val Lys Phe Gln Lys Asp Asn Ser Leu Asp Ser Asp Gly Ile
65                  70                  75                  80

Val Gly Lys Asn Thr Trp Ala Glu Leu Phe Ser Lys Tyr Ser Pro Pro
                85                  90                  95

Ile Pro Tyr Lys Thr Ile Pro Met Pro Thr Ala Asn Lys Ser Arg Ala
            100                 105                 110

Ala Ala Thr Pro Val Met Asn Ala Val Glu Asn Ala Thr Gly Val Arg
        115                 120                 125

Ser Gln Leu Leu Leu Thr Phe Ala Ser Ile Glu Ser Ala Phe Asp Tyr
130                 135                 140

Glu Ile Lys Ala Lys Thr Ser Ser Ala Thr Gly Trp Phe Gln Phe Leu
145                 150                 155                 160

Thr Gly Thr Trp Lys Thr Met Ile Glu Asn Tyr Gly Met Lys Tyr Gly
                165                 170                 175

Val Leu Thr Asp Pro Thr Gly Ala Leu Arg Lys Asp Pro Arg Ile Ser
            180                 185                 190

Ala Leu Met Gly Ala Glu Leu Ile Lys Glu Asn Met Asn Ile Leu Arg
        195                 200                 205

Pro Val Leu Lys Arg Glu Pro Thr Asp Thr Asp Leu Tyr Leu Ala His
210                 215                 220

Phe Phe Gly Pro Gly Ala Ala Arg Arg Phe Leu Thr Thr Gly Gln Asn
225                 230                 235                 240

Glu Leu Ala Ala Thr His Phe Pro Lys Glu Ala Gln Ala Asn Pro Ser
                245                 250                 255

Ile Phe Tyr Asn Lys Asp Gly Ser Pro Lys Thr Ile Gln Glu Val Tyr
            260                 265                 270

Asn Leu Met Asp Gly Lys Val Ala Ala His Arg Lys
        275                 280

<210> SEQ ID NO 67
<211> LENGTH: 280
<212> TYPE: PRT
<213> ORGANISM: Artificial sequence
<220> FEATURE:
<223> OTHER INFORMATION: Synthetic amino acid

<400> SEQUENCE: 67
```

Met Gly Arg Lys Ile Ala His Gly Val Lys Lys Tyr Gly Arg Gly Leu
1               5                   10                  15

Arg Arg Leu Gly Ser Lys Val Leu Arg Lys Gly Asp Arg Gly Asp Glu
                20                  25                  30

Val Ser Gln Leu Gln Thr Leu Leu Asn Leu Ser Gly Tyr Asp Val Gly
            35                  40                  45

Lys Pro Asp Gly Ile Phe Gly Asn Asn Thr Phe Asn Gln Val Val Lys
50                  55                  60

Phe Gln Lys Asp Asn Ser Leu Asp Ser Asp Gly Ile Val Gly Lys Asn
65                  70                  75                  80

Thr Trp Ala Glu Leu Phe Ser Lys Tyr Ser Pro Pro Ile Pro Tyr Lys
                85                  90                  95

Thr Ile Pro Met Pro Thr Ala Asn Lys Ser Arg Ala Ala Ala Thr Pro
            100                 105                 110

Val Met Asn Ala Val Glu Asn Ala Thr Gly Val Arg Ser Gln Leu Leu
            115                 120                 125

Leu Thr Phe Ala Ser Ile Glu Ser Ala Phe Asp Tyr Glu Ile Lys Ala
            130                 135                 140

Lys Thr Ser Ser Ala Thr Gly Trp Phe Gln Phe Leu Thr Gly Thr Trp
145                 150                 155                 160

Lys Thr Met Ile Glu Asn Tyr Gly Met Lys Tyr Gly Val Leu Thr Asp
                165                 170                 175

Pro Thr Gly Ala Leu Arg Lys Asp Pro Arg Ile Ser Ala Leu Met Gly
            180                 185                 190

Ala Glu Leu Ile Lys Glu Asn Met Asn Ile Leu Arg Pro Val Leu Lys
            195                 200                 205

Arg Glu Pro Thr Asp Thr Asp Leu Tyr Leu Ala His Phe Phe Gly Pro
210                 215                 220

Gly Ala Ala Arg Arg Phe Leu Thr Thr Gly Gln Asn Glu Leu Ala Ala
225                 230                 235                 240

Thr His Phe Pro Lys Glu Ala Gln Ala Asn Pro Ser Ile Phe Tyr Asn
                245                 250                 255

Lys Asp Gly Ser Pro Lys Thr Ile Gln Glu Val Tyr Asn Leu Met Asp
            260                 265                 270

Gly Lys Val Ala Ala His Arg Lys
            275                 280

<210> SEQ ID NO 68
<211> LENGTH: 291
<212> TYPE: PRT
<213> ORGANISM: Artificial sequence
<220> FEATURE:
<223> OTHER INFORMATION: Synthetic amino acid

<400> SEQUENCE: 68

Met Gly Arg Lys Ile Ala His Gly Val Lys Lys Tyr Gly Arg Gly Leu
1               5                   10                  15

Arg Arg Leu Pro Thr Val Leu Arg Ile Ile Arg Ile Ala Gly Gly Ser
                20                  25                  30

Lys Val Leu Arg Lys Gly Asp Arg Gly Asp Glu Val Ser Gln Leu Gln
            35                  40                  45

Thr Leu Leu Asn Leu Ser Gly Tyr Asp Val Gly Lys Pro Asp Gly Ile
50                  55                  60

Phe Gly Asn Asn Thr Phe Asn Gln Val Val Lys Phe Gln Lys Asp Asn
65                  70                  75                  80

```
Ser Leu Asp Ser Asp Gly Ile Val Gly Lys Asn Thr Trp Ala Glu Leu
                85                  90                  95

Phe Ser Lys Tyr Ser Pro Pro Ile Pro Tyr Lys Thr Ile Pro Met Pro
            100                 105                 110

Thr Ala Asn Lys Ser Arg Ala Ala Thr Pro Val Met Asn Ala Val
        115                 120                 125

Glu Asn Ala Thr Gly Val Arg Ser Gln Leu Leu Thr Phe Ala Ser
    130                 135                 140

Ile Glu Ser Ala Phe Asp Tyr Glu Ile Lys Ala Lys Thr Ser Ser Ala
145                 150                 155                 160

Thr Gly Trp Phe Gln Phe Leu Thr Gly Thr Trp Lys Thr Met Ile Glu
                165                 170                 175

Asn Tyr Gly Met Lys Tyr Gly Val Leu Thr Asp Pro Thr Gly Ala Leu
            180                 185                 190

Arg Lys Asp Pro Arg Ile Ser Ala Leu Met Gly Ala Glu Leu Ile Lys
        195                 200                 205

Glu Asn Met Asn Ile Leu Arg Pro Val Leu Lys Arg Glu Pro Thr Asp
    210                 215                 220

Thr Asp Leu Tyr Leu Ala His Phe Phe Gly Pro Gly Ala Ala Arg Arg
225                 230                 235                 240

Phe Leu Thr Thr Gly Gln Asn Glu Leu Ala Ala Thr His Phe Pro Lys
                245                 250                 255

Glu Ala Gln Ala Asn Pro Ser Ile Phe Tyr Asn Lys Asp Gly Ser Pro
            260                 265                 270

Lys Thr Ile Gln Glu Val Tyr Asn Leu Met Asp Gly Lys Val Ala Ala
        275                 280                 285

His Arg Lys
    290

<210> SEQ ID NO 69
<211> LENGTH: 25
<212> TYPE: PRT
<213> ORGANISM: Artificial Sequence
<220> FEATURE:
<223> OTHER INFORMATION: Synthetic amino acid (MW2)

<400> SEQUENCE: 69

Gly Lys Pro Gly Trp Leu Ile Lys Val Ala Leu Lys Phe Lys Lys Leu
1               5                   10                  15

Ile Arg Arg Pro Leu Lys Arg Leu Ala
            20                  25

<210> SEQ ID NO 70
<211> LENGTH: 295
<212> TYPE: PRT
<213> ORGANISM: artificial sequence
<220> FEATURE:
<223> OTHER INFORMATION: Synthetic amino acid (MW2 peptide linked to
      mutated KZ144 with C14S, C23S and C50S)

<400> SEQUENCE: 70

Met Gly Lys Pro Gly Trp Leu Ile Lys Val Ala Leu Lys Phe Lys Lys
1               5                   10                  15

Leu Ile Arg Arg Pro Leu Lys Arg Leu Ala Gly Ser Lys Val Leu Arg
            20                  25                  30

Lys Gly Asp Arg Gly Asp Glu Val Ser Gln Leu Gln Thr Leu Leu Asn
        35                  40                  45

Leu Ser Gly Tyr Asp Val Gly Lys Pro Asp Gly Ile Phe Gly Asn Asn
```

```
                    50                  55                  60
Thr Phe Asn Gln Val Val Lys Phe Gln Lys Asp Asn Ser Leu Asp Ser
 65                  70                  75                  80

Asp Gly Ile Val Gly Lys Asn Thr Trp Ala Glu Leu Phe Ser Lys Tyr
                 85                  90                  95

Ser Pro Pro Ile Pro Tyr Lys Thr Ile Pro Met Pro Thr Ala Asn Lys
                100                 105                 110

Ser Arg Ala Ala Ala Thr Pro Val Met Asn Ala Val Glu Asn Ala Thr
            115                 120                 125

Gly Val Arg Ser Gln Leu Leu Leu Thr Phe Ala Ser Ile Glu Ser Ala
        130                 135                 140

Phe Asp Tyr Glu Ile Lys Ala Lys Thr Ser Ser Ala Thr Gly Trp Phe
145                 150                 155                 160

Gln Phe Leu Thr Gly Thr Trp Lys Thr Met Ile Glu Asn Tyr Gly Met
                165                 170                 175

Lys Tyr Gly Val Leu Thr Asp Pro Thr Gly Ala Leu Arg Lys Asp Pro
            180                 185                 190

Arg Ile Ser Ala Leu Met Gly Ala Glu Leu Ile Lys Glu Asn Met Asn
        195                 200                 205

Ile Leu Arg Pro Val Leu Lys Arg Glu Pro Thr Asp Thr Asp Leu Tyr
210                 215                 220

Leu Ala His Phe Gly Pro Gly Ala Ala Arg Arg Phe Leu Thr Thr
225                 230                 235                 240

Gly Gln Asn Glu Leu Ala Ala Thr His Phe Pro Lys Glu Ala Gln Ala
                245                 250                 255

Asn Pro Ser Ile Phe Tyr Asn Lys Asp Gly Ser Pro Lys Thr Ile Gln
            260                 265                 270

Glu Val Tyr Asn Leu Met Asp Gly Lys Val Ala Ala His Arg Lys Leu
        275                 280                 285

Glu His His His His His His
    290                 295

<210> SEQ ID NO 71
<211> LENGTH: 25
<212> TYPE: PRT
<213> ORGANISM: Artificial sequence
<220> FEATURE:
<223> OTHER INFORMATION: Synthetic amino acid (MW2 mut (I7R;L11R;P20G))

<400> SEQUENCE: 71

Gly Lys Pro Gly Trp Leu Arg Lys Val Ala Arg Lys Phe Lys Lys Leu
 1               5                  10                  15

Ile Arg Arg Gly Leu Lys Arg Leu Ala
            20                  25

<210> SEQ ID NO 72
<211> LENGTH: 25
<212> TYPE: PRT
<213> ORGANISM: Artificial sequence
<220> FEATURE:
<223> OTHER INFORMATION: Synthetic amino acid (MW2 mut (P3V;I7R;L11R))

<400> SEQUENCE: 72

Gly Lys Val Gly Trp Leu Arg Lys Val Ala Arg Lys Phe Lys Lys Leu
 1               5                  10                  15

Ile Arg Arg Pro Leu Lys Arg Leu Ala
            20                  25
```

<210> SEQ ID NO 73
<211> LENGTH: 25
<212> TYPE: PRT
<213> ORGANISM: Artificial sequence
<220> FEATURE:
<223> OTHER INFORMATION: Synthetic amino acid (MW2 mut (I7R))

<400> SEQUENCE: 73

```
Gly Lys Pro Gly Trp Leu Arg Lys Val Ala Leu Lys Phe Lys Lys Leu
1               5                   10                  15

Ile Arg Arg Pro Leu Lys Arg Leu Ala
            20                  25
```

<210> SEQ ID NO 74
<211> LENGTH: 25
<212> TYPE: PRT
<213> ORGANISM: Artificial sequence
<220> FEATURE:
<223> OTHER INFORMATION: Synthetic amino acid (MW2 mut (L11R))

<400> SEQUENCE: 74

```
Gly Lys Pro Gly Trp Leu Ile Lys Val Ala Arg Lys Phe Lys Lys Leu
1               5                   10                  15

Ile Arg Arg Pro Leu Lys Arg Leu Ala
            20                  25
```

<210> SEQ ID NO 75
<211> LENGTH: 295
<212> TYPE: PRT
<213> ORGANISM: Artificial sequence
<220> FEATURE:
<223> OTHER INFORMATION: Synthetic amino acid (Mutated peptide deriving
      from MW2 peptide linked to mutated KZ144 with C14S, C23S and C50S)

<400> SEQUENCE: 75

```
Met Gly Lys Pro Gly Trp Leu Arg Lys Val Ala Arg Lys Phe Lys Lys
1               5                   10                  15

Leu Ile Arg Arg Gly Leu Lys Arg Leu Ala Gly Ser Lys Val Leu Arg
                20                  25                  30

Lys Gly Asp Arg Gly Asp Glu Val Ser Gln Leu Gln Thr Leu Leu Asn
            35                  40                  45

Leu Ser Gly Tyr Asp Val Gly Lys Pro Asp Gly Ile Phe Gly Asn Asn
        50                  55                  60

Thr Phe Asn Gln Val Val Lys Phe Gln Lys Asp Asn Ser Leu Asp Ser
65                  70                  75                  80

Asp Gly Ile Val Gly Lys Asn Thr Trp Ala Glu Leu Phe Ser Lys Tyr
                85                  90                  95

Ser Pro Pro Ile Pro Tyr Lys Thr Ile Pro Met Pro Thr Ala Asn Lys
            100                 105                 110

Ser Arg Ala Ala Ala Thr Pro Val Met Asn Ala Val Glu Asn Ala Thr
        115                 120                 125

Gly Val Arg Ser Gln Leu Leu Leu Thr Phe Ala Ser Ile Glu Ser Ala
    130                 135                 140

Phe Asp Tyr Glu Ile Lys Ala Lys Thr Ser Ser Ala Thr Gly Trp Phe
145                 150                 155                 160

Gln Phe Leu Thr Gly Thr Trp Lys Thr Met Ile Glu Asn Tyr Gly Met
                165                 170                 175

Lys Tyr Gly Val Leu Thr Asp Pro Thr Gly Ala Leu Arg Lys Asp Pro
            180                 185                 190
```

```
Arg Ile Ser Ala Leu Met Gly Ala Glu Leu Ile Lys Glu Asn Met Asn
            195                 200                 205

Ile Leu Arg Pro Val Leu Lys Arg Glu Pro Thr Asp Thr Asp Leu Tyr
    210                 215                 220

Leu Ala His Phe Phe Gly Pro Gly Ala Ala Arg Arg Phe Leu Thr Thr
225                 230                 235                 240

Gly Gln Asn Glu Leu Ala Ala Thr His Phe Pro Lys Glu Ala Gln Ala
                245                 250                 255

Asn Pro Ser Ile Phe Tyr Asn Lys Asp Gly Ser Pro Lys Thr Ile Gln
            260                 265                 270

Glu Val Tyr Asn Leu Met Asp Gly Lys Val Ala Ala His Arg Lys Leu
        275                 280                 285

Glu His His His His His His
    290                 295

<210> SEQ ID NO 76
<211> LENGTH: 295
<212> TYPE: PRT
<213> ORGANISM: Artificial sequence
<220> FEATURE:
<223> OTHER INFORMATION: Synthetic amino acid (Mutated peptide deriving
      from MW2 peptide linked to mutated KZ144 with C14S, C23S and C50S)

<400> SEQUENCE: 76

Met Gly Lys Val Gly Trp Leu Arg Lys Val Ala Arg Lys Phe Lys Lys
1               5                   10                  15

Leu Ile Arg Arg Pro Leu Lys Arg Leu Ala Gly Ser Lys Val Leu Arg
            20                  25                  30

Lys Gly Asp Arg Gly Asp Glu Val Ser Gln Leu Gln Thr Leu Leu Asn
        35                  40                  45

Leu Ser Gly Tyr Asp Val Gly Lys Pro Asp Gly Ile Phe Gly Asn Asn
    50                  55                  60

Thr Phe Asn Gln Val Val Lys Phe Gln Lys Asp Asn Ser Leu Asp Ser
65                  70                  75                  80

Asp Gly Ile Val Gly Lys Asn Thr Trp Ala Glu Leu Phe Ser Lys Tyr
            85                  90                  95

Ser Pro Pro Ile Pro Tyr Lys Thr Ile Pro Met Pro Thr Ala Asn Lys
            100                 105                 110

Ser Arg Ala Ala Ala Thr Pro Val Met Asn Ala Val Glu Asn Ala Thr
        115                 120                 125

Gly Val Arg Ser Gln Leu Leu Leu Thr Phe Ala Ser Ile Glu Ser Ala
    130                 135                 140

Phe Asp Tyr Glu Ile Lys Ala Lys Thr Ser Ser Ala Thr Gly Trp Phe
145                 150                 155                 160

Gln Phe Leu Thr Gly Thr Trp Lys Thr Met Ile Glu Asn Tyr Gly Met
                165                 170                 175

Lys Tyr Gly Val Leu Thr Asp Pro Thr Gly Ala Leu Arg Lys Asp Pro
            180                 185                 190

Arg Ile Ser Ala Leu Met Gly Ala Glu Leu Ile Lys Glu Asn Met Asn
        195                 200                 205

Ile Leu Arg Pro Val Leu Lys Arg Glu Pro Thr Asp Thr Asp Leu Tyr
    210                 215                 220

Leu Ala His Phe Phe Gly Pro Gly Ala Ala Arg Arg Phe Leu Thr Thr
225                 230                 235                 240

Gly Gln Asn Glu Leu Ala Ala Thr His Phe Pro Lys Glu Ala Gln Ala
                245                 250                 255
```

```
Asn Pro Ser Ile Phe Tyr Asn Lys Asp Gly Ser Pro Lys Thr Ile Gln
            260                 265                 270

Glu Val Tyr Asn Leu Met Asp Gly Lys Val Ala Ala His Arg Lys Leu
            275                 280                 285

Glu His His His His His
            290                 295

<210> SEQ ID NO 77
<211> LENGTH: 295
<212> TYPE: PRT
<213> ORGANISM: Artificial sequence
<220> FEATURE:
<223> OTHER INFORMATION: Synthetic amino acid (Mutated peptide deriving
      from MW2 peptide linked to mutated KZ144 with C14S, C23S and C50S)

<400> SEQUENCE: 77

Met Gly Lys Pro Gly Trp Leu Arg Lys Val Ala Leu Lys Phe Lys Lys
1               5                   10                  15

Leu Ile Arg Arg Pro Leu Lys Arg Leu Ala Gly Ser Lys Val Leu Arg
            20                  25                  30

Lys Gly Asp Arg Gly Asp Glu Val Ser Gln Leu Gln Thr Leu Leu Asn
            35                  40                  45

Leu Ser Gly Tyr Asp Val Gly Lys Pro Asp Gly Ile Phe Gly Asn Asn
    50                  55                  60

Thr Phe Asn Gln Val Val Lys Phe Gln Lys Asp Asn Ser Leu Asp Ser
65                  70                  75                  80

Asp Gly Ile Val Gly Lys Asn Thr Trp Ala Glu Leu Phe Ser Lys Tyr
            85                  90                  95

Ser Pro Pro Ile Pro Tyr Lys Thr Ile Pro Met Pro Thr Ala Asn Lys
            100                 105                 110

Ser Arg Ala Ala Ala Thr Pro Val Met Asn Ala Val Glu Asn Ala Thr
            115                 120                 125

Gly Val Arg Ser Gln Leu Leu Leu Thr Phe Ala Ser Ile Glu Ser Ala
            130                 135                 140

Phe Asp Tyr Glu Ile Lys Ala Lys Thr Ser Ser Ala Thr Gly Trp Phe
145                 150                 155                 160

Gln Phe Leu Thr Gly Thr Trp Lys Thr Met Ile Glu Asn Tyr Gly Met
            165                 170                 175

Lys Tyr Gly Val Leu Thr Asp Pro Thr Gly Ala Leu Arg Lys Asp Pro
            180                 185                 190

Arg Ile Ser Ala Leu Met Gly Ala Glu Leu Ile Lys Glu Asn Met Asn
            195                 200                 205

Ile Leu Arg Pro Val Leu Lys Arg Glu Pro Thr Asp Thr Asp Leu Tyr
            210                 215                 220

Leu Ala His Phe Phe Gly Pro Gly Ala Ala Arg Arg Phe Leu Thr Thr
225                 230                 235                 240

Gly Gln Asn Glu Leu Ala Ala Thr His Phe Pro Lys Glu Ala Gln Ala
            245                 250                 255

Asn Pro Ser Ile Phe Tyr Asn Lys Asp Gly Ser Pro Lys Thr Ile Gln
            260                 265                 270

Glu Val Tyr Asn Leu Met Asp Gly Lys Val Ala Ala His Arg Lys Leu
            275                 280                 285

Glu His His His His His
            290                 295
```

<210> SEQ ID NO 78
<211> LENGTH: 295
<212> TYPE: PRT
<213> ORGANISM: Artificial sequence
<220> FEATURE:
<223> OTHER INFORMATION: Synthetic amino acid (Mutated peptide deriving
      from MW2 peptide linked to mutated KZ144 with C14S, C23S and C50S)

<400> SEQUENCE: 78

```
Met Gly Lys Pro Gly Trp Leu Ile Lys Val Ala Arg Lys Phe Lys Lys
1               5                   10                  15

Leu Ile Arg Arg Pro Leu Lys Arg Leu Ala Gly Ser Lys Val Leu Arg
            20                  25                  30

Lys Gly Asp Arg Gly Asp Glu Val Ser Gln Leu Gln Thr Leu Leu Asn
        35                  40                  45

Leu Ser Gly Tyr Asp Val Gly Lys Pro Asp Gly Ile Phe Gly Asn Asn
50                  55                  60

Thr Phe Asn Gln Val Val Lys Phe Gln Lys Asp Asn Ser Leu Asp Ser
65                  70                  75                  80

Asp Gly Ile Val Gly Lys Asn Thr Trp Ala Glu Leu Phe Ser Lys Tyr
                85                  90                  95

Ser Pro Pro Ile Pro Tyr Lys Thr Ile Pro Met Pro Thr Ala Asn Lys
            100                 105                 110

Ser Arg Ala Ala Ala Thr Pro Val Met Asn Ala Val Glu Asn Ala Thr
        115                 120                 125

Gly Val Arg Ser Gln Leu Leu Leu Thr Phe Ala Ser Ile Glu Ser Ala
130                 135                 140

Phe Asp Tyr Glu Ile Lys Ala Lys Thr Ser Ser Ala Thr Gly Trp Phe
145                 150                 155                 160

Gln Phe Leu Thr Gly Thr Trp Lys Thr Met Ile Glu Asn Tyr Gly Met
                165                 170                 175

Lys Tyr Gly Val Leu Thr Asp Pro Thr Gly Ala Leu Arg Lys Asp Pro
            180                 185                 190

Arg Ile Ser Ala Leu Met Gly Ala Glu Leu Ile Lys Glu Asn Met Asn
        195                 200                 205

Ile Leu Arg Pro Val Leu Lys Arg Glu Pro Thr Asp Thr Asp Leu Tyr
210                 215                 220

Leu Ala His Phe Phe Gly Pro Gly Ala Ala Arg Arg Phe Leu Thr Thr
225                 230                 235                 240

Gly Gln Asn Glu Leu Ala Ala Thr His Phe Pro Lys Glu Ala Gln Ala
                245                 250                 255

Asn Pro Ser Ile Phe Tyr Asn Lys Asp Gly Ser Pro Lys Thr Ile Gln
            260                 265                 270

Glu Val Tyr Asn Leu Met Asp Gly Lys Val Ala Ala His Arg Lys Leu
        275                 280                 285

Glu His His His His His
    290                 295
```

<210> SEQ ID NO 79
<211> LENGTH: 264
<212> TYPE: PRT
<213> ORGANISM: Artificial sequence
<220> FEATURE:
<223> OTHER INFORMATION: Synthetic amino acid (Magainin peptide linked
      to tail baseplate protein of Vibrio phage ICP1)

<400> SEQUENCE: 79

Met Gly Ile Gly Lys Phe Leu His Ser Ala Lys Lys Phe Gly Lys Ala

```
1               5                   10                  15
Phe Val Gly Glu Ile Met Asn Ser Gly Ser Met Ile Leu Lys Arg Gly
            20                  25                  30

Ser Ser Gly Ala Asp Val Lys Asn Met Gln Glu Tyr Leu Thr Ala Leu
            35                  40                  45

Gly Tyr Asp Thr Lys Gly Val Glu Gly Thr Phe Glu Gly Gly Thr Glu
            50                  55                  60

Ser Ala Val Lys Ala Phe Gln Lys Asp Met Ser Phe Thr Val Val Asp
65                  70                  75                  80

Gly Ile Ile Gly Asn Gln Thr Ala Lys His Leu Val Asp Met Tyr Tyr
            85                  90                  95

Gly Lys Val Val Pro Phe Gly Tyr Val Thr Asn Thr Pro Trp Val Ser
            100                 105                 110

Glu Ala Ile Glu Asp Tyr Phe Val Ser Glu Ile Lys Gly Glu Lys His
            115                 120                 125

Asn Pro Arg Val Val Gln Tyr Phe Lys Asp Ala His Ser Ser Trp Phe
            130                 135                 140

Thr Asp Asp Glu Thr Pro Trp Cys Ala Ala Ala Val Ser Ser Trp Leu
145                 150                 155                 160

Glu Arg Ala Gly Ile Arg Ser Val Arg Ser Ala Arg Ala Arg Asp His
            165                 170                 175

Ile Asn Phe Gly Thr Lys Leu Leu Glu Pro Arg Phe Gly Ala Ile Val
            180                 185                 190

Val Leu Glu Arg Gly Ala Asn Ser Gly His Val Gly Phe Val Asn Gly
            195                 200                 205

Val Thr Ala Asp Gly Lys Gln Ile Lys Val Leu Gly Gly Asn Gln Ser
            210                 215                 220

Asp Ser Val Asn Glu Arg Met Phe Gln Val Thr Arg Val Leu Gly Tyr
225                 230                 235                 240

Arg Gln Pro Glu Gly Phe Val Leu Pro Pro Cys Pro Ile Val Gly Lys
            245                 250                 255

Gly Glu Leu Ser Lys Ser Glu Ala
            260
```